(12) United States Patent
Elizarov et al.

(10) Patent No.: US 8,071,035 B2
(45) Date of Patent: Dec. 6, 2011

(54) MICROFLUIDIC RADIOSYNTHESIS SYSTEM FOR POSITRON EMISSION TOMOGRAPHY BIOMARKERS

(75) Inventors: Arkadij M Elizarov, Valley Village, CA (US); Carroll Edward Ball, Del Mar, CA (US); Jianzhong Zhang, Brea, CA (US); Hartmuth C. Kolb, Playa Del Rey, CA (US); R. Michael Van Dam, Glendale, CA (US); Lawrence Talcott Diener, Long Beach, CA (US); Sean Ford, Lake Zurich, IL (US); Reza Miraghaie, Culver City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 416 days.

(21) Appl. No.: 12/102,822

(22) Filed: Apr. 14, 2008

(65) Prior Publication Data
US 2009/0036668 A1 Feb. 5, 2009

Related U.S. Application Data

(60) Provisional application No. 61/010,822, filed on Jan. 11, 2008, provisional application No. 60/923,407, filed on Apr. 13, 2007, provisional application No. 60/923,086, filed on Apr. 12, 2007.

(51) Int. Cl.
*G21C 1/00* (2006.01)
*B01J 19/00* (2006.01)
*B01J 10/00* (2006.01)
*B01L 3/00* (2006.01)
*B01L 3/02* (2006.01)
*F16K 3/00* (2006.01)

(52) U.S. Cl. ........ 422/159; 422/129; 422/130; 422/500; 422/501; 422/502; 422/504; 422/505; 422/507; 422/509; 422/521; 422/522; 422/523; 422/524; 422/537; 422/547; 422/600; 422/603

(58) Field of Classification Search ................... 422/159, 422/500–502, 504, 505, 507, 509, 521–524, 422/537, 538, 547, 560, 600, 603; 536/122, 536/124
See application file for complete search history.

(56) References Cited

U.S. PATENT DOCUMENTS 2,716,017 A 8/1955 Linker
(Continued)

FOREIGN PATENT DOCUMENTS

WO    WO 93/22058    * 4/1993
(Continued)

OTHER PUBLICATIONS

Lee et al, Multistep Synthesis of a Radiolabeled Imaging Probe Using Integrated Microfluidics, Dec. 16, 2005, Science, vol. 310, pp. 1793-1796.*

(Continued)

*Primary Examiner* — Walter Griffin
*Assistant Examiner* — Natasha Young
(74) *Attorney, Agent, or Firm* — Joshua B. Ryan

(57) ABSTRACT

Methods and devices for a fully automated synthesis of radioactive compounds for imaging, such as by positron emission tomography (PET), in a fast, efficient and compact manner are disclosed. In particular, the various embodiments of the present invention provide an automated, stand-alone, hands-free operation of the entire radiosynthesis cycle on a microfluidic device with unrestricted gas flow through the reactor, starting with target water and yielding purified PET radiotracer within a period of time shorter than conventional chemistry systems. Accordingly, one aspect of the present invention is related to a microfluidic chip for radiosynthesis of a radiolabeled compound, comprising a reaction chamber, one or more flow channels connected to the reaction chamber, one or more vents connected to said reaction chamber, and one or more integrated valves to effect flow control in and out of said reaction chamber.

41 Claims, 32 Drawing Sheets

U.S. PATENT DOCUMENTS

| | | | |
|---|---|---|---|
| 2,971,851 A | 2/1961 | Kurtz | |
| 3,378,406 A | 4/1968 | Rosansky | |
| 3,407,249 A | 10/1968 | Patrick | |
| 3,507,708 A | 4/1970 | Vignaud | |
| 3,613,729 A | 10/1971 | Dora | |
| 3,663,409 A | 5/1972 | Greene | |
| 4,062,750 A | 12/1977 | Butler | |
| 4,326,518 A | 4/1982 | Williams | |
| 4,500,905 A | 2/1985 | Shibata | |
| 4,696,195 A | 9/1987 | Savonlahti et al. | |
| 4,721,133 A | 1/1988 | Sundblom | |
| 4,924,241 A | 5/1990 | Parks et al. | |
| 4,977,948 A | 12/1990 | Chandley | |
| 5,624,556 A | 4/1997 | Kutowy | |
| 5,765,591 A | 6/1998 | Wasson et al. | |
| 5,863,502 A | 1/1999 | Southgate et al. | |
| 5,989,402 A | 11/1999 | Chow et al. | |
| 6,065,195 A | 5/2000 | Chatterjee et al. | |
| 6,145,810 A | 11/2000 | Connolly et al. | |
| 6,158,712 A | 12/2000 | Craig | |
| 6,399,025 B1 | 6/2002 | Chow | |
| 6,720,710 B1 | 4/2004 | Wenzel et al. | |
| 6,752,371 B2 | 6/2004 | Herbert et al. | |
| 6,814,337 B2 | 11/2004 | Schmaltz | |
| 6,830,729 B1 | 12/2004 | Holl et al. | |
| 6,929,030 B2 | 8/2005 | Unger et al. | |
| 7,040,338 B2 | 5/2006 | Unger et al. | |
| 7,223,363 B2 | 5/2007 | McNeely et al. | |
| 2001/0012612 A1 | 8/2001 | Petersen | |
| 2002/0048536 A1 | 4/2002 | Bergh et al. | |
| 2002/0166585 A1 | 11/2002 | O'Connor et al. | |
| 2003/0008308 A1 | 1/2003 | Enzelberger et al. | |
| 2003/0019833 A1 | 1/2003 | Unger et al. | |
| 2003/0175947 A1 | 9/2003 | Liu et al. | |
| 2003/0190608 A1 | 10/2003 | Blackburn | |
| 2003/0194716 A1 | 10/2003 | Knoll | |
| 2003/0214057 A1 | 11/2003 | Huang | |
| 2004/0037739 A1 | 2/2004 | McNeely et al. | |
| 2004/0101444 A1 | 5/2004 | Sommers et al. | |
| 2005/0232387 A1* | 10/2005 | Padgett et al. | 376/194 |
| 2005/0266582 A1 | 12/2005 | Modlin et al. | |
| 2006/0063160 A1* | 3/2006 | West et al. | 435/6 |
| 2006/0078475 A1 | 4/2006 | Tai et al. | |
| 2006/0150385 A1 | 7/2006 | Gilligan et al. | |
| 2006/0163069 A1 | 7/2006 | Prak et al. | |
| 2007/0012891 A1 | 1/2007 | Maltezos | |
| 2007/0272309 A1 | 11/2007 | Rehm et al. | |
| 2008/0281090 A1* | 11/2008 | Lee et al. | 536/122 |

FOREIGN PATENT DOCUMENTS

| | | |
|---|---|---|
| WO | 9322058 | 11/1993 |
| WO | 9511080 | 4/1995 |
| WO | WO 95/11080 A1 * | 4/1995 |
| WO | 0043766 | 7/2000 |
| WO | WO 00/43766 A1 | 7/2000 |
| WO | 0073412 | 12/2000 |
| WO | 0141931 | 6/2001 |
| WO | 0173417 | 10/2001 |
| WO | 0240874 | 5/2002 |
| WO | 02070932 | 9/2002 |
| WO | 02072264 | 9/2002 |
| WO | 03024597 | 3/2003 |
| WO | 03078358 | 9/2003 |
| WO | WO 03/078358 A2 * | 9/2003 |
| WO | 03098219 | 11/2003 |
| WO | WO 03/098219 A1 * | 11/2003 |
| WO | 2006060748 | 6/2006 |
| WO | 2006071470 | 7/2006 |
| WO | WO 2006/071470 A2 * | 7/2006 |
| WO | 2006098817 | 9/2006 |
| WO | 2006116629 | 11/2006 |
| WO | WO 2006/116629 A2 | 11/2006 |
| WO | 2007027928 | 3/2007 |
| WO | 2007041486 | 4/2007 |
| WO | WO 2007/027928 A1 * | 5/2007 |
| WO | WO 2007/041486 A2 * | 6/2007 |
| WO | 2007092472 | 8/2007 |
| WO | WO 2007/092472 A1 * | 8/2007 |
| WO | WO 2006/098817 A1 * | 9/2008 |

OTHER PUBLICATIONS

Gillies et al, Microfluidic reactor for the radiosynthesis of PET radiotracers, Mar. 2006, Applied Radiation and Isotopes, 64, pp. 325-332.*

Dharmatilleke, S., et al. "Three-dimensional silicone microfluidic interconnection scheme using sacrificial wax filaments", Proceedings of SPIE, vol. 4177, pp. 83-90, Aug. 28, 2006.

Unger, M.A., et al., "Monolithic Microfabricated Valves and Pumps by Multilayer Soft Lithography", Science, vol. 288, No. 5463, pp. 113-116 (Apr. 2000).

Thorsen, T., et al., "Microfluidic Large-Scale Integration", Science, vol. 298, No. 5593, pp. 580-584 (Sep. 2002).

Rolland, J.P., et al., "Solven-Resistant Photocurable 'Liquid Teflon' for Microfluidic Device Fabrication", JACS, vol. 126, pp. 2322-2323 (2004).

van Dam, R.M., "Solvent-Resistant Elastomeric Microfluidic Devices and Applications", PhD Thesis, California Institute of Technology (Aug. 2005).

Studer, V., et al., "Scaling Properties of a Low-Actuation Pressure Microfluidc Valve", Journal of Applied Physics, 95 (1), pp. 393-398 (2004).

Fredrickson, C.K., et al., "Macro-to-Macro Interfaces for Microfluidic Devices", Lab on a Chip, 4, pp. 526-533 (20004).

Gu, W., "Computerized Microfluidic Cell Culture Using Elastomeric Channels and Braille Displays", PNAS, vol. 101, No. 45, pp. 15861-15866 (2004).

Lai, S. M., et al. "Knoevenagel condensation reaction in a membrane microreactor" Chem. Commun, 2003, 218-219.

Yamamoto, T. et al., "PDMS-glass hybrid microreactor array with embedded temperature control device. Application to cell-free protein synthesis", Lab Chip, 2002, 2, 197-202.

Psaltis, D. et al. "Developing optofluidic technology through the fusion of microfluidics and optics", Nature, 2005, 442, 381-386.

Grover, W., H. et al., "Monolithic membrane valves and diaphragm pumps for practical large-scale integration into glass microfluidic devices" Sensors and Actuators E, 2003, 89, 315-323.

Lee, C. C. et al., "Miltistep Synthesis of a Radiolabeled Imaging Probe Using Integrated Microfluics", Science, 2005, 310, 1793-1979.

Gillies, J. M. et al., "Microfluidic reactor for the radiosynthesis of PET radiotracers", J. Appl. Rad. Isot. 2005, 64, 325-332.

Yuen, P.K. et al., "Semi-disposable microvalves for use iwth microfabricated devices or microchips", J. Micromech. Microeng. 2000, 10, 401-409.

* cited by examiner

FIG. 11

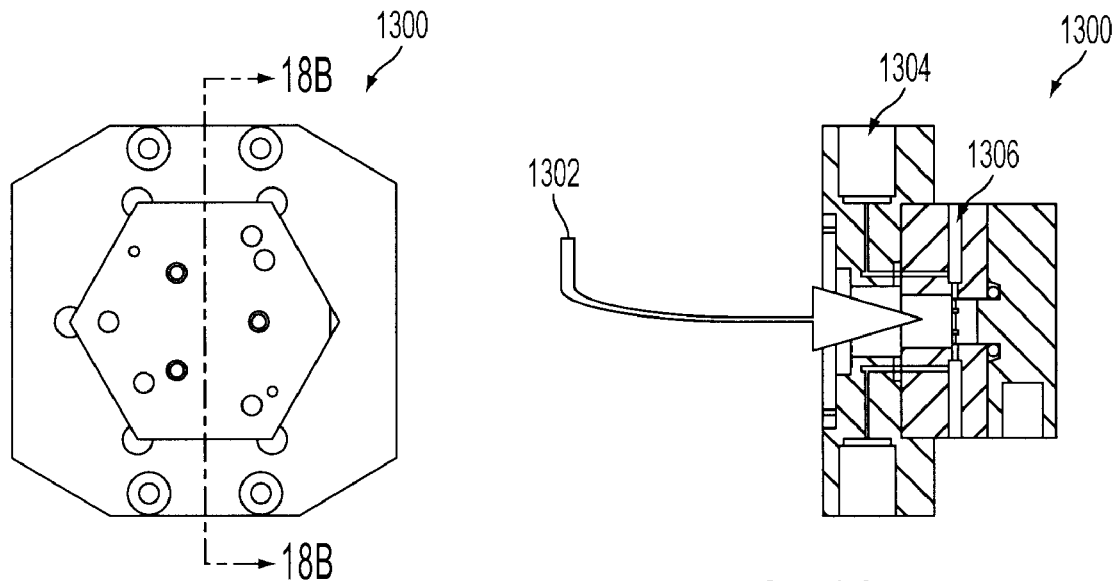
FIG. 18A
FIG. 18B
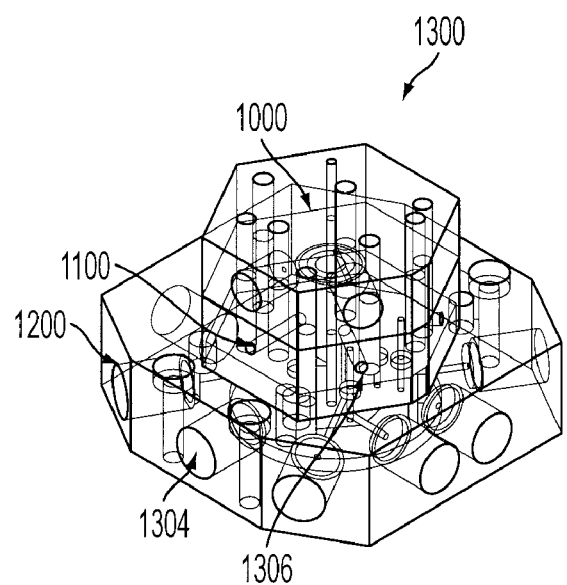
FIG. 18C

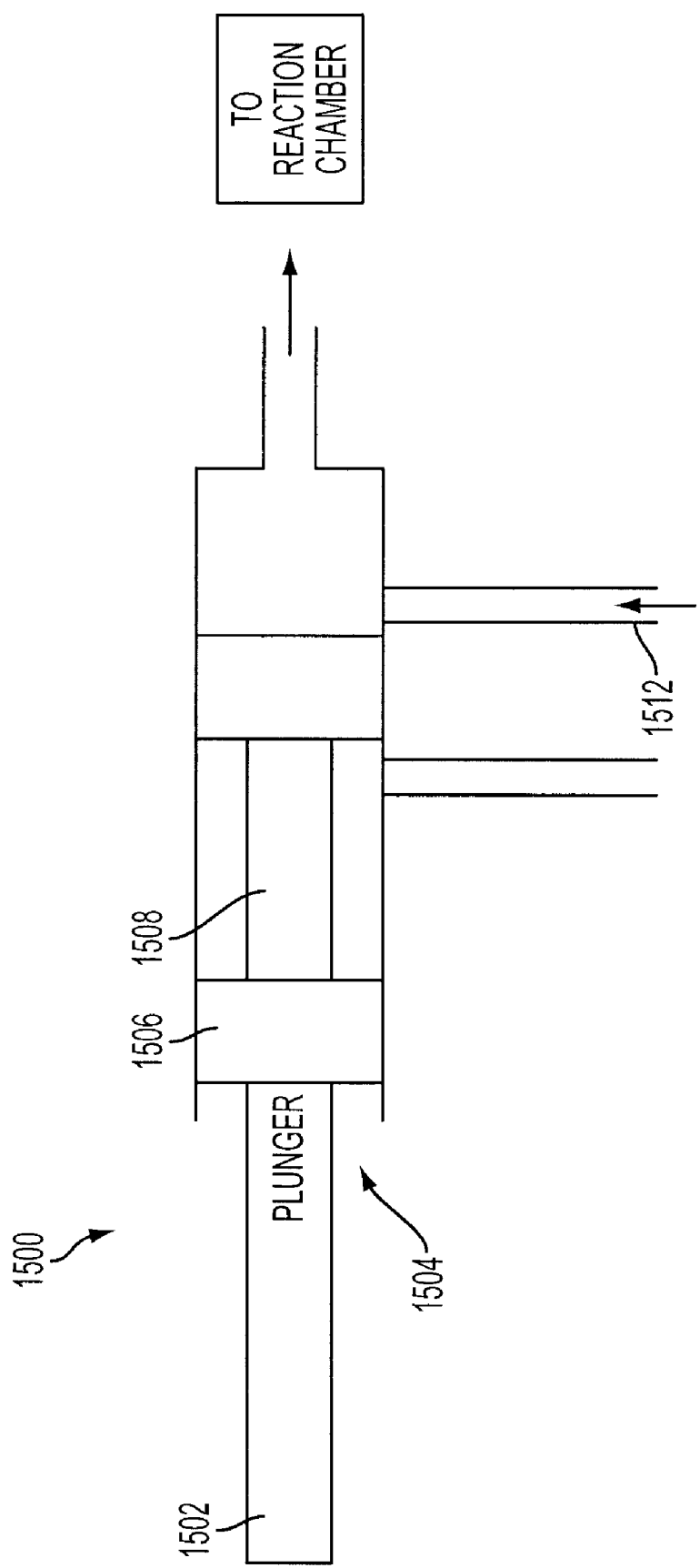

US 8,071,035 B2

MICROFLUIDIC RADIOSYNTHESIS SYSTEM FOR POSITRON EMISSION TOMOGRAPHY BIOMARKERS

RELATED APPLICATIONS

This application claims priority to U.S. Provisional Application No. 60/923,086 filed Apr. 12, 2007, U.S. Provisional Application No. 60/923,407, filed Apr. 13, 2007, U.S. Nonprovisional application Ser. No. 11/895,636, filed Aug. 23, 2007 and U.S. Provisional Application No. 61/010,822, filed Jan. 11, 2008, the contents of each of which is hereby incorporated in its entirety by reference.

FIELD OF THE INVENTION

The present invention relates generally to microfluidic devices and related technologies, and to chemical processes using such devices. More specifically, the invention relates to a fully automated synthesis of radioactive compounds for imaging, such as by positron emission tomography (PET), in a fast, efficient and compact manner. In particular, embodiments of the present invention relate to an automated, stand-alone, microfluidic instrument for the multi-step chemical synthesis of radiopharmaceuticals, such as probes for PET and methods of using such systems.

BACKGROUND OF THE INVENTION

This section is intended to provide a background or context to the invention that is recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Positron Emission Tomography (PET) is a molecular imaging technology that is increasingly used for detection of disease. PET imaging systems create images based on the distribution of positron-emitting isotopes in the tissue of a patient. The isotopes are typically administered to a patient by injection of probe molecules that comprise a positron-emitting isotope (e.g., carbon-11, nitrogen-13, oxygen-15, or fluorine 18) covalently attached to a molecule that is readily metabolized or localized in the body or that chemically binds to receptor sites within the body. For PET probes the short half-lives of the positron emitters require that synthesis, analysis and purification of the probes are completed rapidly.

Large-volume synthesis modules have been developed and used for the preparation of a number of radiopharmaceutical compounds. Common pharmaceuticals radiolabeled with F-18 include 2-deoxy-2-[F-18]-fluoro-D-glucose ($^{18}$F-FDG), 3'-deoxy-3'-[F-18]-fluorothymidine($^{18}$F-FLT), 9-[4-[F-18]fluoro-3-(hydroxymethyl)butyl]guanine ($^{18}$F-FHBG), 9-[(3-[F-18]fluoro-1-hydroxy-2-propoxy)methyl]guanine ($^{18}$F-FHPG), 3-(2'-[F-18]fluoroethyl)spiperone($^{18}$F-FESP), 4-[F-18]fluoro-N-[2-[1-(2-methoxyphenyl)-1-piperazinyl] ethyl]-N-2-pyridinyl-benzamide($^{18}$F-p-MPPF), 2-(1-{6-[(2-[F-18]fluoroethyl)-(methyl)amino]-2-naphthyl}ethylidine) malononitrile($^{18}$F-FDDNP), 2-[F-18]fluoro-α-methyltyrosine, [F-18]fluoromisonidazole($^{18}$F-FMISO), 5-[F-18]fluoro-2'-deoxyuridine (18F-FdUrd). Other common radiolabeled compounds include $^{11}$C-methionine and $^{11}$C-acetic acid. Large volume synthesis modules occupy a large amount of space and the chemical process requires longer reaction time cycles than desired for the preparation of the labeled compounds. Such modules are also difficult to modify for the research and development of new compounds and probes. Generally the reactions in such modules take place with reduced efficiency due to the tremendous dilution of reagents necessary for macroscopic liquid handling.

The synthesis of the [F-18]-labeled molecular probe, 2-deoxy-2-[F-18]-fluoro-D-glucose (18F-FDG), is based on three major sequential synthetic processes: (i) Concentration of the dilute [F-18]fluoride solution (1-10 ppm) that is obtained from the bombardment of target water, [O-18]$H_2O$, in a cyclotron; (ii) [F-18]fluoride substitution of the mannose triflate precursor; and (iii) acidic hydrolysis of the fluorinated intermediate. Presently, [F-18]FDG is produced on a routine basis in a processing time (or cycle time) of about 50 minutes using macroscopic commercial synthesizers. These synthesizers consist, in part, mechanical valves, glass-based reaction chambers and ion-exchange columns. The physical size of these units is typically in the order of 80 cm×40 cm×60 cm. Descriptions of macroscopic synthesizers can be found, for example, in WO2007/066089, WO2005/057589, US2007/0031492, and US2004/022696.

Because of the long processing times, low reagent concentrations of macroscopic synthesizers, and the short half-life of [F-18]fluorine ($t_{1/2}$=109.7 min), a considerable decrease in the radiochemical yields of the resulting probe are inevitably obtained. Moreover, because a number of commercialized automation system are constructed for macroscopic synthesis, the process requires the consumption of large amounts of valuable reagents (e.g., precursors or Kryptofix2.2.2), which is inefficient and wasteful for both clinical and research purposes. For example, the required radioactivity for [F-18]FDG PET imaging of a single patient is about 20 mCi, which corresponds to about 240 ng of FDG. For small animal imaging applications, such as for a mouse, only about 200 μCi or less of [F-18]FDG is required. The same hold true for FLT.

Accordingly, there is a need to develop smaller or miniaturized systems and devices that are capable of processing such small quantities of molecular probes. In addition, there is a need for such systems that are capable of expediting chemical processing to reduce the overall processing or cycle times, simplifying the chemical processing procedures, and at the same time, provide the flexibility to produce a wide range of probes, biomarkers and labeled drugs or drug analogs, inexpensively.

Microfluidic devices can offer a variety of advantages over macroscopic reactors, such as reduced reagent consumption, high concentration of reagents, high surface-to-volume ratios, and improved control over mass and heat transfer. (See, for example, K. Jahnisch, V. Hessel, H. Lowe, M. Baems, *Angew. Chem.* 2004, 116: 410-451; *Angew. Chem. Int. Ed. Engl.* 2004, 43:406-446; P. Watts, S. J. Haswell, *Chem. Soc. Rev.* 2005, 34:235-246; and G. Jas, A. Kirschning, *Chem. Eur. J.* 2003, 9:5708-5723.)

SUMMARY OF THE INVENTION

The present invention relates generally to microfluidic devices and related technologies, and to chemical processes using such devices. More specifically, embodiments of the present invention relate to a fully automated synthesis of radioactive compounds for imaging, such as by positron emission tomography (PET), in a fast, efficient and compact manner. In particular, the various embodiments of the present invention provide an automated, stand-alone, hands-free operation of the entire radiosynthesis cycle on a microfluidic device with unrestricted gas flow through the reactor starting with target water and yielding purified PET radiotracer within a period of time shorter than conventional chemistry systems, exhibiting significantly higher reaction yields and requiring significantly smaller amounts of precursors. Accordingly, one aspect of the present invention is related to a microfluidic chip for radiosynthesis of a radiolabeled compound, comprising a reaction chamber, one or more flow channels connected to the reaction chamber, one or more vents connected to said reaction chamber, and one or more integrated valves to effect flow control in and out of said reaction chamber. The terms "device," "apparatus" and "instrument" are used interchangeably herein and are not intended to limit the scope of the claimed invention.

In one embodiment, the reaction chamber is located within a reactor section and a lid section of the chip that are press-fitted together. In another embodiment at least a portion of the lid is transparent. In another embodiment, the lid is comprised of a glass window within a frame. In another embodiment the chip is monolithic and the reaction chamber is completely enclosed within the chip. According to another embodiment, the chip further comprises an interface configured to effect delivery of products to the reaction chamber. In yet another embodiment, the interface is connected to the reactor section of the chip. Another embodiment provides that the floor of the reaction chamber comprises a curved section. In another embodiment, the chip has a hexagonal shape.

In accordance with another embodiment, the chip further comprises a heater for heating said reaction chamber. According to one embodiment, the heater comprises at least one of a heating element, a resistive heater, a radiator heater, a microwave heater, and a laser device for remote delivery of heat to the reaction chamber. In yet another embodiment, the heater is coupled to the chip through an opening in the base of the chip. In one embodiment, an air gap separates the heater from the sidewalls of said opening, while in another embodiment the heater is separated from the reaction chamber by a 250 micron section. In one embodiment, the section comprises a doped DCPD material.

According to another embodiment of the present invention, the valves are controlled by pneumatic actuators. In a different embodiment, the valves are controlled by solenoids. According to another embodiment, the valve comprises a dual port plunger with one or more thin sections that are separated by one or more ridges. In a different embodiment, the valve comprises a plunger with a thin metal portion, a tip, and one or more o-rings adapted to prevent gas escape from said reaction chamber.

In yet another embodiment, the chip further comprises one or more reaction chambers. In another embodiment, the chip comprises an ion exchange column integrated onto the chip. While in one embodiment, the chip comprises an HPLC integrated into said chip, in a different embodiment, the chip comprises an HPLC integrated into an interface section of said chip. In another embodiment, the chip comprises one or more internal filters for removal of exhaust. According to another embodiment, the reaction chamber has a cylindrical shape and a volume of 60 micro liters, and in a different embodiment, the chip is configured as a closed system with no plumbing extensions.

In accordance with another embodiment of the present invention, the chip is further adapted to communicate with a network of fluid and gas delivery and removal. In one embodiment, one or more syringes are used for delivery of at least one of a fluid or gas to the chip. In one embodiment, the syringes are located below one or more vials with liquid contents to effect efficient delivery of liquids to the chip. In another embodiment, the syringes are used for delivery of gas to said chip. In a different embodiment, the network is adapted to operate with at least one of a pre-filled individual vial and a pre-packaged cartridge. In one embodiment, the cartridge contains a pre-measured amount of reagent sufficient for single use with the chip. In a different embodiment, a controlled delivery of liquids is effected by gradual increase of pressure against a closed vent.

According to another embodiment of the present invention, solvent evaporation and vapor removal are effected by flowing gas over the solution inside the reaction chamber. In one embodiment the gas is Nitrogen. According to a different embodiment, superheating of the contents of the reaction chamber is effected by closing the vents and heating the reactor chamber with a heater. Another embodiment comprises pressurizing the reaction chamber prior to applying the heat. According to a different embodiment, the chip further comprises an integrated solvent removal module.

Another aspect of the present invention relates to a portable device for automated radiosynthesis of a radiolabeled compound, comprising a microfluidic chip, a reagent source comprising at least one reagent in fluid communication with the chip, a gas and fluid delivery and removal network, a controller adapted to control the operation of the network, and localized radiation shielding for shielding one or more radiation critical components of the device. In one embodiment, the device further comprises a camera for monitoring a reaction chamber within the microfluidic chip. According to another embodiment, the device further comprises a Machine Vision system adapted to recognize the completion of one or more steps in accordance with information received from the camera. In one embodiment, a second step is started upon immediate completion of a first step.

According to another embodiment of the present invention, the device is configured to operate in a batch mode. In one embodiment, the device is configured to operate in a flow-through mode, while in a different embodiment, the device is configured to operate in a hybrid batch-flow through mode. In a different embodiment of the present invention the localized shielding is effected for at least one of an ion exchange column and F-18 source. In another embodiment, the controller comprises a programmable logic controller and a user interface. In one embodiment, the user interface is configured to effect at least one of a manual and an automatic operation of the device.

According to another embodiment, the device further comprises one or more internal filters for removal of exhaust. In another embodiment, the localized shielding prevents user exposure to radiation in multiple synthesis runs conducted by the user. In one embodiment, all of loaded reagents are consumed in accordance with a zero-waste system, and in a different embodiment, the device is further adapted to provide efficient elution of [f-18]fluoride from an ion exchange column. In another embodiment, the device further comprises self-metering of reagents, and in another embodiment, the device is further adapted for fully automated operation.

A different aspect of the present invention is related to a method for radiosynthesis of a radiolabeled compound, comprising introducing one or more reagents into microfluidic chip, the chip comprising a reaction chamber, one or more flow channels connected to the reaction chamber, one or more vents connected to the reaction chamber, and one or more integrated valves to effect flow control in and out of the reaction chamber; processing the reagent(s) to generate a radiolabeled compound; and collecting the radiolabeled compound.

A different aspect of the present invention involves a program code embodied on a computer-readable medium, the program code comprising instructions for causing a controller to implement a method for radiosynthesis of a radiolabeled compound using a microfluidic chip, the method comprising introducing one or more reagents into a reaction chamber, operating the synthesis system to process the reagent(s) responsive to a predetermined algorithm to generate a radiolabeled compound, and collecting the radiolabeled compound. In another embodiment the entire process starting with Radionuclide received from the cyclotron and finishing with a purified product in an injectable formulation is performed automatically without user intervention.

In addition, the methods and devices in accordance with the various embodiments of the present invention may provide the following additional features and benefits:

The device is capable of conducting multiple runs without user exposure to radiation (including syntheses of different products);

A "zero-waste" microfluidic system using 100% of the reagents loaded;

Solvents may be evaporated below their boiling points without vacuum application in a microfluidic device;

Reactions may be done in solutions heated to temperatures that double the boiling point of the solvent used (or exceed it by over 100 degrees C.);

The device may comprise a Monolithic chip, without a separate lid and reactor sections;

The device may be used without an interface layer with pins press-fitted into its ports that in turn connect to tubing;

The device allows ultra-efficient fractional elution of [F-18]fluoride from ion exchange column;

The reaction chamber floor may comprise any material with high thermal conductivity and an inert surface;

The chip allows self-metering of the reagents (e.g., by surface tension);

The chip allows reagents on solid supports (e.g., by placing beads in the reactor that can remain in the reactor while solutions enter and exit);

A double syringe system that allows fractionation of reagents (e.g., one syringe with reagent and another with gas);

Localized shielding that protects user and electronics at the same time;

Direct loading of HPLC column from chip;

Automated product recognition and isolation;

Tabletop operation—no exhaust handling such as a fume hood;

An automated organic solvent removal system; and

The entire process (from F-18 in target water to purified product formulated for injection into a patient) can be performed automatically with a single command.

These and other advantages and features of various embodiments of the present invention, together with the organization and manner of operation thereof, will become apparent from the following detailed description when taken in conjunction with the accompanying drawings.

BRIEF DESCRIPTION OF THE DRAWINGS

Embodiments of the invention are described by referring to the attached drawings, in which:

FIG. 11 illustrates a user interface for the microfluidics-based instrument in accordance with an exemplary embodiment of the present invention;

FIG. 14 illustrates a fluid and gas network for a microfluidics-based instrument in accordance with an exemplary embodiment of the present invention;

FIG. 18 illustrates a combined microfluidic chip and interface assembly in accordance with an exemplary embodiment of the present invention;

DETAILED DESCRIPTION OF THE CERTAIN EMBODIMENTS

Figure 1:
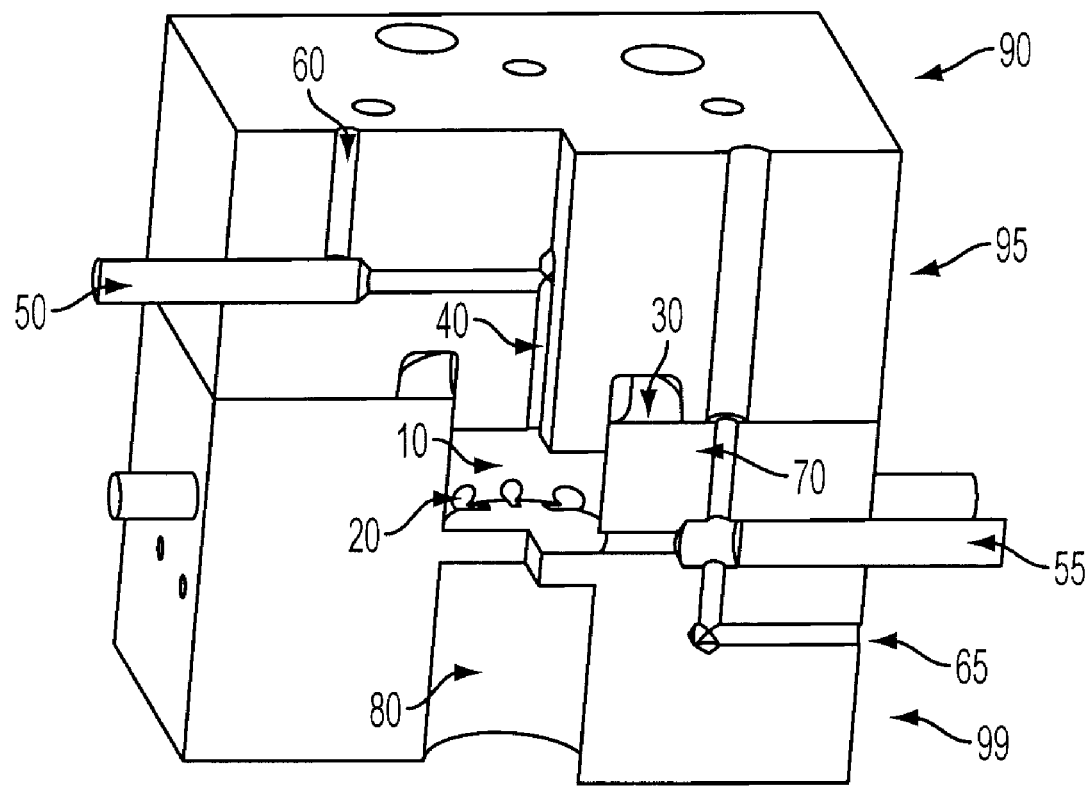
FIG. 1 illustrates a cross-section of an exemplary microfluidic chip in accordance with an embodiment of the present invention.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions.

U.S. patent application Ser. No. 11/895,636, filed Aug. 23, 2007, titled "System for Purification and Analysis of Radiochemical Products Yielded by Microfluidic Synthesis Devices," is hereby incorporated by reference in its entirety.

Generally, conventional automated synthesizers for synthesizing radiopharmaceutical are inefficient, and efficient microfluidic reactors identified so far require manual operation. The various embodiments of the present invention allow automatic operation of microfluidic reactors. Previous microfluidic reactors have been operated inside stationary leaded hot cells by a variety of mechanical, pneumatic or very simple electronic controls, requiring operator attention at all times; these reactors demonstrate notable variability as a result. The automation enabled by one aspect of this invention makes the microfluidic device autonomous and portable. In one aspect, the microfluidic system of the present invention can be used in either clinical or R&D setting by medical personnel, and does not require the constant presence of an engineer or specially trained operator. Furthermore, the microfluidic system in accordance with embodiments of the present invention allows various steps of the synthesis to take place in a controlled traceable manner. In an alternative aspect of the present invention, syringe drivers can be used to deliver and meter reagents more precisely. Generally, sensors can be used to monitor step completion such as, for example, solvent evaporation. This arrangement can lead to a faster and more fail-safe instrument.

In particular, embodiments of the present invention relate to a microfluidic system for the fully-automated synthesis of biomarkers, or radiolabeled pharmaceuticals, for positron emission tomography. Some of the advantages associated with the various embodiments of the present invention include, for example, reduced reagent use (thus reduced cost of chemical product), increased concentration of the radiolabel, such as F-18, which drives up reaction efficiencies and yields; and the ability to synthesize compounds on demand and in a flexible manner. Other advantages of the various embodiments of the present invention include the ability to synthesize multiple products sequentially without user exposure to radiation between the runs (which is inevitable in conventional systems), and the ability to perform high pressure reactions (e.g., with hundreds of psi).

The presently disclosed system can contain mechanisms to add additional reagent modules, waste modules, and synthesis modules to allow the system to be used for different biomarkers from one run to the next, or even simultaneously. In cases when different biomarker syntheses involve the same number of steps, the instrument may be reused without hardware modifications, or with single-use cartridges that are pre-loaded with reagents and/or solvents for a single run. This ease of use enables tremendous flexibility in a research environment or in specialized clinical situations, where on-demand synthesis of biomarkers is needed, such as when several patients in the same day require different scans performed with different biomarkers.

In one aspect, the present invention provides an automated instrument that is easy to use and flexible. As such, the system enables non-experts to synthesize a variety of PET biomarkers on demand for biomarker development, synthesis-optimization, and testing. In another aspect, the present invention provides an instrument that can be deployed in hospitals further from cyclotrons than is currently possible. The presently disclosed devices enable synthesis of fresh product on demand as contrasted to the decayed products associated with conventional systems that require delivery from a centralized (and perhaps distant) synthesis facility. This type of on-site instrument greatly expands the accessibility of PET scanning to additional clinics, patients and research labs, and provides additional flexibility in obtaining desired biomarkers (with high specific activity) that goes beyond what is available from the local radio-pharmacy.

To facilitate the understanding of the disclosed methods, systems and devices, the following provides a listing of terms and definitions that are used in the art of organic synthesis, engineering and pharmaceutical sciences.

A "microfluidic device" or "microfluidic chip" or "synthesis chip" or "chip" is a unit or device that permits the manipulation and transfer of small amounts of liquid (e.g., microliters or nanoliters) into a substrate comprising microchannels. The device may be configured to allow the manipulation of liquids, including reagents and solvents, to be transferred or conveyed within the micro channels and reaction chamber using mechanical or non-mechanical pumps. The device may be constructed using micro-electromechanical fabrication methods as known in the art. Alternatively, the devices can be machined using computer numerical control (CNC) techniques. Examples of substrates for forming the device include glass, quartz or polymer. Such polymers may include PMMA (polymethylmethacrylate), PC (polycarbonate), PDMS (polydimethylsiloxane), DCPD (polydicyclopentadiene), PEEK and the like. Such device may comprise columns, pumps, mixers, valves and the like. Generally, the microfluidic channels or tubes (sometimes referred to as micro-channels or capillaries) have at least one cross-sectional dimension (e.g., height, width, depth, diameter), which by the way of example, and not by limitation may range from 1,000 μm to 10 μm. The micro-channels make it possible to manipulate extremely small volumes of liquid, for example on the order of nL to μL. The micro reactors may also comprise one or more reservoirs in fluid communication with one or more of the micro-channels, each reservoir having, for example, a volume of about 5 to about 1,000 μL.

"Reaction chamber" (sometimes referred to as "reactor" or "micro-reactor") refers to feature on the microfluidic chip (such as described here or for example in U.S. Ser. Nos. 11/514,396, 11/540,344, or U.S. Ser. No. 11/701,917, each of which is incorporated herein in its entirety by reference) where the reactions may take place. The reaction chamber may, for example, be cylindrical in shape. The reaction chamber has one or more micro-channels connected to it that deliver reagents and/or solvents or are designed for product removal (e.g., controlled by on-chip valves, or equivalent devices). By the way of example, and not by limitation, the reaction chamber may have a diameter to height ratio of greater than about 0.5 to 10, or more. By the way of example, and not by limitation, the reactor height may be about 25 micrometer to about 20,000 micrometers.

"Column" means a device that may be used to separate, purify or concentrate reactants or products. Such columns are well known in the art, and include, but are not limited to, ion exchange and affinity chromatography columns.

A "flow channel" or "channel" means a microfluidic channel through which a fluid, solution, or gas may flow. By the way of example, and not by limitation, such channels may have a cross section of about 0.1 mm to about 1 mm. By way of example, and not by limitation, the flow channels of embodiments of the present invention may also have a cross section dimension in the range of about 0.05 microns to about 1,000 microns. The particular shape and size of the flow channels depend on the particular application required for the reaction process, including the desired throughput, and may be configured and sized according to the desired application.

"Target water" is [$^{18}$O]H$_2$O after bombardment with high-energy protons in a particle accelerator, such as a cyclotron. It contains [$^{18}$F]fluoride. In one embodiment of the present invention, preparation of target water is contemplated separately from the system disclosed herein. In one embodiment of the present invention, target water is supplied to the system from a cartridge; in another embodiment, from a pre-filled individual vial.

A microfluidic "valve" (or "micro-valve") means a device that may be controlled or actuated to control or regulate fluid, gas or solution flow among various components of the microfluidic device, including flow between flow channels, solvent or reagent reservoirs, reaction chamber, columns, manifold, temperature controlling elements and devices, and the like. By the way of example, and not by limitation, such valves may include mechanical (or micromechanical valves), (pressure activated) elastomeric valves, pneumatic valves, solid-state valves, etc. Examples of such valves and their method of fabrication may be found, for example, in "The New Generation of Microvalves" *Analytical Chemistry*, Felton, 429-432 (2003).

The term "radioactive isotope" refers to isotopes exhibiting radioactive decay (e.g., emitting positrons). Such isotopes are also referred to in the art as radioisotopes or radionuclides. Radioactive isotopes are named herein using various commonly used combinations of the name or symbol of the element and its mass number (e.g., $^{18}$F, [F-18], fluorine-18). Exemplary radioactive isotopes include I-124, F-18, C-11, N-13, and O-15, which have half-lives of 4.2 days, 110 minutes, 20 minutes, 10 minutes, and 2 minutes, respectively.

The terms FLT precursor may be used to refer to "N-dimethoxytrityl-5'-O-dimethoxytrityl-3'-O-nosyl-thymidine" (also known as "BOC-BOC-Nosyl"); FMISO may be used to refer to [F-18]fluoromisoindazole, and FHBG may be used to refer to 9-[4-[18F]fluoro-3-(hydroxymethyl)butyl]guanine.

The term "reactive precursor" or "precursor" refers to an organic or inorganic non-radioactive molecule that is reacted with a radioactive isotope, typically by nucleophilic substitution, electrophilic substitution, or ionic exchange, to form the radiopharmaceutical. The chemical nature of the reactive precursor depends upon the physiological process to be studied. Typically, the reactive precursor is used to produce a radiolabeled compound that selectively labels target sites in the body, including the brain, meaning the compound can be reactive with target sites in the subject and, where necessary, capable of transport across the blood-brain barrier. Exemplary organic reactive precursors include sugars, amino acids, proteins, nucleosides, nucleotides, small molecule pharmaceuticals, and derivatives thereof. One common precursor used in the preparation of $^{18}$F-FDG is 1,3,4,6-tetra-O-acetyl-2-O-trifluoromethanesulfonyl-β-D-mannopyranose.

The phrase "reactor temperature" refers to a temperature observed, measured and/or maintained in the reaction chamber.

"Reaction time" refers to the time allowed for a reaction to run before the next step takes place.

The phrase "reagent pressure" or "solvent pressure" refers to the pressure of a gas (usually an inert gas such as nitrogen or argon) applied to a reagent or solvent vial that drives a reagent or solvent into a flow channel, e.g. on the way to the reaction chamber.

The phrase "time of reagent filling" or "time of solvent filling" refers to the time allowed for a reagent or solvent to enter the microfluidic chip before the on-chip valve closes, thereby inhibiting passage of additional reagent or solvent into the reaction chamber.

The term "evaporation" refers to the change in state of solvent from liquid to gas that is usually followed by removal of that gas from the reactor. One method for removing gas is effected by applying a vacuum. Various solvents are evaporated during the synthetic route disclosed herein, such as for example acetonitrile and water. As known to those of skill in the art, each solvent, such as acetonitrile and water, may have a different evaporation time and/or temperature. In another embodiment the evaporation takes place by heating the reaction chamber while flowing an inert gas over the reaction mixture to effect the removal of vapors from the reaction chambers.

The term "elution" generally refers to removal of a compound from a particular location. Elution of [F-18]fluoride from the ion exchange column refers to the conveyance of [F-18]fluoride by the eluting solution from the column to the reaction chamber. Elution of product from the reaction chamber refers to conveyance of the product from the reaction chamber to the off-chip product vial (or into the purification system) by, for example, flushing the reaction chamber with a volume of solvent, e.g. water.

The "off/on time" in reference to the vacuum (or gas pressure) applied at a point in the system refers to the point in time of the radiosynthesis operation when the vacuum (or gas pressure) is turned on or off.

"Inert gas pressure," including "nitrogen pressure" or "argon pressure" refers to pressure of inert gas, such as nitrogen or argon, allowed past a given regulator.

The phrase "internal filter" refers to a vial, a syringe or another container that is filled with absorbent material such as charcoal and comprises two ports. When the exhaust from the microfluidic chip is passed through such a filter, radioactive and non-radioactive contaminants are generally caught by and stay on the filter. After passage of the reaction exhaust through an internal filter purified gas is released into the atmosphere. Use of an appropriate internal filter reduces or even eliminates the need for an additional exhaust processing for safe operation of the portable system. In one embodiment, it is not necessary to operate the portable system disclosed herein in a fume hood.

The term "priming" when used in reference to a reagent flow channel refers to conveying a reagent through the flow channel connecting the reagent source and the reaction chamber, wherein the reagent flow passes a closed on-chip valve and flows via an open flow channel to a waste receptacle. In this fashion, when the reagent is to be added to the reaction chamber, the corresponding on-chip valve is opened and pneumatic actuation conveys the reagent from the primed flow channel into the reaction chamber with minimal delay. In the alternative, when a flow channel is not primed, the reagent must travel the length of the flow channel from the reagent source to the reaction chamber, displacing the gas in that path through the reaction chamber and an open vent channel on the synthesis chip. This can lead to losses of reagents or solvents, which is avoided by priming the flow channel. Analogously, when appropriate, the term 'priming' can be used in reference to a solvent flow channel.

The phase "pre-packaged disposable reagent cartridge" refers to an apparatus designed to fit removably and interchangeably into or onto an automated system described herein. The reagent(s) held within the cartridge, after fitting the cartridge into the system described herein, can be conveyed to the reaction chamber. When appropriate for the preparation of a radiolabeled compound, the reagent cartridge may contain solvents as well as reagents. Alternately, solvents may be provided separately from the reagents.

In one embodiment, automated systems disclosed herein include those which comprise a disposable reagent cartridge. In one embodiment, the present invention relates to an automated system with the flexibility to make a variety of different radiopharmaceuticals with minimal risk of cross-contamination, by simply changing the cartridge. Using such a cartridge has a number of advantages including simplified set-up, rapid change between production runs, pre-run automated diagnostic checking of the cartridge and reagents, reagent traceability, single-use, tamper and abuse resistance. Substitution of a reagent cartridge eliminates the need to design an entirely new automated synthetic system each time a different radiopharmaceutical is to be prepared. The system described herein allows cartridge exchange without opening the shield and exposing the user to radiation.

Suitable heat sources for use in the synthetic systems disclosed herein include, but are not limited to, resistive heating, localized and non-localized microwave heating and Peltier devices. Various sensors (e.g., flow sensors, liquid-gas interface sensors, radioactivity sensors, pressure sensors, temperature sensors, and the like) and other apparatus components (e.g., valves, switches, etc.) can be integrated into the system and connected to a computer for process control and monitoring purposes.

The synthetic systems disclosed herein comprise a microfluidic synthesis chip in which, for example, reagents are mixed and heated, solvents are exchanged, to carry out the desired chemical process.

Previous generation microfluidic chips were often too slow in operation (even conceptually) to be realized in a practical application. Embodiments of the present invention enable fast synthesis at the same time increasing the reaction yield which can be critical to low yielding biomarker production. Previously known microfluidic chips had to be operated manually or semi-manually, thus making them impractical for real applications despite the advantages demonstrated on-chip. As a result, automated instruments were previously employed using non-microfluidics methods. In one aspect, the present invention is directed to a self-shielded fully-automated radiosynthesis instrument based on a batch-mode microfluidic device.

Microfluidic devices as described herein when used for radiochemical synthesis allow known biomarkers to be made with higher speed and yield. Additionally, such devices enable production of new biomarkers that cannot be synthesized efficiently by conventional methods; for example; in research and development efforts in developing new biomarkers that typically involve sluggish reactions and/or reactions that cannot yield meaningful amount of material by conventional methods. Accordingly, an instrument allowing 10-20 syntheses to be performed in one day (vs. 1-2 with conventional equipment) enables the researchers to perform rapid optimizations of reaction conditions.

The various embodiments of the present invention describe fully automated radiosynthesis (e.g. from target water to purified product in an injectable formulation) to take place in a single instrument run in a fully automated (e.g., one touch) manner, or allowing individual step control. The various example embodiments disclosed herein can be used for either production of known biomarkers in an automated mode, as well as for development of new biomarkers in a mode with individual step control.

The systems disclosed herein have demonstrated significant yield and reaction time improvements, particularly over conventional chemistry. One exemplary system automates the chip operation through a Visual Basic program and PLC (Programmable Logic Controller). The automation process also provides automated product isolation capability.

Previously closed microfluidic reactors have relied on gas-permeable gaskets to contain the fluoride and reaction intermediates within the reaction chamber. These gaskets must be comprised of material that is inert enough to withstand the radiolabelling conditions, and at the same time, exhibit significant gas permeability. Once a suitable gasket is obtained, such closed devices, which rely on gas transfer across the membrane, still suffer from long evaporation times and filling steps. Meanwhile, one of the requirements of an efficient radiosynthesis is often speed. Generally, in previously disclosed micro-reactors, the intermediate (handling) steps, rather than the reactions themselves, have been found to be the major source of delays. In accordance with the various embodiments of the present invention, these reaction steps are minimized in time since reaction efficiency and filling steps are significantly shortened by the unrestricted gas path that does not involve membranes.

The systems and devices disclosed herein manage to prevent reagents, products, and intermediates from escaping without requiring a membrane. Additionally, they preserve the capability to perform superheated reactions. Embodiments of the present invention further relate to a micro-reactor plumbed for reagent delivery and solvent vapor removal. The reagent delivery in accordance with an example embodiment of the present invention may be enabled by channels with specially designed valves that do not rely on an elastomeric gasket and can withstand much higher pressures than previous systems. Devices produced in accordance with example embodiments of the present invention have been shown to operate successfully with hundreds of psi. In one example embodiment, the vapor removal takes place by flowing nitrogen over the top of the liquid. This flow can be effected in a controlled fashion, thus determining the rate of evaporation or allowing complete blockage during the reaction steps.

Accordingly, in accordance with the embodiments of the present invention, loss of F-18 is avoided, reduced, or mitigated, when various mechanisms are employed for the production of F-18 labeled probes, such as for example, [F-18] FDG. In addition, the embodiments of the present invention provide the necessary capacity to increase the diversity of products. In several embodiments of the present invention, the disclosed chips and control systems thereof demonstrate improved capabilities, including, but not limited to, conducting reactions under significant pressure, active mixing, concentration of reagents, speed of heating and cooling, etc.

One embodiment of the present invention, is a device that includes an integrated ion exchange column. Integrating the ion exchange column overcomes the F-18 loss in transit from the ion exchange column to the chip. Generally, the column may be packed inside the barrel made in the chip and capped with PEEK or other inert material frits. This column can also be placed in the chip fluidic adapter base.

Another embodiment of the present invention is a device that includes on-chip integrated valves that control the gas (and vapor) flow. In one variation, the on-chip valves control liquid passages while gas-controlling valves are off-chip. In another variation, liquid-controlling valves and gas-controlling valves are both on-chip. Integrating the valves on-chip, allows better sealing of the reactor as well as better pressure control. It also prevents solvent and reagent loss into extended off-chip vent tubing. Accordingly, the valve plungers may come right up to the reaction chamber, eliminating the channels between the valves and the reaction chamber, and thus allowing a closed system with no plumbing extensions. In one embodiment, these valves are configured to carry out reactions at high pressures. Other mechanisms assuring high pressure capability may be employed to reach or exceed 300 psi. Such capacity also allows superheated reactions, which in turn leads to higher yields and reaction rates guided by principles similar to microwave reactors.

In accordance with an embodiment of the present invention, a version of a reactor with no plumbing extensions may be constructed, which it is completely closed, and has a regular coin or other shape without any pockets where unreacted materials or uneluted products may stay. In addition to having a regular shape, the reactor surfaces may be made very smooth to minimize surface area. Additionally the corners and trenches may be eliminated to reduce the portions of the reactor that can collect reaction residue or moisture and that are difficult to access.

In another embodiment of the present invention, for reactors that can, for example remain sealed at high pressure, microwave capacity is incorporated onto the chip. Focusing microwaves on the reactor can lead to very fast reactions, as is known to those of skill in the art. Additionally, another variation incorporates built-in sonic equipment onto the chip to facilitate reactions by rapid mixing of reagents. In another variation a surface acoustic wave is used to facilitate mixing in the reaction chamber. In yet another embodiment, capillary channels that can aspirate the liquid and release it back into the reaction chamber in a form of a jet are used to mix the reagents.

Another embodiment of the present invention provides an improvement in the speed of heating and cooling, using a fast-responding temperature controlling system. In one aspect, the heating element is integrated on-chip. Another approach is an integrated radiator in close proximity to the reactor that carries a heat transfer "coolant"-like fluid, the temperature of which is controlled off-chip or in another portion of the chip. Generally, it can take some time for the heating block to equilibrate in temperature (e.g., a minute or more) and it can take longer for the reactor separated from the block by 1 mm of material to reach the same temperature. As disclosed herein, remote heating may also be achieved with a laser positioned externally but focused in the reactor. Additionally, or alternatively, the reactor floor thickness may be reduced, for example, to 250 µm to allow for faster and more efficient heat transfer.

For the increased speed of heating and cooling disclosed herein, chip materials may be employed that have better thermal conductivity than pure DCPD (polydicyclopentadiene). Such materials, for example, include DCPD doped with other materials. Another approach to address increased speed of heating/cooling involves thermal insulation of the reactor from the rest of the chip. In this case, the heating and cooling is not slowed down by the mass of the device acting as a heat sink.

In one embodiment, the material for the chip is glass. Alternately, similar materials such as quartz or silicon may be employed. Other appropriate materials can be identified by one of skill in the art. Analogously, appropriate methods of fabrication should be incorporated based on the use of such materials. In another embodiment, a chip, as disclosed herein, incorporates the capability to pre-package the reagents on-chip, which provides a single-use configuration. In a single-use configuration, the instrument may not conduct any liquid handling, avoiding waste of reagents. The on-chip reagents may be moved via membranes or pulled into the reactor by vacuum. In one system, prior to insertion of the chip into the instrument, all the valves of the chip are closed, holding the reagents in their individual reservoirs.

In another embodiment, the HPLC column/system is made part of the chip or the fluidic base adapter. When this purification system is part of the fluidic base adaptor, the column can be a multi-use component. Incorporating the various approaches described herein can reduce the loss of F-18 to non-significant values.

In another variation disclosed herein, is a flow-through reactor. Flow-through reactors include the traditional type based on tubing or a long serpentine in-chip channel, or a completely different architecture. Such possibilities include but are not limited to the cylindrical reactor similar to that reported by Gillies, et. al. "Microfluidic technology for PET radiochemistry" Applied Radiation and Isotopes (2006) 64:333-336, and Gillies et al. "Microfluidic reactor for the radiosynthesis of PET radiotracers" Applied Radiation and Isotopes (2006) 64:325-332. Additional novelties can be added to either type of the reactor to increase the reaction rates, as known to those of skill in the art. These additions may include, but are not limited to, certain geometries on the surfaces of the channels or reactors that introduce turbulence into the moving liquid or simply direct the flow. A principle of jetting one fluid into another may also be used.

It is also possible, as disclosed herein, to create a hybrid batch-flow reactor where a first liquid is circulated in a low-volume loop that keeps coming around. At one point in the loop, the first liquid comes in contact with a second liquid which is a flow-through reagent. The first and second liquid contact each other in a laminar flow mode, and subsequently, separate after a certain distance. This approach enables the key reagents and intermediates to be maintained in a concentrated solution that does not leave the chip, while other (cheap and non-limiting) reagents are flowed through. It is also possible to incorporate such mechanism for the trapping of fluoride, where it is transferred from a dilute flowing solution into a concentrated re-circulating solution. A similar principle may be applied during some or all of the purification stages. Alternatively, other active mixing mechanisms can be created in either flow-through or static batch reactors.

Another semi-batch approach is based on the "Hypervap" technology in accordance with an example embodiment of the present invention. The Hypervap allows the reagents to be continuously infused into the reactor where they are being concentrated. From the single concentration solution, a desired amount of reagent is brought into the reactor by varying the reagent and gas flow. That particular reagent remains in the reactor in the same volume (which can also be controlled). Here, the reactions take place in one chamber in a solution moving rapidly around the chamber. While the product can be collected only once per run as a batch, the amounts of reagents used can be varied during the run. This approach can bring value to both research and development as well as production applications.

In another variation described herein, additional beneficial features are provided to address issues such as extended material transfers, limited solvent exchange capability and inefficient F-18 trapping and release. The chips, in accordance with example embodiments of the present invention, enable efficient concentration of dilute solutions. These advantages are partly due to the fact that losses associated with material transfers are reduced in integrated devices in accordance with embodiments of the present invention. Incorporation of trapping and release system, which, for example, can function at about 99% efficiency or greater, and raise the overall yields observed on a number of disclosed systems. This efficiency is achieved by several factors. First, the volume of the ion-exchange bed (e.g., packed with AG1-X8 or another resin) is minimal (e.g., 4 uL total volume and less than 2 uL void volume)—this leads to a 15 microliter elution containing multiple column-volumes of eluent. Second, the trapping and release of fluoride take place in opposite directions—most of F-18 is concentrated at the beginning of the column during trapping and does not have to equilibrate with the rest of the column during the release. Third, the release solution is broken down into small fractions (e.g., of about 1 uL or less)—this allows the most concentrated F-18 to travel in the first few fractions without mixing with the rest, allowing each subsequent fraction to mop up what is left behind after the previous one with a fresh batch of eluent rather than with a concentrated F-18 solution. Overall trapping and release efficiencies of up to 99.8% has been observed. When using an ion exchange column, the choice of frits can be very important. For example, metal frits may negatively affect the trapping and release, Teflon frits may degrade easily, and PEEK frits may get clogged up easily despite solution filtration. In accordance to one example embodiment of the present invention, UHMW PE (ultra high molecular weight polyethylene has been determined to be an optimal frit material. Electrochemical trapping and release mechanisms incorporated herein, and in some embodiments of flow-through modes, are very beneficial. In other embodiments the elution volume can be smaller, such as 10 uL, 5 uL or 2 uL.

For both the flow-through and batch devices, optimized devices are prepared using highly inert and high tech materials. Such materials can include, but are not limited to PFPE-based materials (perfluoropolyether) or experimental ROMP. In another embodiment of the present invention, devices enabling performance of multiple reactions on the same chip, including reactions run at the same time when different regions of the chip are used, are disclosed.

A number of novel biomarkers involve more complex syntheses with intermediate purifications. To accommodate such routes, a device in accordance with an example embodiment of the present invention is designed with a fast active concentration mechanisms allowing HPLC purifications of intermediates. Such a device may also contain multiple reactors with different volumes or features suited for the different steps of the process. One advantage to such a system is that everything is integrated into one device, thereby minimizing material transfers and eliminating the need for dilutions. Concentration devices relying on principles similar to Hypervap may allow continuous concentration of solutions, where a solution is being fed into a small chamber as the solvent is being evaporated. Alternately, large containers/chambers may be designed on-chip, but in such an example, after evaporation, it may be difficult to collect the material off the walls with high surface area.

In one example embodiment, a device/instrument combo is provided that enables the performance of multiple reactions at the same time. In such a configuration, several batches may combine product at purification stage. Alternately, several batches may be staggered to allow sequential runs of the purifications on the same column with reaction mixtures originating from different reactors.

In one variation, polymers such as pDCPD, a rigid, transparent polymer with good machining properties, are used in the devices disclosed herein. Furthermore, employing alternate methods of fabrication leads to faster production and better chip properties. Such methods may include, but are not limited to, hot embossing, injection molding or etching. It is also possible to incorporate reactions on solid supports, where either the non-radioactive reagents are immobilized, or the molecule being labeled (followed by cleaving after purification).

The instrument controlling the chips disclosed herein may be self shielded and capable of receiving the labeled probe via either tubing or a vial. In the latter case, the vial may be shielded and plugged into the instrument without exposure to the operator.

In one example embodiment, each reagent and/or solvent may be delivered to the synthesis chip from an individual reagent/solvent source. In this case, each reagent/solvent source may have two ports into which tubing is inserted: an inlet and an outlet. The inlet tubing may sit above the fluid surface and in fluid communication with an electronically controlled 3-way valve connected to a pressurized or metered inert gas supply (e.g. nitrogen or argon). Each reagent/solvent may have its own individually-controllable pressure to allow flexibility by allowing different flow rates. The outlet line (or outlet channel) of each reagent/solvent source can be a piece of tubing with one end at the bottom of the reagent vial and heading toward the microfluidic chip. The 3-way valve connected to the inlet can be opened such that the reagent/solvent vial is pressurized and the reagent/solvent is pushed into the outlet line, or it can be vented such that the reagent/solvent vial is open to atmosphere and depressurized.

The lines (or channels) from reagent/solvent vials may pass through an additional electronically-controlled 3-way valve on the way to the synthesis chip so that a "wash" solvent and/or inert gas (nitrogen or argon) can be directed toward the synthesis chip to clean and dry one or more lines at the end of a synthesis run. Drying the lines helps to avoid liquid leaks when removing and reinstalling the chip from the interface adapter. Drying also helps avoid contamination of subsequent runs with previously run components or dilution of reagents by cleaning solvents. In addition, check valves are placed in the inlet lines on the way to the synthesis chip to ensure no back flow into a reagent/solvent vial should there be any leaky microfluidic chip valves (or valves switched inadvertently at an incorrect time).

Figure 28:
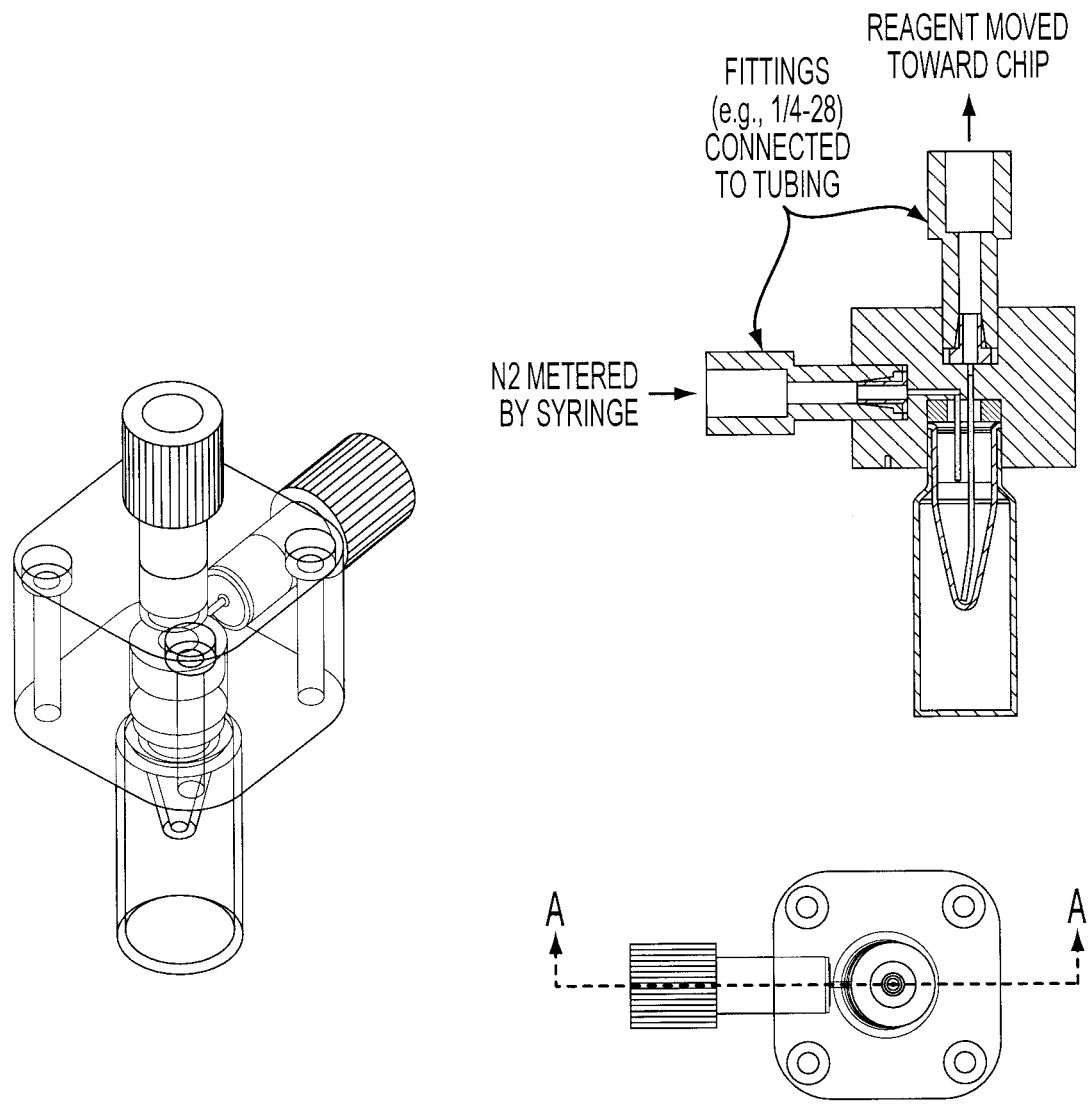
FIG. 28 illustrates a vial fixture in accordance with an exemplary embodiment of the present invention.

In one embodiment the reagents/solvents are loaded individually in pre-filled vials into the system. These vials, for example, may be small v-vials that are positioned between the syringes that move $N_2$ and the chip, and can be filled with reagents that are used in their entire volume on the chip in a single run. The fixtures that hold these vials may have a pin that reaches to the very bottom of a v-vial and is connected to tubing leading to the chip. Another port in the fixture that holds a vial may be connected to the $N_2$ syringe that can move the liquid into the chip in a controlled manner by pushing $N_2$. The reagents used in ng or mg quantities can be weighed out in these vials followed by addition of solvent with a micropipette. FIG. 28 illustrates the geometry of such a vial in accordance to an example embodiment of the present invention. The "zero-waste" reagent vial depicted in FIG. 28 may be utilized for precursor and Kryptofix2.2.2 solutions loaded into the system in precise amounts. There are two ways to deliver reagents to the chip from such vials. One is by opening an on-chip inlet valve and a vent (for the escape of displaced gas) and gently moving $N_2$ with a syringe behind the reagent. The other method eliminates the use of a syringe. With an on-chip valve open and vent closed, a small amount of pressure is applied behind the liquid in the v-vial to push it towards the chip as the gas in the system compresses. As the pressure is increased, the gas in front of the liquid is further compressed, causing the liquid to move towards the chip, and eventually reaching and filling the reaction chamber. This latter method may only be used when off-chip vent valves are used.

In another embodiment, these reagents/solvents can be packaged into single reagent cartridges that can be installed in one step, or may be packaged in tiny quantities with each synthesis chip to easily allow the synthesis of different biomarkers. A different set of reagents/solvents and different chip configuration may then be used for each desired radiosynthesis. Alternatively, if the same reagents are used in subsequent runs (such as HCl), they can be loaded into the system in large volumes and metered amounts can be dispensed to the chip, when necessary, by syringe pumps. In another embodiment the chip incorporates a metering mechanism that allows only a certain amount of reagent used in excess to be used in a single run. Such mechanism may be based on surface tension or other properties.

In one exemplary system, the radiolabel, such as F-18, is delivered from a cyclotron through a check valve and into a temporary storage vial inside the instrument. In a another exemplary system, the radiolabel is delivered each day in an easy-to-connect leaded-vial or possibly in the solid-phase (e.g. attached to an ion-exchange column to be eluted into a temporary storage vial inside the instrument). It is not anticipated that operators will have their own cyclotron and delivery as necessary, e.g. daily, of the radioactive label addresses this deficiency. In one example of [F-18]FDG synthesis, F-18 is provided in a solution of target water: the solution is first passed through an exchange resin to trap and concentrate F-18; the F-18 is then eluted into the microfluidic synthesis chip using a $K_2CO_3$ solution. To minimize the fluid volume transferred from the exchange column to the microfluidic synthesis chip, an ultra-low volume (e.g., 0.5 µL) rotary valve may be used in this part of the fluidic system.

In one embodiment the entire load of radionuclide delivered to the system (from a cyclotron or a shielded container) is used in a single run, while in another embodiment it can be separated into fractions that are used in several sequential or parallel runs.

Other methods of trapping fluoride ion (e.g. electrochemical trapping, such as is disclosed in U.S. Ser. No. 60/950,976 "Microfluidic Radiosynthesis device relying on electrochemical trapping and release of F-18 in its isotope concentration step") can alternatively be easily integrated into the systems in accordance with embodiments of the present invention. With electrochemical trapping, the controller, and by extension the computer can additionally control the high voltage supply necessary in this setup.

The radiolabeled product made in the synthesis chip may be eluted with solvent through a purification system, such as, for example, a column, and into the final collection vial (or product receptacle) and may be diluted to the volume required for analysis and/or injection into the patient. In one embodiment, the product receptacle is located in a leaded vial or syringe affixed to the outside of the instrument for easy and quick removal and delivery to the patient or for further analysis. Alternatively, the product can be eluted into an injection loop, from which it is loaded onto an HPLC column and can then undergo HPLC purification.

An additional electronically-controlled 3-way valve may be placed in the pathway of a solvent, such as water, to the microfluidic synthesis chip. In one position, this valve may allow solvent to flow into the synthesis chip. In the other configuration, it may allow liquid to come from the synthesis chip and flow to waste. This valve may be used during the wash/clean phase. Wash solvents and gas (nitrogen or argon) may be flowed through the synthesis chip to drain and clean it. In one embodiment, the entire system can be washed with solvent without disassembling the system and without removing the shielding.

The automated system in accordance with an embodiment of the present invention also controls the valves integrated in the microfluidic chip. Pneumatic pistons that drive the mechanical actuating pins in these valves are driven by compressed air (or another gas) that is controlled by electronic valves on demand.

A number of synthesizers known in the art employ gas pressure actuated elastomeric valves or pneumatic valves. In addition, there is significant literature disclosing the control of microfluidic valves by various methods of actuation. See for example, U.S. 2002/0127736 "Microfluidic devices and methods of use," incorporated herein in its entirety by reference. In one aspect, the microfluidic devices in accordance with embodiments of the present invention employ mechanical valves (such as those disclosed in U.S. Patent Publication No. 2007/0051412, incorporated herein in its entirety by reference) that are capable of operating efficiently under high pressures.

Details of a microfluidic chip, and reagent delivery via a dead-volume bypass mechanism which can be incorporated into the presently disclosed system are discussed in U.S. Ser. No. 11/862,167 "System and Method for Interfacing with a Microfluidic Chip," incorporated herein in its entirety by reference.

The bypass portion of each inlet may be connected to a check valve then to a single electronically-controlled dead-volume bypass valve. In one embodiment, system components that can be under automatic control include an inert gas delivery source, a temperature control system, a pressure control system and one or more valves on the synthesis chip.

The hardware disclosed herein can be controlled using various electronic hardware instrumentations and devices. For example, a PC-104 based system may be used with 16 analog inputs, 10 analog outputs, 8 digital inputs, and 48 digital outputs. The controller can run, for example, embedded Windows-NT software that communicates via an Ethernet connection to a standard PC running the FIX32 automation software, an automation language that allows simple construction of graphical interfaces to visualize what is happening in the hardware and to control the various valves and other components. The interface may allow various modes of operation such as fully-automated, manual, or step-wise operations.

In one embodiment, the control software may access individual digital outputs (e.g., 2-way and 3-way valves, on-chip valves, temperature control system, heater enable, cooler enable, vacuum system, rotary injector, and other system components) and analog outputs (e.g., temperature set point, and other outputs). Analog inputs (e.g., reactor temperature, vent channel pressure, radiation levels) may be scaled to engineering units for monitoring on the main screen.

In addition to the interactive graphical interface described herein, dozens of scripts automate the process steps described herein. Each subprogram may perform a sequence of simple operations such as changing the state of a valve, waiting for a fixed amount of time, or waiting for particular value of an input (e.g. heating until the reactor reaches a specified temperature). The system in accordance with embodiments of present invention is capable of repeatably producing purified human-scale amounts of FDG, for example, in a semi-automated (each step in the radio-synthesis is initiated with a button on the computer screen) fashion.

In a fully-automated system, the needed reaction times may be optimized, and a simple script, for example, in FIX32, may be written to execute all the operations in sequence. A working example may involve automated unit operations, such as filling, which in turn involve multiple sub-steps. The "unit operation" scripts may be designed to be "parameterized". That is, in a single place, an operator may set the flow times, reaction times, and heating temperatures. The automated script may then read all the information and adjusts the synthesis run accordingly. The automated operation may be also be initiated, for example, by a simple user click on a 'start' icon that is part of the user interface. The systems in accordance with embodiments of the present invention provide a fully automated hands free operation of the entire radio-synthesis cycle on a microfluidic device yielding purified PET radiotracer. In one embodiment, the instrument is portable, has no external components and is self-shielded, that is, it does not require a separate hot cell. In yet another embodiment, the instrument comprises internal filters which enable operation without any additional exhaust, i.e. a true tabletop operation that doesn't require a fumehood.

In accordance with an exemplary embodiment of the present invention, the hardware disclosed herein may be controlled using a PC, a Programmable Logic Controller (PLC), and a Software control program written in Visual Basic. The PLC may control all of the I/O in the instrument using 6 analog outputs, 8 analog inputs, 24 relay outputs, 18 digital inputs, 17 digital outputs, and a Ladder Logic program. The standard PC, using, for example, a Visual Basic control software, may control the PLC and 8 precision syringe pumps using serial communication. This provides a very detailed graphical interface allowing visualization of what is happening in the hardware, and controlling the various valves, pumps, heaters and other components. The interface may also allow various modes of operation such as fully-automated, semi-automated, and manual.

In accordance with an example embodiment, in the Manual mode of operation, the control software may allow individual control of all of the components and processes in the instrument through button clicks and text input from the User Interface screen.

In accordance with an example embodiment, in the Semi-Automated mode of operation, various subroutines adapted for automated control of various processes such as, Initializing, Priming, Filling, Evaporation, Hydrolysis, Fluorination, and others may be used. Also, each of the automated steps may allow for particular values of input (e.g. temperature, pressure, flow rate, volume, and time).

In accordance with an example embodiment, in the fully-automated mode of operation, the systems provide a fully automated hands free operation of the entire radio-synthesis cycle on a microfluidic device yielding purified PET radiotracer products, with the click of a single button. The needed reaction values may be input at the start of the reaction, if desired. That is, the default values may be changed, and an operator may set the flow times, reaction times, temperatures, pressures and volumes before starting the reaction. The automated script may then read all the information and adjust the synthesis run accordingly. In one embodiment, the instrument is portable, has no external components and is self-shielded (that is, it does not require a separate hot cell). In yet another embodiment, the instrument comprises internal filters which enable operation without any additional exhaust, i.e. a true tabletop operation that doesn't require a fumehood.

In one embodiment, one or more reagents can be delivered from pre-filled individual vials or from a pre-packaged disposable cartridge. In one embodiment, the portable system can be cleaned without disassembly. Accordingly, the reaction chamber, and each of the reagent, product and waste channels can be cleaned, optionally in an automatic manner. The identity of the radiotracer produced can be easily changed without requiring hardware modifications. In one embodiment, the microfluidic synthesis chip can be exchanged. In one variation, the exchange of the synthesis chip can be performed by opening a single door in the lead shield, as opposed to disassembling the whole shield. In another embodiment, the final product vial may be located in a separate shielded container so that the operator taking the product is not exposed to the rest of the radiation from the instrument.

Radiation shielding: Integrated shielding is one feature that makes the instruments disclosed herein independent from traditional hot cells and radiopharmacies. In one embodiment, shielding consists of a box built from 18 interlocking 0.565"-thick lead panels (2000 lb total). In accordance with another example embodiment of the present invention, shielding of the device is effected in a localized fashion. Thus, as opposed to encapsulating the entire device, which increases the device weight and exposes the electronics to radiation, localized shielding may be implemented to cover only the radiation-handling components and detectors, such as the ion exchange column, the chip, and the F-18 source vial. This arrangement uses significantly less shielding material while maintaining protection for the electronic components. Alternately, the instrument may be designed of such a size that it can fit inside an appropriately shielded mini-cell, if desired. Some of the advantages associated with such localized shielding can be summarized as follows:

- A portable and light instrument (~300 lb);
- No required lab buildout with hot cells;
- Protection of electronics from radiation damage;
- A "plug-in" pig that allows placement of the instrument away from the cyclotron;
- Transportation of instrument without user exposure;
- Isolation of detectors from the rest of the system by using a compartmentalized design, which also allows the removal of product without exposing the user to other sources of radiation inside the instrument;
- Ability to conduct multiple consecutive runs without the need to open the shield since reagent vials may be placed outside of the shielding,
- Easy hatching mechanism on top that allows access to the inner (shielded) area without the need for excessive force (to lift the heavy shield) since the segments are on rails that slide easily; and
- Shielding that is uniform, providing protection from all angles.

In another embodiment, the instrument includes a heat-exchanger that allows rapid heating of the reaction chamber by a resistive heater and cooling of the reaction chamber by air in a vortex cooler.

According to one embodiment of the invention a computer system, or external input device, may be coupled to a program storage device and to a controller. The controller may be coupled to at least one valve on the synthesis chip, an inert gas delivery source, a temperature control system, a pressure monitor, and/or a vacuum system.

The general computer system includes a processing device, a system memory, a system bus coupling the system memory to the processing device, a storage device, such as a hard disk drive, a magnetic disk drive, e.g., to read from or write to a removable magnetic disk, and an optical disk drive, e.g., for reading a CD-ROM disk or to read from or write to other optical media. The storage device may be connected to the system bus by a storage device interface, such as a hard disk drive interface, a magnetic disk drive interface and an optical drive interface. Although this description of computer-readable media refers to a hard disk, a removable magnetic disk and a CD-ROM disk, it should be appreciated that other types of media that are readable by a computer system and that are suitable to the desired end purpose may be used, such as magnetic cassettes, flash memory cards, digital video disks, etc.

A user may enter commands and information into the general computer system or enter graphical information into the general computer system. A display device, such as a monitor, having a display screen, is connected to the system bus via an interface. In addition to the display screen, the general computer system can also include other peripheral output devices. The general computer system can operate in a networked environment using logical connections to one or more remote computer systems, such as a server, a router, a peer device or other common network node, and such a system can include any or all of the elements described relative to the general computer system.

When used in a local area network (LAN) environment, the general computer system is connected to the LAN through a network interface. When used in a WAN networking environment, the general computer system typically includes a modem or other means for establishing communications over a WAN, such as the Internet. The modem, which may be internal or external, may be connected to the system bus via the serial port interface. In a networked environment, program modules depicted relative to the general computer system, or portions thereof, may be stored in the remote memory storage device. It should be appreciated that the network connections shown are exemplary and other means of establishing a communications link between the computer systems may be used. It should also be appreciated that the application module could equivalently be implemented on host or server computer systems other than general computer systems, and could equivalently be transmitted to the host computer system by means other than a CD-ROM, for example, by way of the network connection interface. Program modules stored in the drivers of the computer system may control how the general computer system functions and interacts with the user, with I/O devices or with other computers. Program modules may include routines, operating systems, target application program modules, data structures, browsers, and other components.

It should be appreciated that no particular programming language is described for carrying out the various procedures described in the detailed description because it is considered that the operations, steps, and procedures described herein are sufficiently disclosed to permit one of ordinary skill in the art to practice an exemplary embodiment of the present invention. Moreover, there are many computers and operating systems which may be used in practicing an exemplary embodiment, and therefore no detailed computer program could be provided which would be applicable to all of these many different systems. Each user of a particular computer should be aware of the language and tools which are most useful for that user's needs and purposes.

Moreover, the method may be embodied in the form of computer-implemented processes and apparatuses for practicing those processes. The above may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing embodiments of the invention. Existing systems having reprogrammable storage (e.g., flash memory) can be updated to implement embodiments of the present invention. The above can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing embodiments of the present invention. When implemented on a general-purpose microprocessor, the computer program code segments may configure the microprocessor to create specific logic circuits in whole or in part.

Example Embodiment

Design of a Chip

FIG. 1 illustrates a microfluidic chip in accordance to an exemplary embodiment of the present invention. The exemplary reactor 10 depicted in FIG. 1 is located in the middle of the chip 90 and has a cylindrical shape, with dimensions: 5 mm wide and 3 mm tall. While this results in a reactor volume of 60 μL, it may be advantageous not to fill the reactor to maximum capacity as it may lead to loss of solution into the vents and outlets. For example, using 30-45 μL of solution may provide a suitable amount for proper operation. When the reactor is partially filled, there is enough space above the liquid to allow constant flow of nitrogen that carries the vapors off the chip.

The reactor 10 is fixed in the middle of the chip 90 and in fluid communication with the reactor one or more inlets 20. As illustrated in FIG. 1, the chip may contain an o-ring 30 in physical contact with both the top 95, and the bottom 99 of the chip. Venting from the reactor 10 is accomplished via a vent channel 40, which is controlled by the valve plunger 50, which is further in fluid communication with vent outlet 60. The reagents are added to the reactor 10 via the reagent inlet 70, which is controlled by the valve plunger 55, which is in fluid communication with the reagent by-pass outlet 65. Arranged below the reactor is the heater (not shown) located at the heater opening 80.

Valves: In an example embodiment of the present invention, the reactor is plumbed with 6 flow channels. Four of the flow channels deliver reagents and two serve to elute product. Since there is no membrane used as a seal, valves are designed for use with this chip. The valve plungers entering the chip through the sides create the seals inside the barrels in which they travel. These seals may be created by a soft inert material at the tips of the plungers, such as for example Teflon; other appropriate materials are known to those of skill in the art. When the valve is in the closed position, the plunger is inserted all the way in and pressed against a hard stop near the reactor. Reagent delivery is made possible by a vertical channel that crosses the valve barrel. In the "valve closed" configuration, the reagent is delivered through the top of the chip. The thinner part of the plunger tip allows the reagent (as well as the air/gas pushed by the reagent out of the tubing during filling) to exit through the bottom of the chip. When the plunger is retracted, the inlet has a clear pass to the reactor. It is necessary to close an external valve on the outlet to prevent the reagent from continuing to escape while filling the reactor.

In an alternative example embodiment the external valve is optional. This design has the reagent inlet and outlet staggered along the barrel in such a way that when the plunger is retracted to a certain position, only the inlet gets a clear passage to the reactor while the outlet gets blocked. Further details of the exemplary valves in accordance with embodiments of the present invention are provided herein.

Heater: In one exemplary embodiment, heat may be transferred to the reactor from a Peltier, or similar, device through an aluminum block inserted into the cylindrical opening directly below the reactor. Such arrangement allows for rapid heating and cooling of the reactor contents.

Figure 2A:
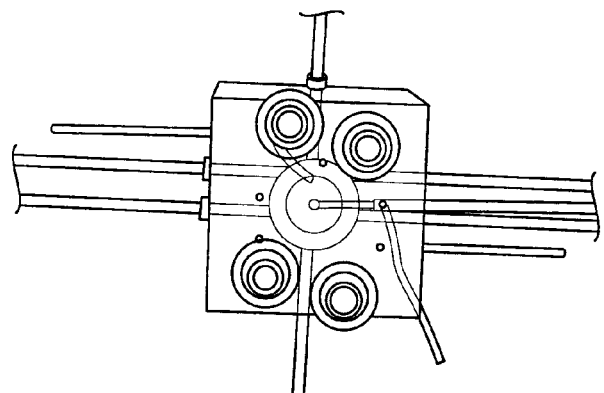
FIG. 2 illustrates different view angles of an assembled exemplary microfluidic chip in accordance with an embodiment of the present invention.
Figure 2B:
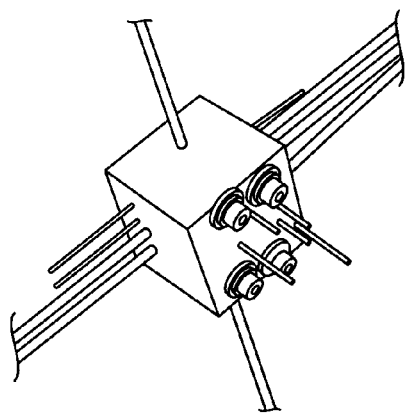
Figure 2C:
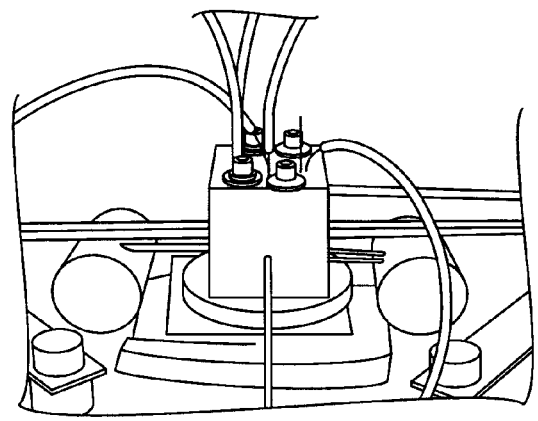

Parts. The chip comprises two sections or parts that may be press-fitted together in such a fashion as to limit or eliminate leaks at their junction. In one exemplary embodiment, an o-ring may be placed at the interface of the two parts to eliminate the possibility of leaks. Radioactive tests have confirmed that little to no material made contact with this o-ring. Thus, in one example embodiment of the present invention, the o-ring may be omitted. The top part of the chip functions as a 'lid' to the reactor. When the lid is designed to be oversized, it allows the chip to be held together by screws. FIGS. 2(A) to 2(C) illustrate one such fully assembled chip from different viewing angles. It should be noted that while the exemplary embodiment of the present invention as illustrated in FIG. 1 comprises a single reactor, more than one reactor may be implemented in a single chip. Such implementation enables parallel operation of the reaction chambers, which may be utilized to conduct the same or different reactions.

Vent. The top of the reactor has two openings controlled by individual valves which serve as an inlet and an outlet for nitrogen. Flowing nitrogen over the solution in the reactor enables rapid evaporation of solvents even at ambient temperatures. Closing both vent channels makes the reactor function as a "sealed tube," allowing reactions to take place without solvent evaporation, and further allowing superheating of the reaction mixtures above the boiling points of corresponding solvents. In another embodiment, the reaction chamber may be pressurized to facilitate the reactions.

Example Embodiment

Use of Chip a for Preparation of $^{18}$F-FDG

Figure 3:
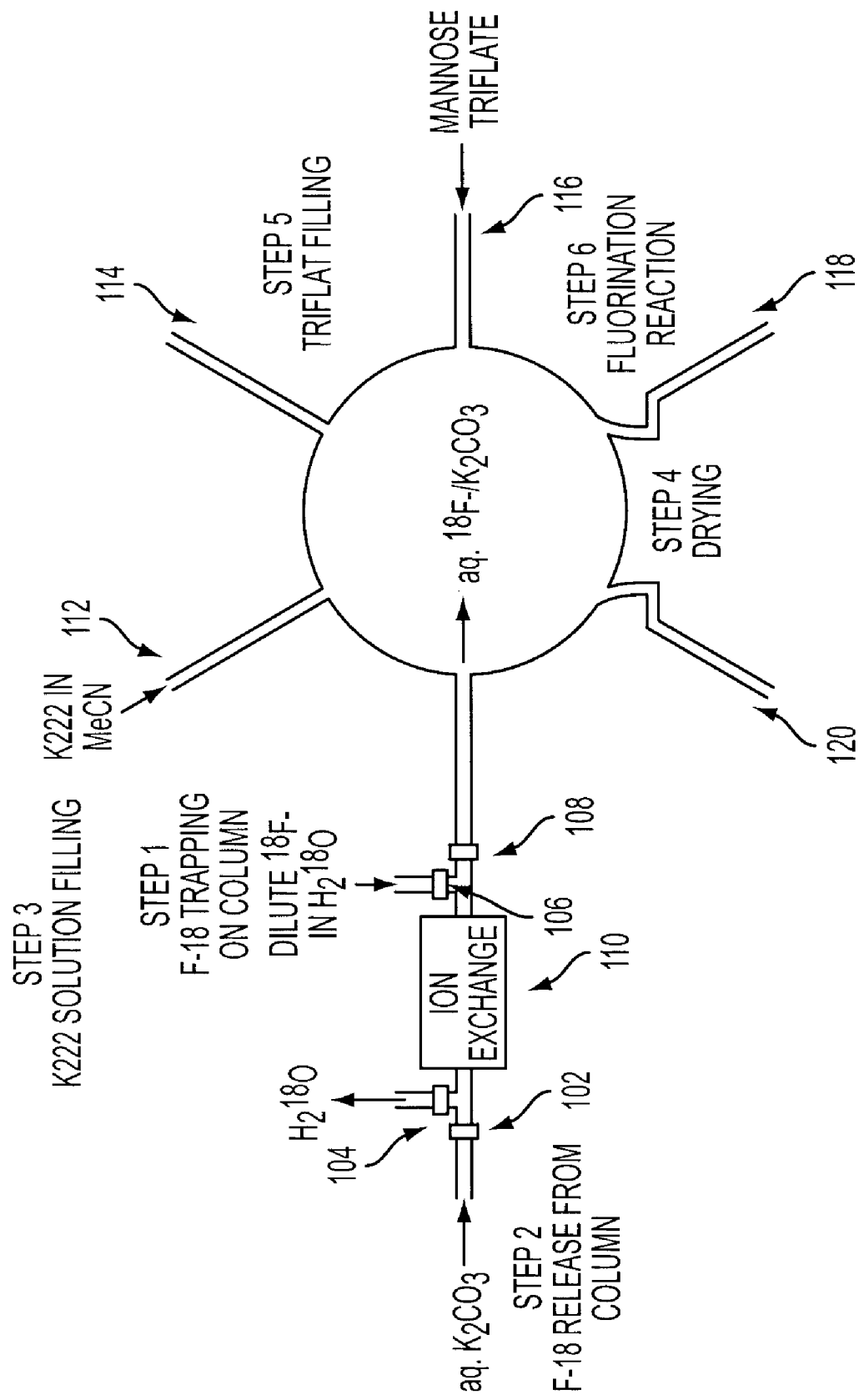
FIG. 3 illustrates exemplary steps for [F-18]-FDG synthesis in accordance with an embodiment of the present invention.

FIG. 3 outlines a series of example steps involved in the synthesis of [F-18]-FDG with the reactor such as the one described above. The device described herein allows evaporations to take place in seconds and the total run time is determined by the reactivity of the labeling precursors. By using the example device in accordance with the embodiments of the present invention, the total synthesis time for FDG has been demonstrated to be under 20 min after optimization.

In Step 1, with valves 102 and 108 closed and valves 104 and 106 open, the target water is passed through the ion exchange cartridge 110 to trap the F-18 out of a dilute solution. In Step 2, with valves 104 and 106 closed and valves 102 and 108 open, $K_2CO_3$ is released into a concentrated solution that enters the reactor. After that delivery has taken place, the valve 108 controlling the F-18 inlet closes, and in Step 3 K222/MeCN solution is delivered from channel 112. After the reagents have mixed, nitrogen starts flowing through the ports in the ceiling of the reactor (not shown in FIG. 3). In Step 4, solvents evaporate quickly leaving behind a residue containing [F-18]KF/K222 complex. The evaporation is generally efficient enough that there is no need for subsequent drying steps with acetonitrile (MeCN), which are common in conventional systems. In Step 5, the precursor (mannose triflate) is delivered to the reactor (at ambient temperature) through channel 116. The resulting reaction mixture is heated, allowing it to boil for a few seconds to achieve mixing and re-dissolve the residue. Afterwards, all the vents are closed and the reaction mixture is superheated to 140° C. After cooling, the solvent is evaporated by the flow of nitrogen. In step 6, deprotection is carried out by bringing ethanolic HCl into the reactor. Ethanol is one solvent that assists the dissolution of the hydrophobic residue in the acid. Once again, the reaction mixture is heated, then the solvents are evaporated leaving behind a residue of FDG. The final step of product elution (not shown in FIG. 3) takes place when water enters the reactor from one channel 118 and carries the products out of the other channel 120. Optimization studies, theoretical calculations and tests with the current chip have supported the theory that the elution is the most efficient when the eluent entrance and exit channels are located tangentially to the circumference of the reactor, but other configurations are possible.

Figure 4A:
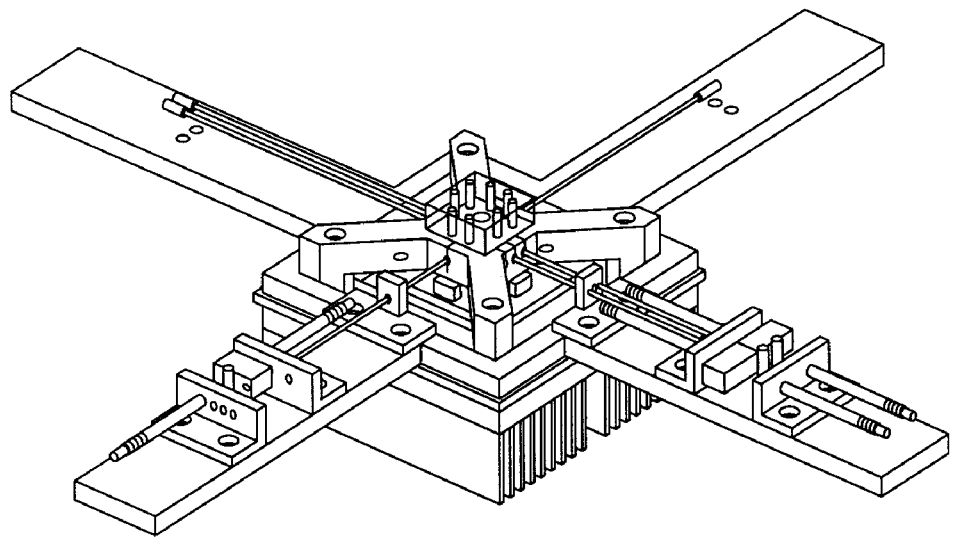
FIG. 4 illustrates an exemplary microfluidic chip with remote actuators in accordance with an embodiment of the present invention.
Figure 4B:
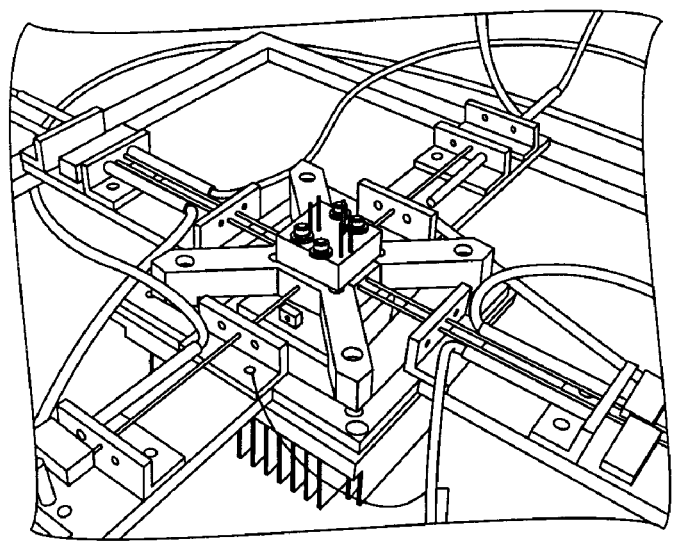

Remote operation: To be suitable for radiosynthesis, the device must be operated remotely to avoid exposing the operator to radioactivity. In one exemplary embodiment, the valve plungers may be moved manually, either during cold runs or test runs with trace levels of radioactivity. In an exemplary embodiment, actuators relying on pneumatic actuation may be constructed around the chip to allow manual but remote operation. FIG. 4(A) illustrates a drawing of an exemplary device with manual (but remote) pneumatic actuators. FIG. 4(B) illustrates an actual exemplary device in which the above noted actuators are utilized. In one configuration, pairs of pressure cylinders mounted on a rigid platform may drive the plungers in and out of the chip individually. This design requires only a single gas supply and a series of flip switches, which is relatively easy to implement. Alternatively dual direction air cylinders can be used to move a plunger back and forth.

The above-described chips have been used in successful preparations of [F-18]-FDG, demonstrating performance that is superior to previous generations and in some aspects surpasses conventional chemistry modules. Table 1 illustrates exemplary performance characteristics associated with the chips in [F-18]FDG radiosynthesis.

TABLE 1

Exemplary Chip Performance in [F-18]FDG Radiosynthesis

| Activity | Performance |
| --- | --- |
| F-18 uptake into acetonitrile | up to 95% |
| Fluorination yields | up to 97% |
| Hydrolysis | up to 94% |
| Overall use of F-18 | up to 82% |
| Overall output | up to 65%, FDG |
| "Clean" run time | to FTAG - 13 min |
|  | to FDG - 17 min |

During testing it became apparent that in an optimized system, some boiling of reagents can be used to facilitate the mixing of the components or to dissolve residues, while superheating is important for the reactions themselves.

F-18 concentration: In accordance with another example embodiment of the present invention, in addition to the chip, a trapping mechanism may be utilized to complement the chip operation. In this device, a small column (e.g., 1.5×5 mm), packed with AG 1-X8 resin is used to trap the [F-18] fluoride from 2 mL of dilute $H_2{}^{18}O$ solution and release it into a concentrated $K_2CO_3$ solution, transferring the entire load of activity in as little as 5 μL of solvent. This may be achieved by incremental elution. This principle relies on the F-18 gradient that takes place when $K_2CO_3$ is passed through the column carrying the most concentrated F-18 solution at its front. The diffusion of F-18 through the solution is so fast that this gradient is not apparent in regular settings, where F-18 can back propagate through the eluent and equilibrate in concentration in a matter of seconds. In this setup, F-18 is eluted with increments of 1 μL or less, separated by air so that the fluoride in the first fraction cannot propagate into the second one, and so on. Since over 90% of F-18 is contained in the first few fractions, most of F-18 can be moved into the reactor in accordance with the above technique. By making the column completely enclosed in PEEK (including the frits), additional losses of F-18 (such as observed using stainless steel frits) may be decreased or avoided.

Figure 5:
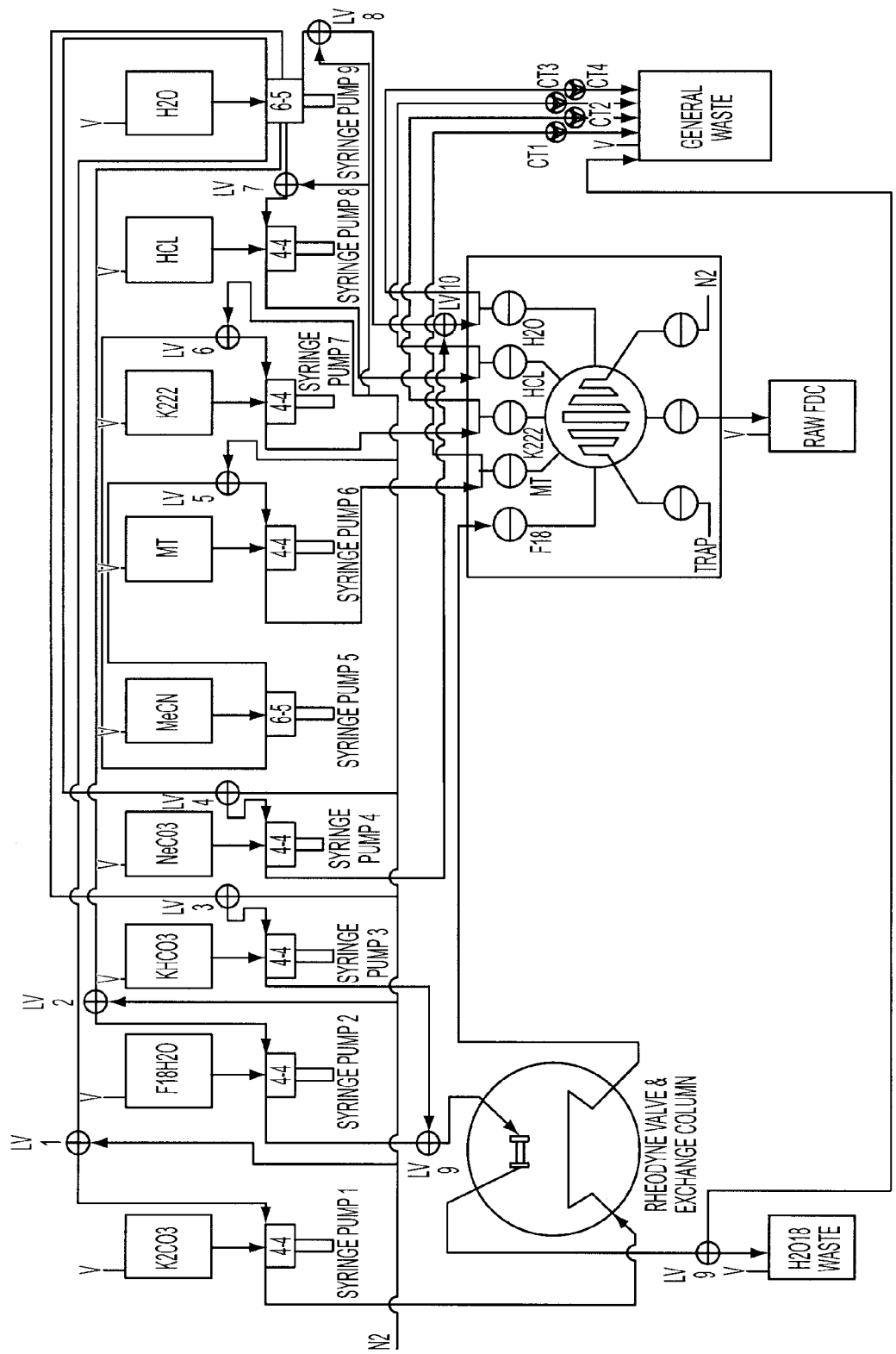
FIG. 5. illustrates a fluid and gas network for a microfluidic instrument in accordance with an exemplary embodiment of the present invention.

Instrumentation: To build an instrument around this chip, several aspects must be taken into consideration, including (a) automation and metering of reagent delivery, (b) automation of valve control, (c) heating with a feedback loop, and (d) automation of a stepwise process that is based on step completion rather than excessive step timing. A process of addressing the above noted issues may be accomplished in accordance with the exemplary flow scheme of reagent delivery shown in FIG. 5. FIG. 5 illustrates a series of vials containing $K_2CO_3$, $K^{18}F/H_2{}^{18}O$, $KHCO_3$, NaOH, MeCN, Mannose Triflate, Kryptofix2.2.2, HCl and $H_2O$. These vials are connected to syringe pumps 1-9. FIG. 5 further illustrates the delivery routes of the various reagents, as well as $H_2{}^{18}O$ waste, raw FDG, and general waste reservoirs in accordance with an example embodiment of the present invention. A more detailed description of the reagent flow and delivery mechanism, in accordance with an exemplary embodiment of the present invention, is described herein in connection with FIG. 14. Implementation of this scheme in an instrument allows priming of all reagents, delivery of reagents to the reactor, collection of products and running multiple reaction cycles intermittent with cleaning cycles.

In one embodiment, the chip disclosed herein does not have a membrane limiting the volume of the reactor, but rather the chip has an open vent. While such arrangement enables fast filling of the reactor, which is not restricted by the necessity to pass gasses across the membrane, the uncontrolled flow of liquid actuated pneumatically may lead to the loss of liquid into the vent. Therefore in one example embodiment, the pneumatic liquid actuation, which can create high pressures and lead to massive consumption of reagents and frequent failures, is replaced by a syringe driver-based system. The syringe-based system is capable of measuring the reagent amounts precisely with minimal waste, is fast, and does not create high pressures. Each reagent may have its own syringe driver that can be programmed to act at a certain time in the radiosynthesis process. FIG. 5 illustrates exemplary syringe pumps that are incorporated into the flow diagram of an exemplary embodiment of the present invention.

Figure 6:
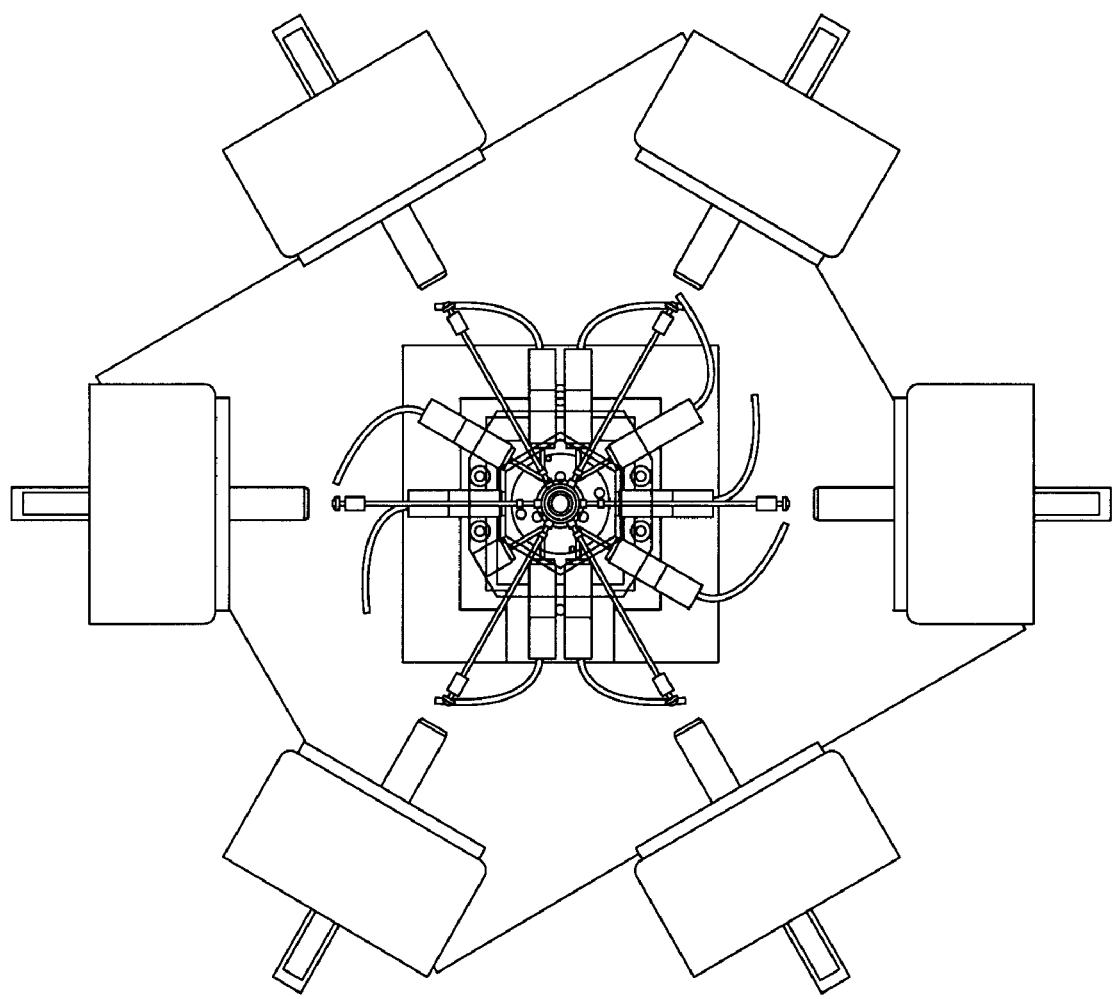
FIG. 6 illustrates an exemplary microfluidic chip with solenoids in accordance with an embodiment of the present invention.

In one exemplary embodiment, the pneumatic valve actuators may be replaced by solenoids in order to tie reagent delivery and valve actuation into a reliable and compact system. While the pneumatic valve actuators require two external valves to control air flow for each on-chip valve, the solenoids only require two wires for proper operation. In addition, since the operation of valves only requires two positions (i.e., on and off positions), solenoids provide a suitable actuation choice. FIG. 6 illustrates six exemplary solenoids that are positioned in the periphery of the chip. In another embodiment these solenoids may be placed in configurations where they are not coaxial with the chip valve plungers. In one example embodiment, the solenoids may be placed underneath the chip and its heater. In this space-saving configuration, the plungers may be driven by appropriately-shaped brackets that connect each solenoid-plunger pair.

In accordance with another example embodiment of the present invention, to make more efficient use of space around the chip and to allow a wider choice of solenoids, the chip geometry may be changed from rectangular to hexagonal, leading to equidistant spacing of valves around the perimeter of the chip and a wedge-shaped real estate for each valve actuator. In addition, such chips may be easier to manufacture because they possess a high degree of symmetry, allowing computer numerical control (CNC) techniques to be used, where the same operation can be repeated 6 times on all the faces.

One exemplary embodiment comprises hexagonal chip with a cylindrical reaction chamber. By the way of example, and not by limitation, a reaction chamber that is 5 mm in diameter and 3 mm in height may be implemented. The volume of this exemplary reaction chamber is 60 μL but the maximum amount of liquid may limited to less than the full capacity of the reaction chamber (e.g., 50 μL) to avoid unintended liquid losses through the vents. In one embodiment, a number of channels (e.g., 6 channels) used for delivery of reagents and product elution may enter the reactor horizontally along the floor of the reactor, while the vent inlets and outlets may enter vertically through the center of the ceiling. Placing the vents closer to the edges of the chip may lead to liquid loss as the meniscus fills the corner between the ceiling and the walls. The vent channels, in this exemplary embodiment, make a 90-degree turn and connect to the fittings (e.g., 10-32) that enter the chip horizontally. The floor of the reactor may have a curvature where the walls meet the floor. As opposed to the reaction chambers with sharp corners, the curveted section that is designed in accordance with embodiments of the present invention lacks the crack-initiating points that can lead to cracks through the floor of the reactor.

The chip, in accordance with an example embodiment, separates into two components: a 'reactor' and a 'lid' that disconnects where the ceiling meets the reactor walls. The lid may have a circular protrusion that is slightly larger in diameter than the reactor, and can therefore form a tight press fit when inserted in the top portion of the reactor. This configuration advantageously allows the reactor to maintain pressures of up to hundreds of psi. The reactor and the lid may be held together by a plurality of screws that thread directly into the reactor part and are, for example, placed symmetrically around the reactor. In one example embodiment, three screws may be used to implement this configuration. In other embodiments the chip can be held together by a variety of clamps. In another embodiment, the layers can be permanently bonded together.

Since metal pins cannot be used for reagent delivery (especially [F-18]fluoride), in one example embodiment, where all reagents enter and exit the chip from the bottom of the chip through vertical channels, a chip-complementary interface base may be provided to couple macroscopic tubing and the chip in an efficient manner. Such a base further allows easy mounting and removal of the chips from the instrument. FIG. 6 illustrates one such example embodiment of a chip with a base adaptor and six large solenoids in the periphery that push and pull the plungers in and out of the chip. This chip arrangement further allows easy integration of a Peltier-based heating system, and uses the space above the chip for easy camera access. Further details regarding example embodiments of the present invention related to the lid, the reactor and the interface are disclosed herein.

Figure 15A:
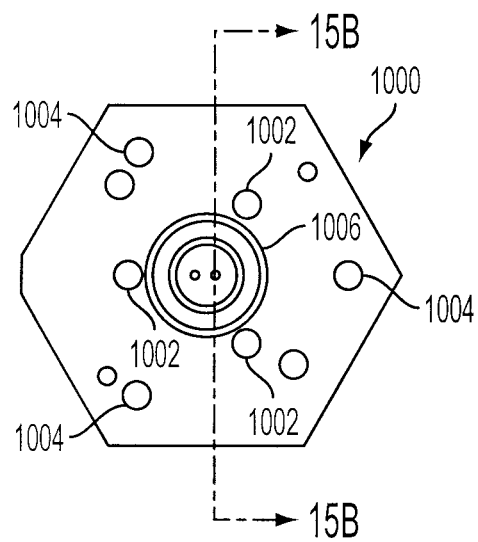
FIG. 15 illustrates a lid section of an exemplary microfluidic chip in accordance with an embodiment of the present invention.
Figure 15B:
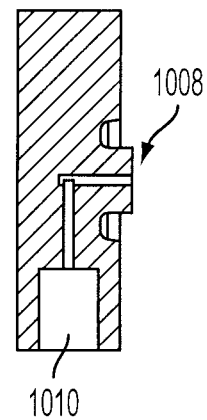
Figure 15C:
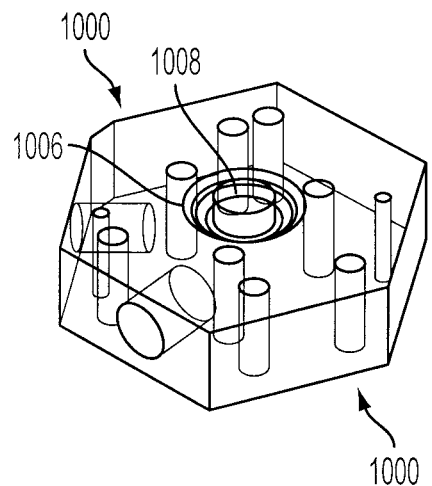
Figure 15D:
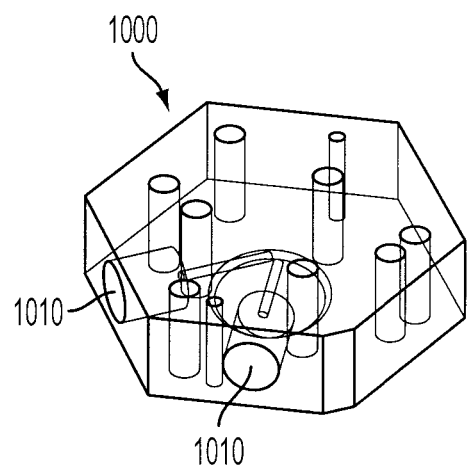

FIGS. 15(A) to (D) illustrate the 'lid' section 1000 of a hexagonal chip in accordance with an example embodiment of the present invention. FIG. 15(A) shows a bottom view of the lid section 1000 with a plurality of first set of holes 1002 that are used for attachment of the lid section 1000 to the 'reactor' portion of the chip. FIG. 15(A) further illustrates a plurality of a second set of holes 1004 that are used for the attachment of the assembled chip to the 'interface.' A groove 1006 is also shown in FIG. 15(A) that is used for the placement of an o-ring. FIG. 15(B) is a cross-sectional view of the lid section 1000 along the plane A-A. FIG. 15(B) illustrates the center part 1008 of the lid section 1000 that press fits into the 'reactor portion' of the microreactor. Vent port 1010 with a 10-32 fitting is also shown in FIG. 15(B). FIG. 15(C) shows another bottom view of the lid section 1000, illustrating a groove 1006 for holding an o-ring, and a center part 1008 of the lid section 1000. FIG. 15(D) shows a top view of the lid section 1000 with further illustrations of a plurality of vent ports 1010 with, for example, 10-32 fittings.

Figure 16A:
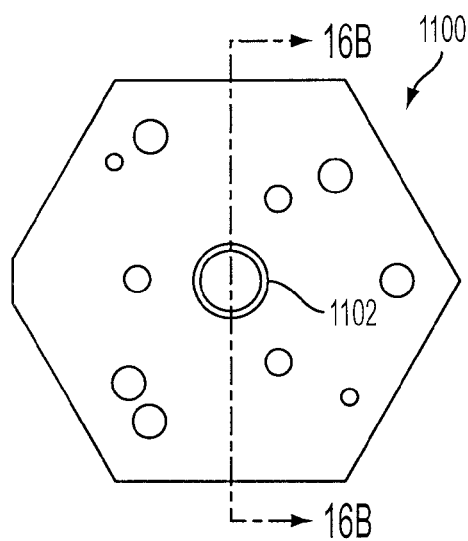
FIG. 16 illustrates a reactor section of an exemplary microfluidic chip in accordance with an embodiment of the present invention.
Figure 16B:
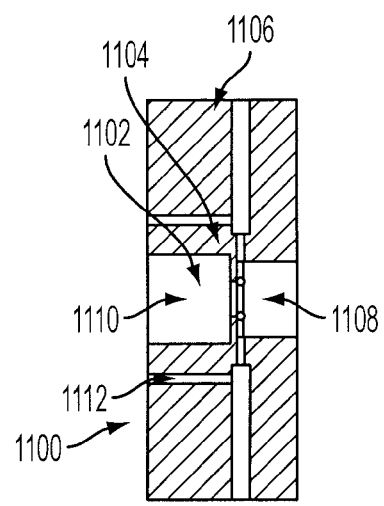
Figure 16C:
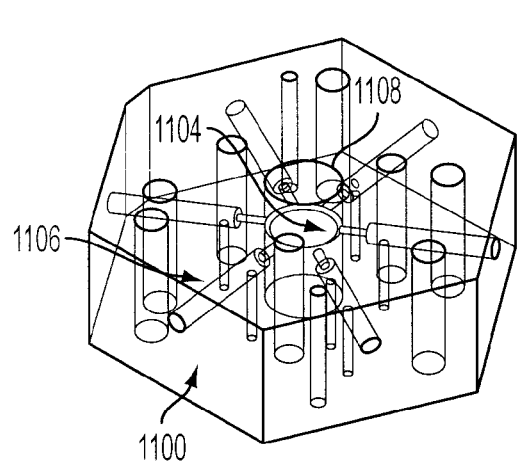
Figure 16D:
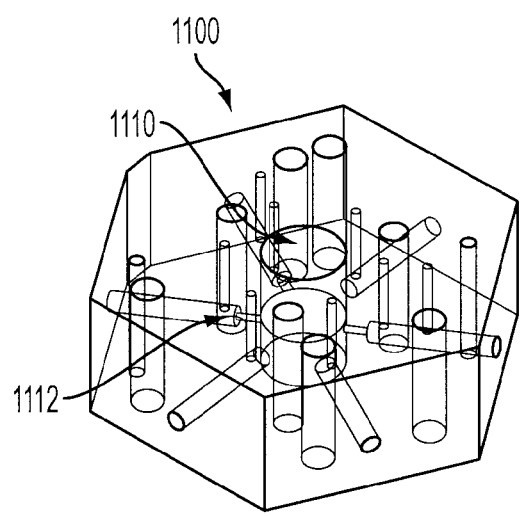

FIGS. 16(A) to (D) illustrate the 'reactor' section 1100 of a hexagonal chip in accordance with an example embodiment of the present invention. FIG. 16(A) shows a top view of the reactor section 1100 with a curvature 1102 (missing in the figure) at the bottom of the reaction chamber that prevents crack formation in the thin floor. FIG. 16(B) is a cross-sectional view of the reactor section 1100 along the plane A-A. FIG. 21(B) illustrates the curvature 1102, along with fluid inlets 1104 that run from the barrel to the reaction chamber 1108. FIG. 16(B) further illustrates valve plunger barrels 1106, the reaction chamber 1108 (with exemplary capacity of 60 µL). The lid section 1000 press fits into the reaction chamber 1108 opening, forming a closed cylinder. FIG. 16(B) also illustrates a counterbore 1110 for heater insertion, and a plurality of fluid inlets 1112 from the interface to the barrels. FIG. 16(C) is another top view of the reactor section 1100, which further illustrates the locations the reaction chamber 1108, fluid inlets 1104 from the barrel to the reaction chamber 1108, and the valve plunger barrels 1106. FIG. 16(D) is a bottom view of the reactor section 1100. FIG. 16(D) further illustrates a counterbore 1110 for the insertion of a heater, and fluid inlets 1112 from the interface to the barrels.

Figure 17A:
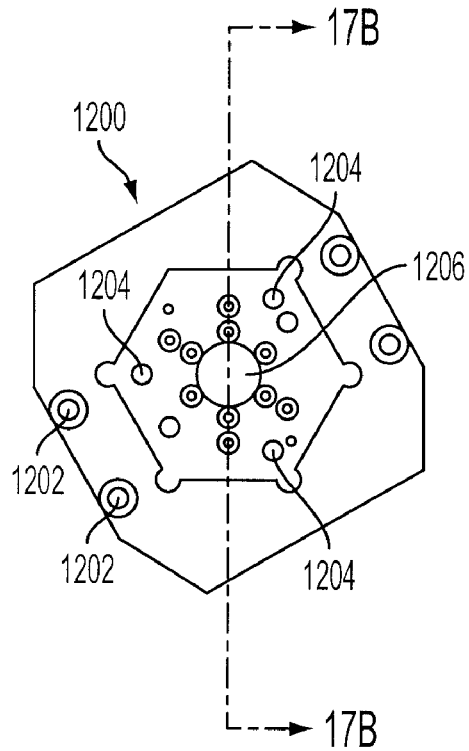
FIG. 17 illustrates an interface section of an exemplary microfluidic chip in accordance with an embodiment of the present invention.
Figure 17B:
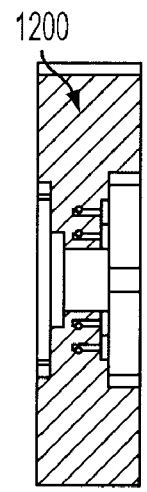
Figure 17C:
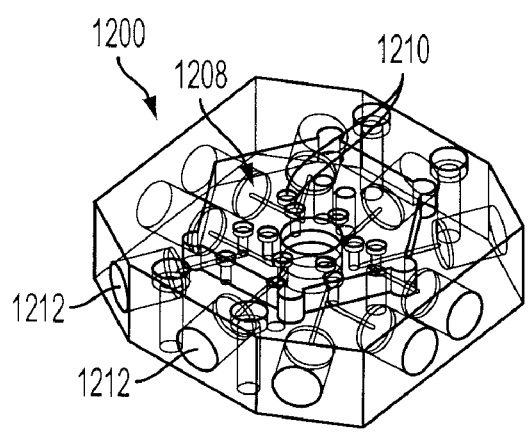
Figure 17D:
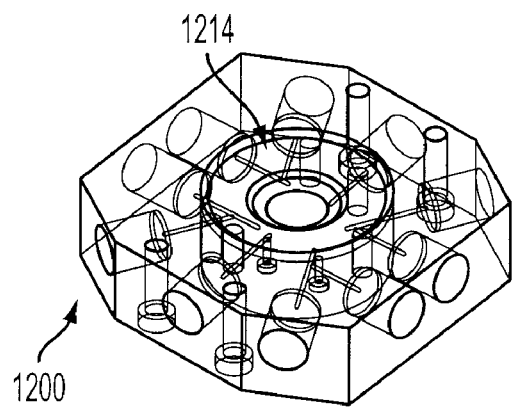

FIGS. 17(A) to (D) illustrate the 'interface' section 1200 complementary to the hexagonal chip in accordance with an example embodiment of the present invention. FIG. 17(A) shows a top view of the interface section 1200, comprising a plurality of holes 1202 for mounting the interface on the instrument. FIG. 17(A) also illustrates a plurality of threaded holes 1204 for mounting the chip, and a through hole 1206 in the center of the interface section 1200 that is used for insertion of a heater into the chip. FIG. 17(B) is a cross-sectional view of the interface section 1200 along the plane A-A. FIG. 17(C) is another top view of the interface section 1200. FIG. 17(C) illustrates a hexagonal well 1208 that houses the hexagonal chip as well as a plurality of round wells 1210, used for the placement of o-rings that form a seal between the chip and the interface 1200 around each port. FIG. 17(C) further illustrates a plurality of ports 1212 (e.g., ¼-28 in size) that are used for delivery of reagents and product exit. FIG. 17(D) illustrates a bottom view of the interface section 1200, comprising an indentation 1214 that is provided to increase the contact area of the heat transfer block with the Peltier device.

FIGS. 18(A) to (C) illustrate a combined diagram of the chip and interface assembly 1300 in accordance with an example embodiment of the present invention. FIG. 18(A) shows a top view of the combined assembly 1300. FIG. 18(B) is a cross sectional view of the assembly 1300 along the plane A-A. FIG. 18(B) illustrates an opening 1302 through which a heating block may be inserted through the interface into the reactor section 1100 and pressed against the reaction chamber floor. Liquid ports 1304 and plunger ports 1306 are also shown in FIG. 18(B). FIG. 18(C) illustrates a combined assembly 1300 that comprises a lid section 1000, a reactor section 1100, and an interface section 1200.

In accordance with another embodiment of the present invention, the reagent barrels may be smooth and uniform with flat ends that allow the plungers to seal the reactor in the closed form and maintain pressures of up to hundreds of psi. Two types of port arrangements may be provided around the reactor. One type comprises a single inlet close to the end of the barrel. These ports may be used to deliver reagents that are loaded into the instrument in fixed volumes, such as Kryptofix2.2.2 and precursor. These ports may also be implemented for allowing F-18 entrance from the ion exchange column, and for product exit. The second type comprises two ports in the same barrel. Accordingly, when the plunger is in the closed position, the thinner center portion of the plunger allows fluid communication between these two ports. This mechanism allows priming the reagents, such as acid and water, right up to the reaction chamber without the need to go through the reaction chamber. All or some of the reagents may be preceded by air in the channels between reagent vials and the chip. The air is typically expunged through the bypass channels in the process of priming. By employing the valves in accordance with embodiments of the present invention, when liquids are brought right up to the reaction chamber, the user can be assured that when the valve opens and a specified amount of reagent is dispensed, it is indeed the reagent, and not air, in front of it. The inlet may be located near the end of the barrel, closest to the reaction chamber, and the outlet may be placed further down. When the plunger is in the open position, the first inlet is in fluid communication with the reaction chamber while the second port is blocked by the plunger. In this state, any dispensed liquid flows into the reactor, while in the closed state it flows into the waste through the bypass mechanism.

Figure 19A:
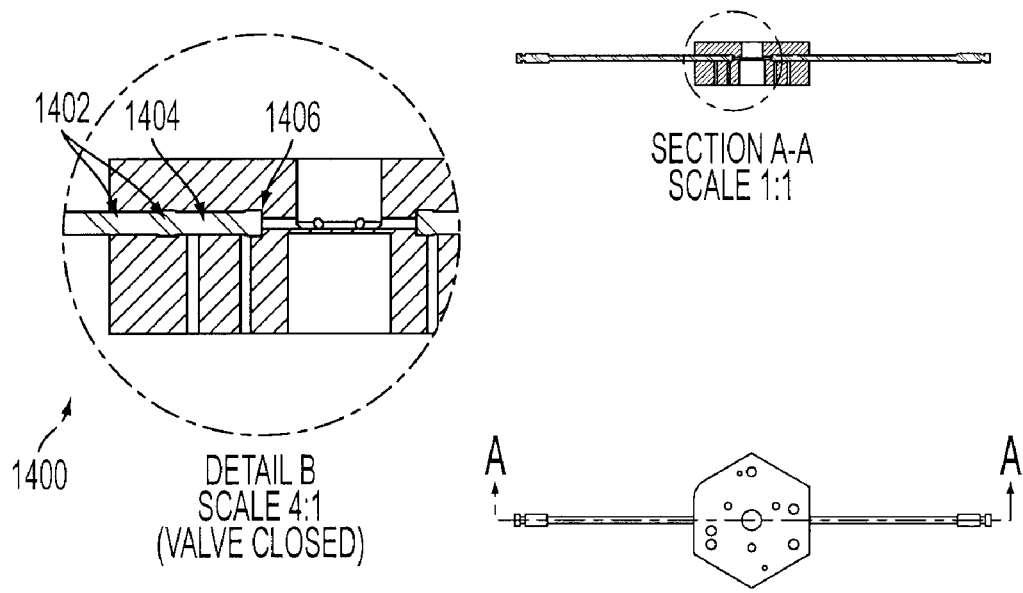
FIG. 19 illustrates an exemplary plunger valve operation in accordance with an embodiment of the present invention.
Figure 19B:
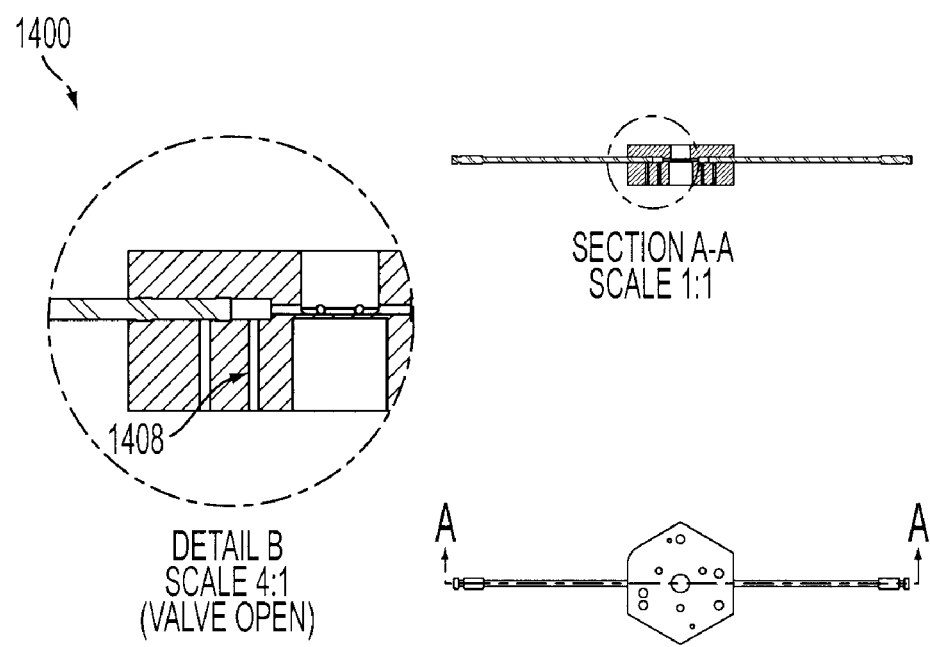

FIGS. 19(A) and (B) illustrate a scale model of an example plunger and method of operation thereof in accordance with an exemplary embodiment of the present invention. The 'dual port' plunger is comprised of a plurality of ridges 1402 separated by thin portions 1404 of the plunger. FIG. 19(A) illustrates the scenario in which the valve is closed, by inserting the plunger all the way to the right-most position, so that it is pressed against the dead stop 1406 at the end of the barrel. The reaction chamber is sealed and the two vertical points are now in fluid communication allowed by a combination of ridges 1402 and thin portions 1404 on the plunger tip. This configuration allows the reagents to be primed (expunging the air in front of the liquid through the bypass outlet). FIG. 19(B) illustrates the scenario in which the valve is opened by retracting the plunger from the right-most position, just enough to open communication between the first port 1408 and the reaction chamber while the second port 1410 is still blocked. The liquid actuated to the first port 1408 may now enter the reaction chamber.

Figure 20A:
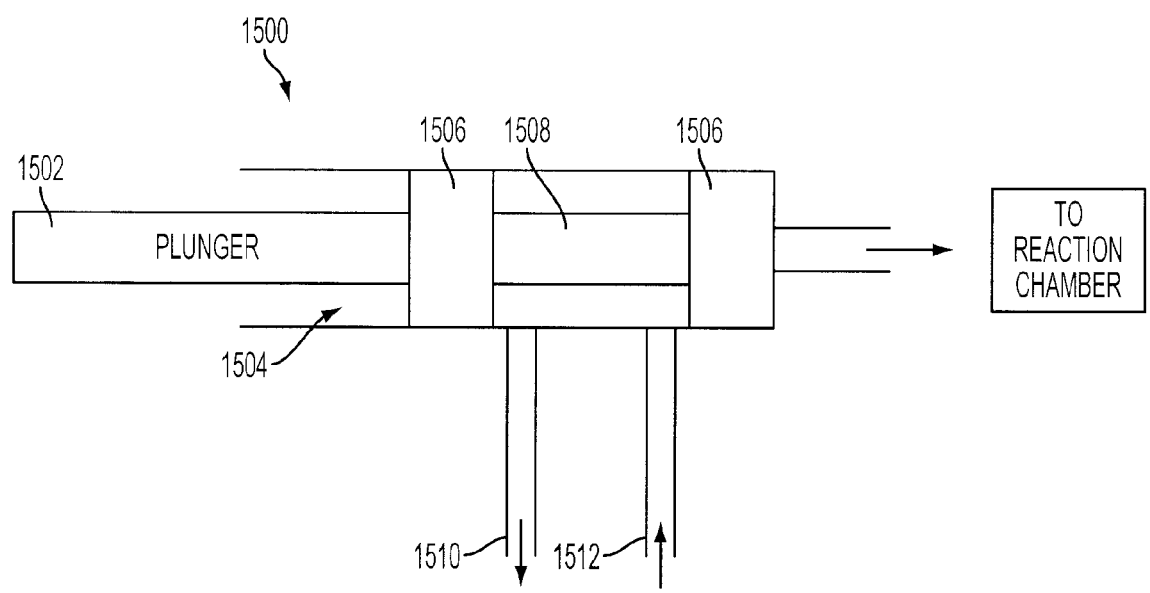
FIG. 20 illustrates an exemplary plunger valve in accordance with an embodiment of the present invention.

FIGS. 20(A) and 20(B) illustrate a not-to-scale example 'dual port' plunger valve 1500 in accordance with an exemplary embodiment of the present invention. This plunger provides an example configuration of a plunger that may be used in connection with FIG. 19. FIG. 20(A) illustrates the operation of the plunger valve 1500 in priming bypass mode. The plunger valve 1500 comprises a plunger 1502 that may be inserted into or retracted from a barrel 1504. The plunger valve further comprises a plurality of ridges 1506 that separate thin portions 1508 of the plunger 1502. As the plunger 1502 is inserted into or retracted from the barrel 1504, bypass outlet 1510 or liquid inlet 1512 ports may be blocked or exposed, allowing the flow of material into or out of the barrel 1502 and the reaction chamber. FIG. 20(B) illustrates the operation of the plunger valve 1500 in the open reactor mode, where the liquid inlet 1512 is exposed to allow the flow of material to the reaction chamber.

Figure 21:
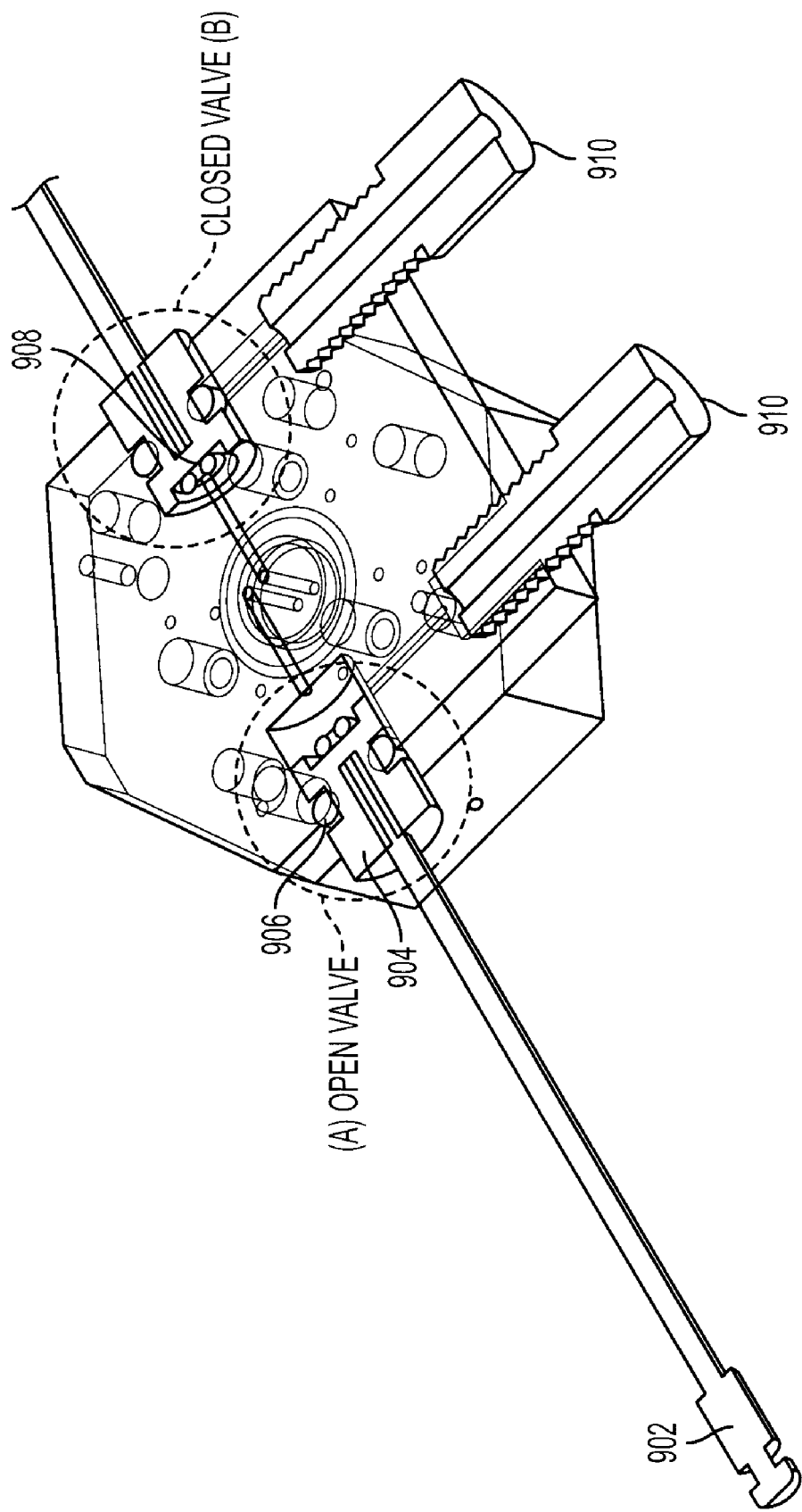
FIG. 21 illustrates an exemplary vent valve in accordance with an embodiment of the present invention.

In accordance with a further embodiment of the present invention, the vents may utilize a different kind of valve. While similar in principle to the single port valves, the vent valves may utilize a mechanism of o-rings in order effect a seal. These valves allow large channel cross sections while minimizing the extended volume. The extended volume is very significant with off-chip valves even when small diameter tubing is used. The volume of the tubing can easily double or triple the volume of the reaction chamber. This leads to significant solvent evaporation during reactions and loss of reaction mixture into vent tubing during boiling. FIG. 21 illustrates vent control valves in accordance with an exemplary embodiment of the present invention. Two valve positions are illustrated in FIG. 21: (A) open valve, and (B) closed valve positions. The valves are controlled by moving the plungers 902 back and forth using, for example, 2-way pneumatic actuators. FIG. 21 further illustrates the use of large o-rings 906 that are positioned within the PEEK plunger tip 904. The large o-rings 906 seal the gas path in an open valve position, preventing gas escape along the barrel. FIG. 21 also illustrates the use of smaller o-rings 908 that are also positioned within the plunger tip 904. The small o-rings seal off the reaction chamber from all external gas connections when the valve is in closed position. FIG. 21 also shows fittings 910 (e.g., size 10-32) that are used for connecting Nitrogen and vent outlet tubing to the chip.

The on-chip vent valves in accordance with the example embodiments of the present invention eliminate these problems. They also allow the use of large diameter tubing off-chip and large cross sections of channels on-chip, which in turn lead to higher flow rates of gas over liquid at lower pressures and therefore faster evaporation of solvents during evaporation steps. In one exemplary embodiment, the plungers may be driven by air cylinders, allowing to hold hundreds of psi pressures in the reactor with less than 100 psi actuation pressure. In one embodiment, the vents may be extended with tubing that leads to external valves.

In one example embodiment of the present invention, the heat transfer from the heating element, located below the reactor, to the contents of the reactor is optimized by selecting an appropriate thickness for the floor of the reactor. In one example, the floor thickness is 250 μm. Many of the materials from which the chips can be made are thermal insulators rather than conductors (such as PEEK or poly DCPD). This usually results in a temperature drop which is significant even across a 250 um barrier. In case of DCPD the lag at 180 degrees is about 20 degrees. The reactor section may be constructed using a range of materials that combine the following properties: chemical, thermal and radiation stability, and manufacturability.

Furthermore, at least a portion of the lid section may be preferably transparent. This feature allows monitoring of the reaction chamber visually with a camera. Machine vision techniques may further be used to track the changes in the reaction chamber that are indicative of certain events, such as reaction completion, which may be used to trigger other events. For example instead of waiting for evaporation to be fully completed and allowing extra time to ensure the reactor is dry, a camera may be used to establish a feedback loop. According to this example embodiment, the camera may provide a signal to the controller the instant the reaction chamber becomes moisture free, triggering the next steps, which include cooling the reactor, stopping gas flow and filling the precursor. In the absence of such feedback mechanism, one may need to obtain an estimate for the time required to complete a given step, by taking the longest observed time necessary to complete the step and adding about 20% to it. In such a scenario, even if the step is completed in a shorter time duration, the system still needs to wait for the pre-determined duration of time. Furthermore, if the step takes longer than estimated, the whole synthesis process may be at risk because the next step would have started before the preceding step has completed.

In accordance with another example embodiment of the present invention, the dryness of the reaction chamber may be monitored using capacitance sensors. Accordingly, a plurality of conductive probes (e.g., 3 probes) may be placed below the bottom edge of the reactor that are configured to measure the change in capacitance between a dry and a wet reactor. This sensing mechanism may be used in conjunction with time to assess dryness within the reactor. In accordance with yet another example embodiment, the dryness of the reaction chamber can be monitored with a flow sensor located in the vent line downstream from the chip. The flow rate rises as evaporation starts and drops to baseline when there is no solvent left in the reactor.

In accordance with another example embodiment of the present invention, the dryness of the reaction chamber may be monitored using laser sensors. Accordingly, reflective laser sensors may be aimed at the bottom edge of the reactor to measure the difference in the amount of light returned from a wet and a dry reactor. Additionally, or alternatively, a Thru-Beam laser sensor may be used to measure the difference in the amount of light that passes through the reactor in wet and dry reactor conditions. In this configuration, the Thru-Beam laser sensor may, for example, be placed so that the light beam passes through the bottom edge of the reactor from the sides.

While a glass lid provides the desired transparency for incorporation of a camera system, it may be difficult and expensive to fabricate such a lid made entirely of glass. To this end, in accordance with an example embodiment of the present invention, a lid may comprise a glass window within a frame that is made up of plastic material, such as PEEK or DCPD. This window may be press-fitted into the frame, which hosts the threaded connections. The glass portion may contain, for example, only two channels which can be either drilled or etched onto the glass.

Figure 22:
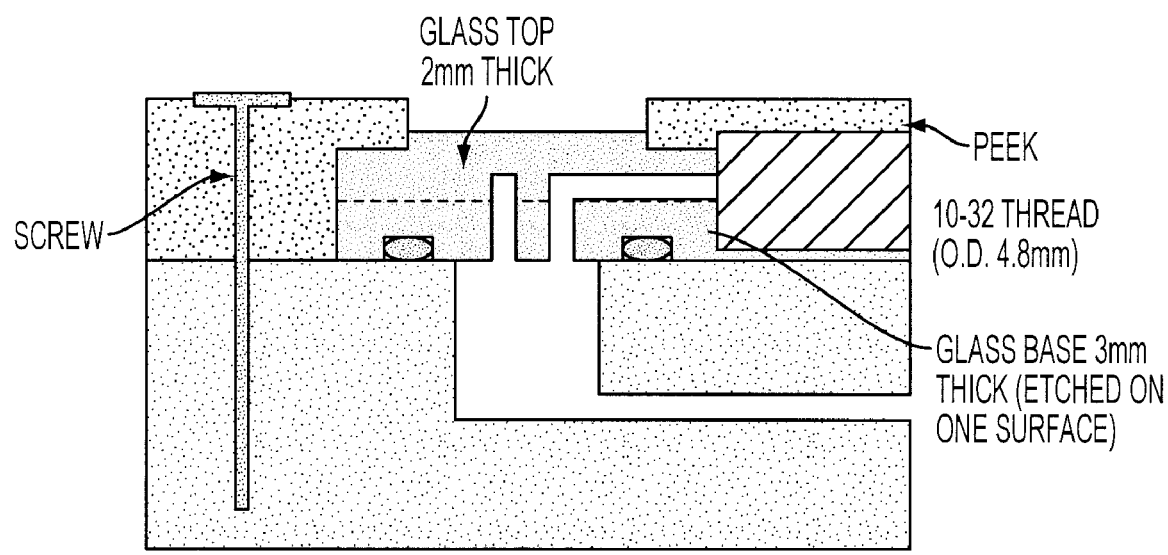
FIG. 22 illustrates a lid section of an exemplary microfluidic chip in accordance with an embodiment of the present invention.
Figure 23:
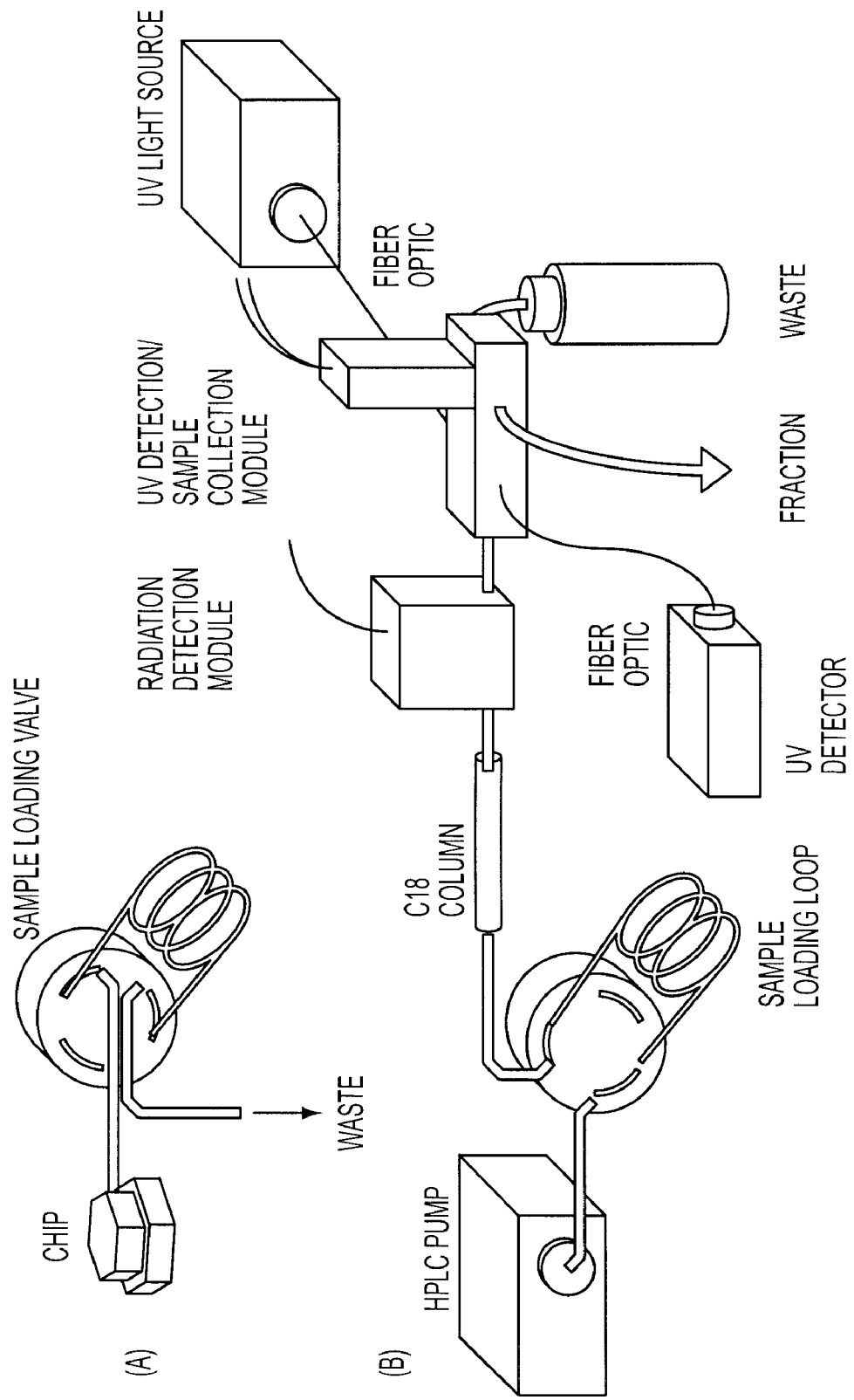
FIG. 23 is a product transfer and purification system diagram in accordance with an exemplary embodiment of the present invention.

FIG. 22 illustrates a combination glass/PEEK lid in accordance with an example embodiment of the present invention. Although the following description provides specific values and parameters associated with the exemplary lid of FIG. 22, these values and parameters may be modified to produce other example lids without departing from the scope of the various embodiments of the present invention. The various sections of the lid as illustrated in FIG. 22 may be identified as follows:

Two layer glass chip, total thickness 5 mm, hexagonal footprint, approximate area 10×12 mm.

O-ring groove etched into bottom of base glass layer (300 micron depth by 620 micron width); small section o-ring inserted into etched groove.

Channels etched into bottom of top layer; this gives hemispherical horizontal channel to 10-32 holes.

Two 0.6 mm diameter holes drilled through base layer.

Chip etched, drilled, fused and diced at wafer level to reduce volume costs.

The chip may be held together by three bolts that fit through the holes in the top layer and thread into the bottom layer. The chip may have three more holes that go all the way through both layers. These are used to bolt the chip to the interface layer. This rigid attachment creates tight seals with o-rings around the ports, allowing liquids in and out of the chip via the interface. In other example embodiments, other ways of securing the chip on the interface base, including various kinds of latching may be effected. However, bolting the chip to the interface has the advantage of being simple to implement while saving space.

The heater may be inserted through the opening in the interface layer into the counterbore in the bottom ("reactor") part of the chip. The tolerances in various layers can make the gap between the heater and the reaction chamber floor anywhere from 0 to 300 microns. In order to avoid an insulating air gap, a heat transfer paste may be placed on top of the heater before chip insertion. The paste can be cleaned out completely and replaced every time a chip is removed. In an alternative embodiment, springs may be placed at various points in the chip-interface assembly. If the springs are placed underneath the interface layer (springs that pull it down, not push it up), then when the chip is bolted to the interface, the interface will lift up to the chip which is now resting on top of the heater. This will always minimize the gap between the heater and the chip (assuring contact between the two, independent of the adding up of the tolerances, which may differ in various chip-interface combinations). This configuration also eliminates the need for the heat transfer compound. In order to maximize the heat transfer to the reaction chamber, and minimize heat transfer to the rest of the chip, a significant gap around the cylindrical heater may be left open. Thus by intentionally leaving an insulating air gap, any contact between the heater and the chip on the sides may be avoided.

Figure 7:
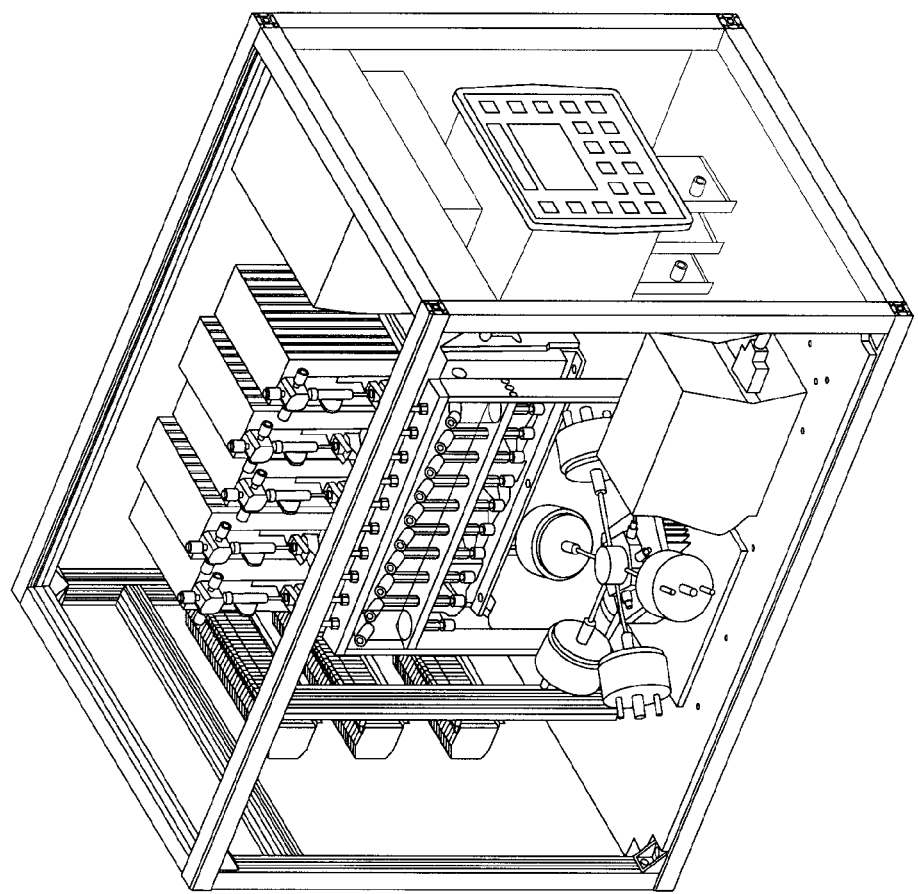
FIG. 7 illustrates an exemplary microfluidics-based instrument in accordance with an embodiment of the present invention.
Figure 7:
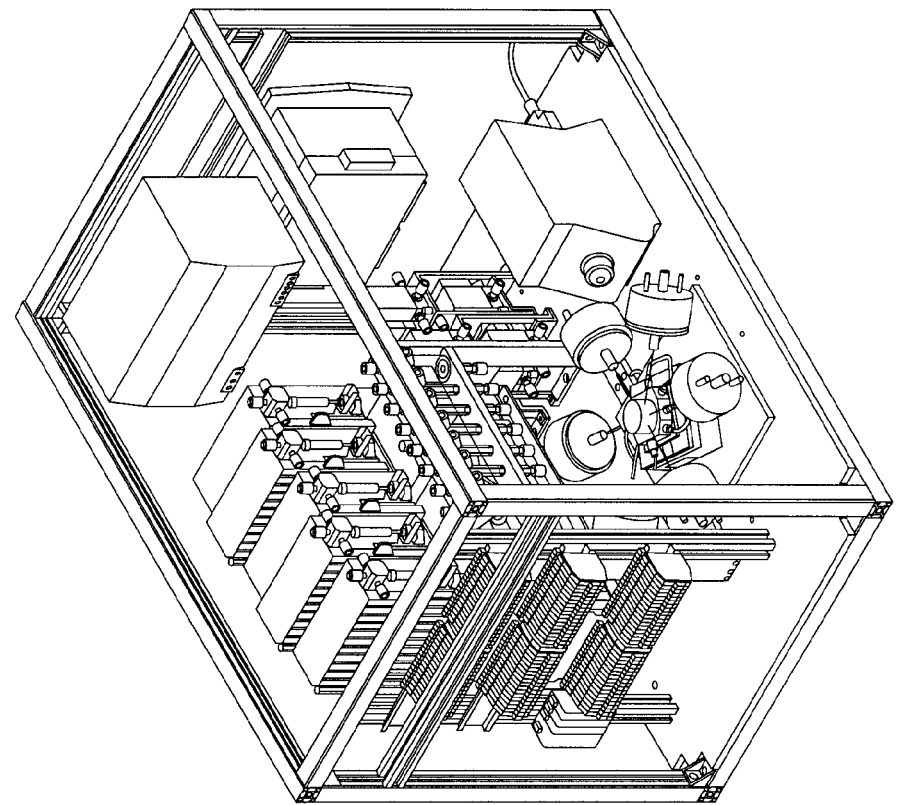
Figure 8:
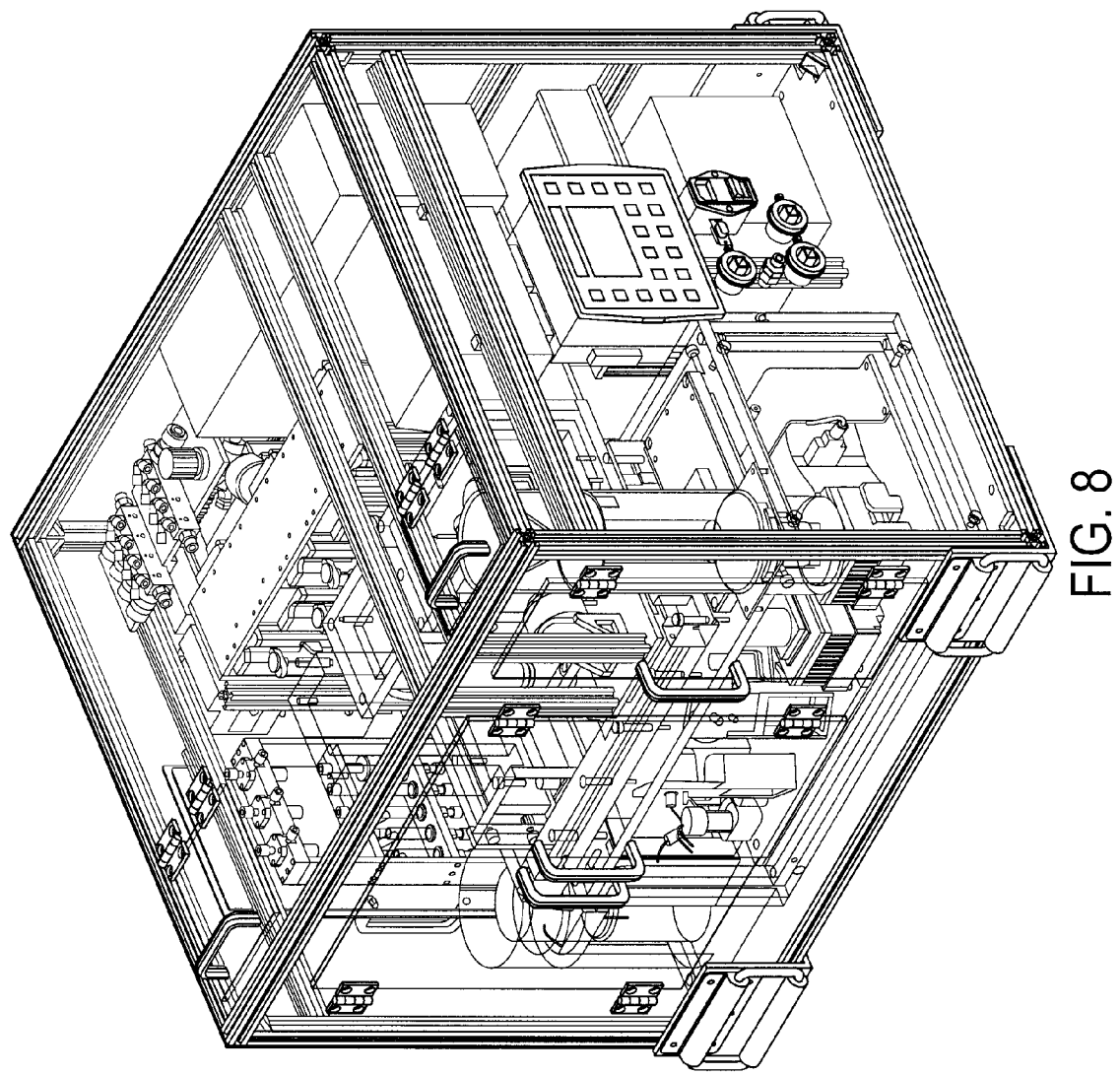
FIG. 8 illustrates an exemplary microfluidics-based instrument in accordance with an embodiment of the present invention.
Figure 9:
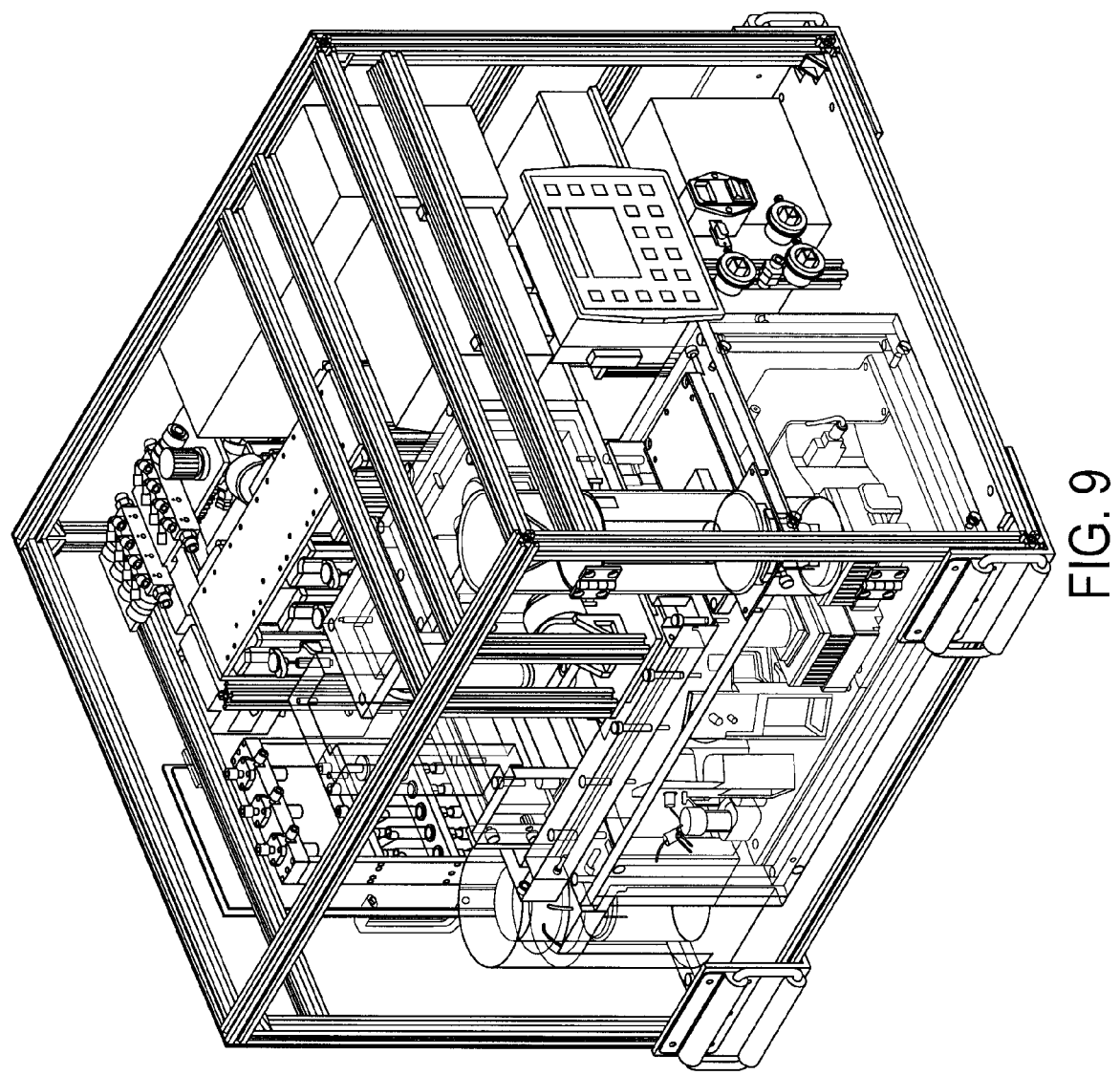
FIG. 9 illustrates an exemplary microfluidics-based instrument in accordance with an embodiment of the present invention.
Figure 10:
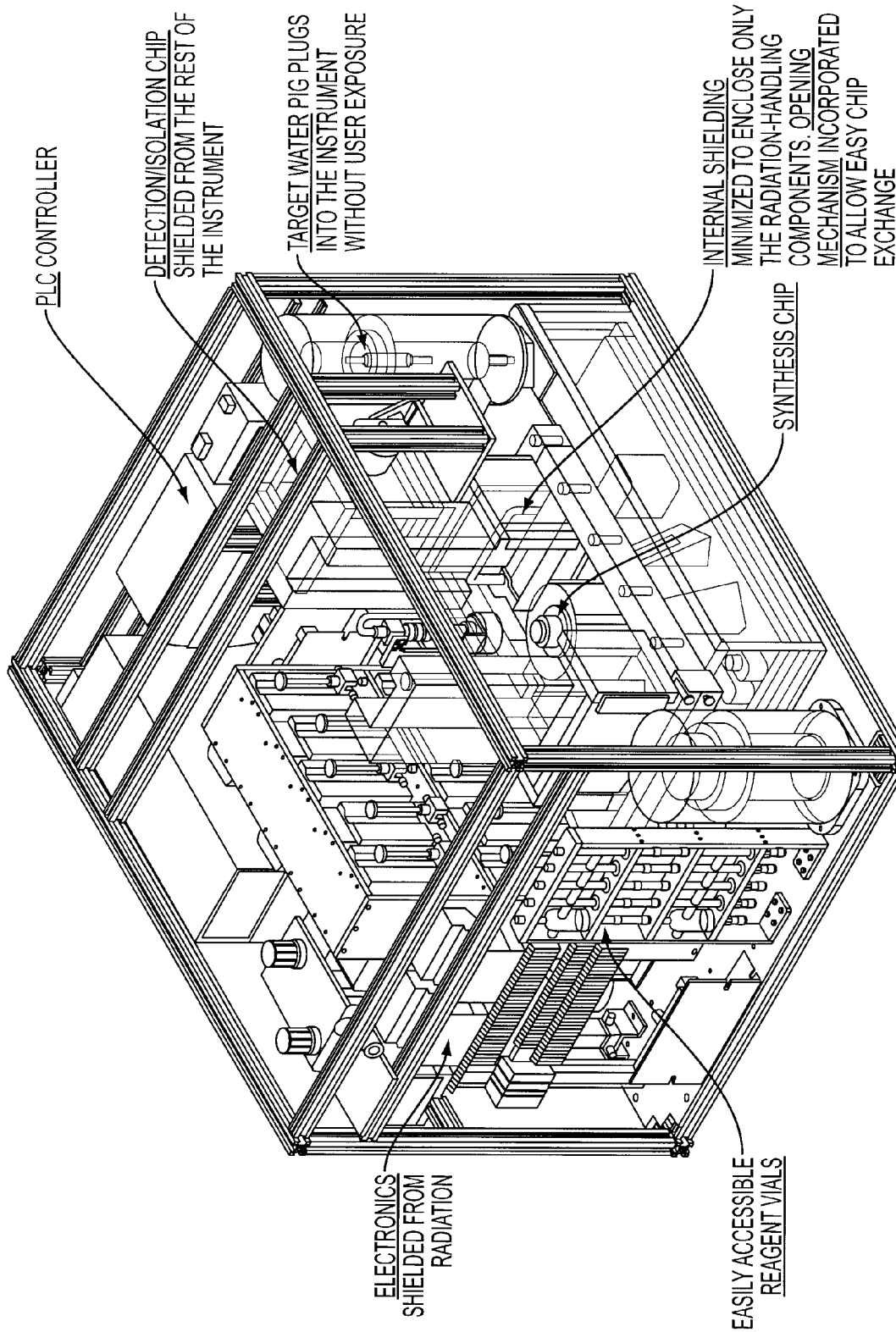
FIG. 10 illustrates an exemplary microfluidics-based instrument in accordance with an embodiment of the present invention.

In another example embodiment of the present invention, the reagent containers are designed to be located above the syringe drivers. This configuration allows the drawing of liquids to take place efficiently from the bottom of the containers, and to minimize the length of tubing between the reagent vials, syringe drivers and the chip. The entire process may be controlled using, for example, a Visual Basic program through a PLC (programmable logic control) controller. FIGS. 7-10 illustrate example embodiments of a device in accordance with embodiments of the present invention. Specifically, FIG. 7 illustrates an exemplary device comprising basic components such as the chip, solenoids, and PLC controller. FIG. 8 illustrates an example instrument which is capable of performing synthesis and isolation of biomarkers—with instrument covers closed. FIG. 9. illustrates an exemplary instrument with covers removed, and FIG. 10 illustrates an exemplary instrument where the various components and features associated with the device are also identified.

Example Embodiment

Synthesis of [$^{11}$C]-Labeled Product

By the way of example, and not by limitation, for a process utilizing a carbon-11-labeling agent (e.g., methyl iodide, methyl triflate, carbon monoxide, hydrogen cyanide), the following steps may be performed within a microfluidic device:

a) Receive [$^{11}$C]-labeling agent from the cyclotron target or post-irradiation processor b) Generate a solution of reactive [$^{11}$C]-labeling agent in an organic and/or polar aprotic solvent (acetonitrile, DMF, DMSO, etc.)

c) Provide a solution of a reactive precursor in an organic and/or polar aprotic solvent (acetonitrile, DMF, DMSO, etc.)

d) React the [$^{11}$C]-labeling agent with the precursor using a $S_N2$ nucleophilic substitution reaction or other suitable reaction to create a new carbon-nitrogen, carbon-oxygen, carbon-sulfur or carbon-carbon bond, using heat or microwave energy if necessary e) Purify the initial [$^{11}$C]-labeled product by, for example, solid phase extraction or chromatography f) React the purified initial [$^{11}$C]-labeled product with a second reagent to generate the final [$^{11}$C]-labeled product (e.g., hydrolysis of protecting group(s), if necessary)

g) Purify the final [$^{11}$C]-labeled product by solid phase extraction or chromatography h) Remove solvents from the [$^{11}$C]-labeled product i) Deliver the final [$^{11}$C]-labeled product to a final product vial.

Example Embodiment

Control System

The following disclosure is a description of the equipment, process and control in accordance with the various embodiments of the present invention. This instrument is one embodiment of the present invention and allows for the automated synthesis and purification of multiple types of radiolabeled compounds for use in the Positron Emission Tomography scanning of animals and humans.

As illustrated in FIGS. 7 to 10, example instruments in accordance with the embodiments of the present invention, may contain equipment consisting of an aluminum frame; stainless steel panel enclosure with access doors, as well as:

a Programmable Logic Controller (PLC) for input/output (I/O) control;

a high resolution CCD camera and machine vision system for viewing the various events within the reactor, as well as for drying and evaporation control;

eight or more automated precision syringe pumps with low internal volume valves and zero dead volume syringes for precision fluid delivery;

eleven high pressure liquid/gas valves for fluid control;

a low internal volume, high pressure, automated control loop valve for trap and release on an ion exchange column;

a low internal volume, high pressure, automated control, distribution valve for column regeneration and system cleaning;

a low internal volume, high pressure, automated control loop valve for loading the crude product into an HPLC injection loop;

a micro-fluidic chip which contains 6 on-chip valves as well as a vented reaction chamber for the synthesis reactions;

a thermoelectric module for the heating and cooling of the reaction chamber;

a manual pressure regulator;

an automated pressure regulator;

gas manifolds;

five high pressure solenoid gas valves;

one low pressure solenoid gas valve;

manual flow control valves;

liquid vials and bottles;

a laptop PC running a Visual Basic control program for overall control of the instrument;

a purification system containing two thermoelectric heaters and coolers, a purification column, an on-board HPLC, and a product separation valve.

Figure 11:
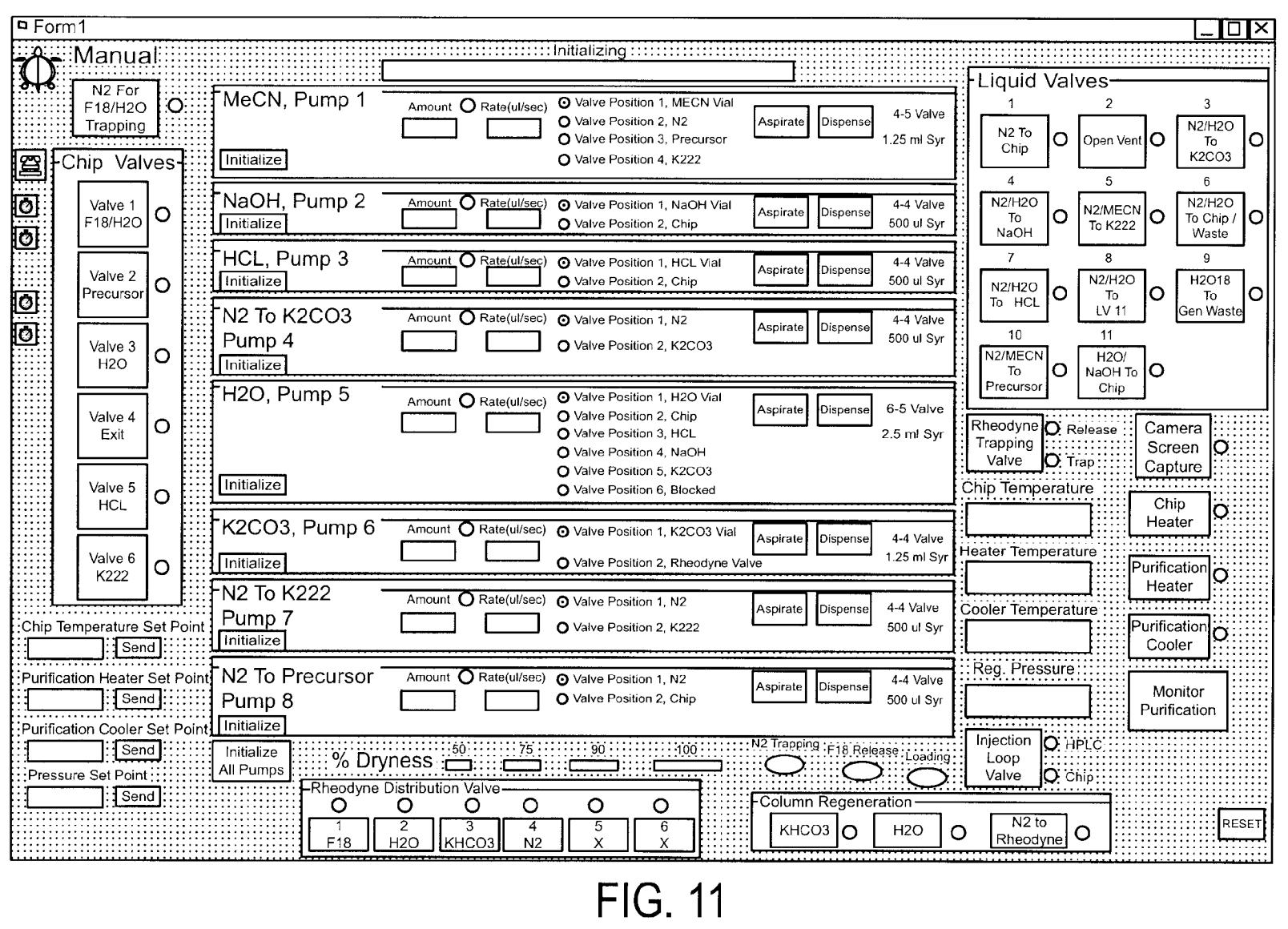
Figure 12:
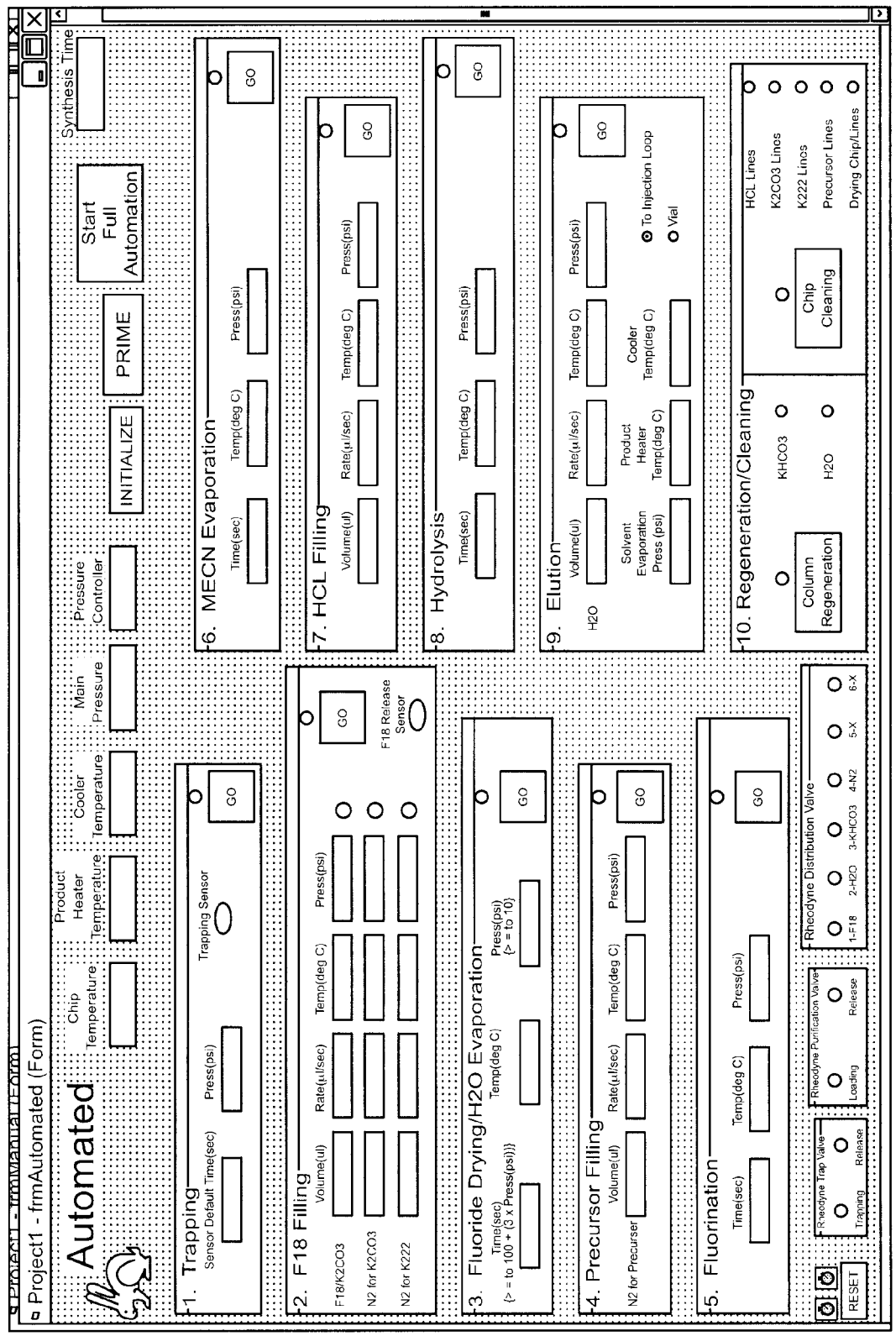
FIG. 12 illustrates a user interface for the microfluidics-based instrument in accordance with an exemplary embodiment of the present invention.
Figure 13:
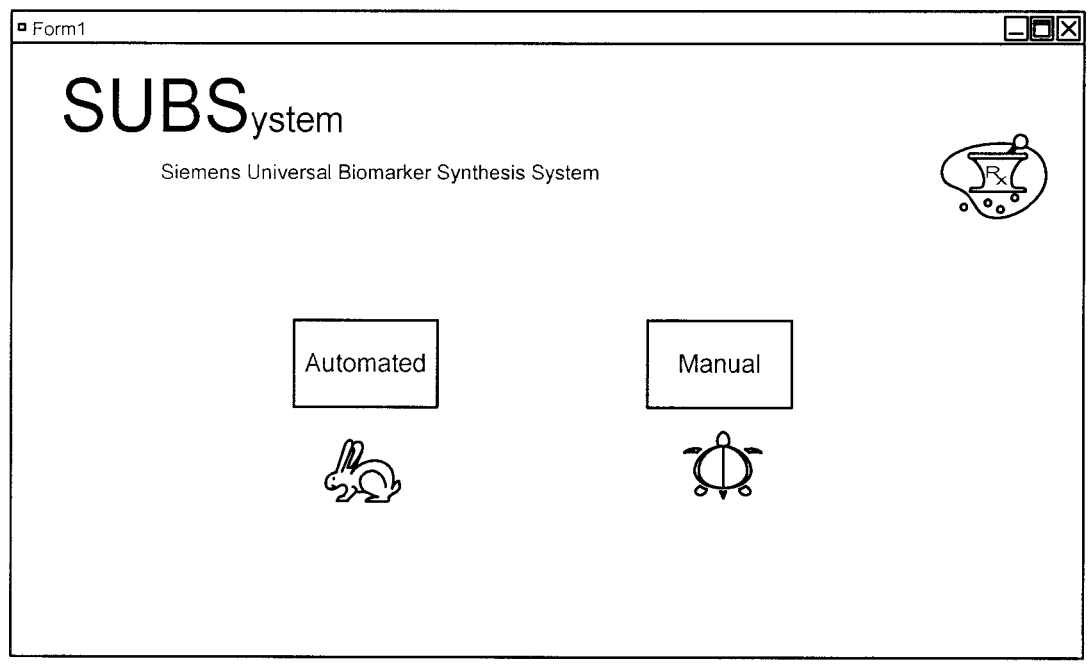
FIG. 13 illustrates a user interface for the microfluidics-based instrument in accordance with an exemplary embodiment of the present invention.

FIGS. 11 to 13 illustrate example user interface screens for operation of the instruments in accordance to the various embodiments of the present invention. Specifically, FIG. 11 illustrates an example input screen for automated radiosynthesis operation in accordance with an embodiment of the present invention. FIG. 12 illustrates an example input screen for manual radiosynthesis operation in accordance with an embodiment of the present invention. FIG. 13 illustrates an example screen that allows a user to select between manual and automated modes of instrument operation. One such device has been implemented as the Siemens Universal Biomarker Synthesis Instrument, which uses a Visual Basic control program, as well as a Ladder Logic PLC for control of the device.

The instrument can be used in one of three modes: (1) Full automation that takes the process from target water to purified product in an injectable formulation with one click of a start button; (2) individual step automation, which allows the user to pause after each synthetic step and decide which parameters to use in the next step, or to skip steps, or to stop the process; and (3) a fully manual mode, where the user can control every device in the instrument such as a valve, pressure regulator, syringe, etc. All modes allow the user to monitor the processes taking place in the chip in real-time by watching the output from a camera placed above the chip on a separate screen. Machine vision can use the same images to drive certain step sequences in the automated process or give the user an indication of step completion in the manual mode.

Example Embodiment

Use of System for Preparation of [$^{18}$F]FLT

Figures 1, 14A:
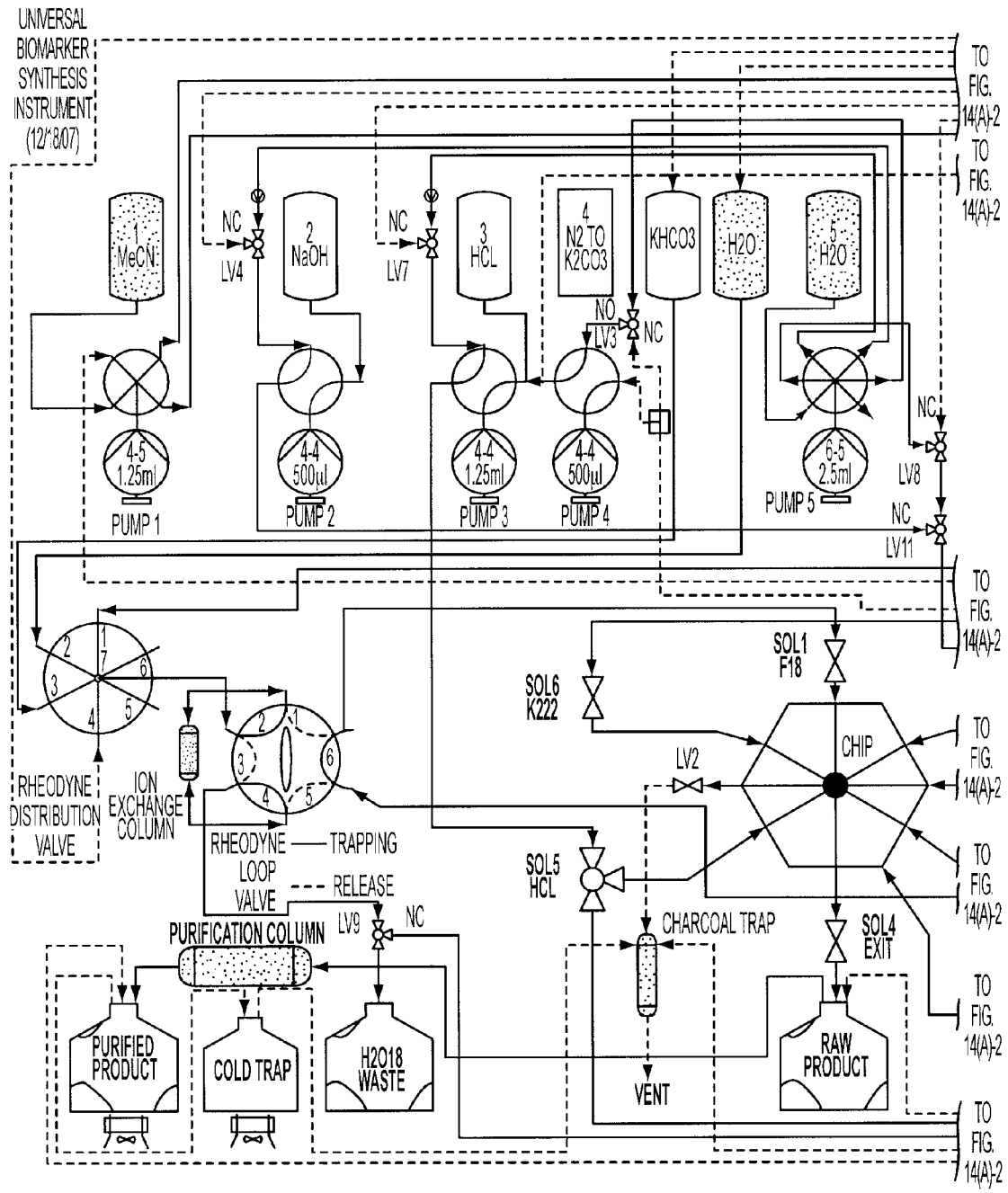
Figures 2, 14A:
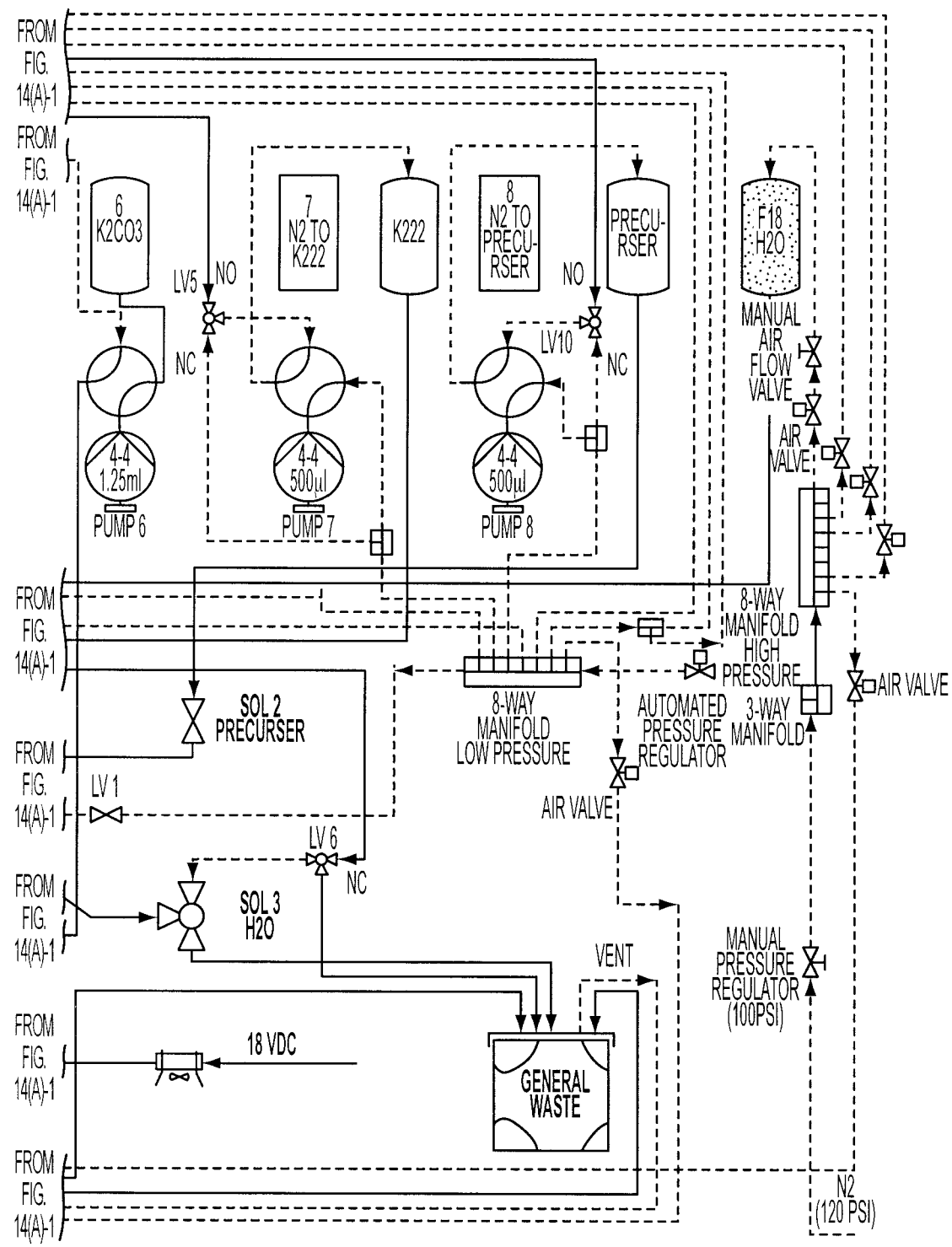
Figures 1, 14B:
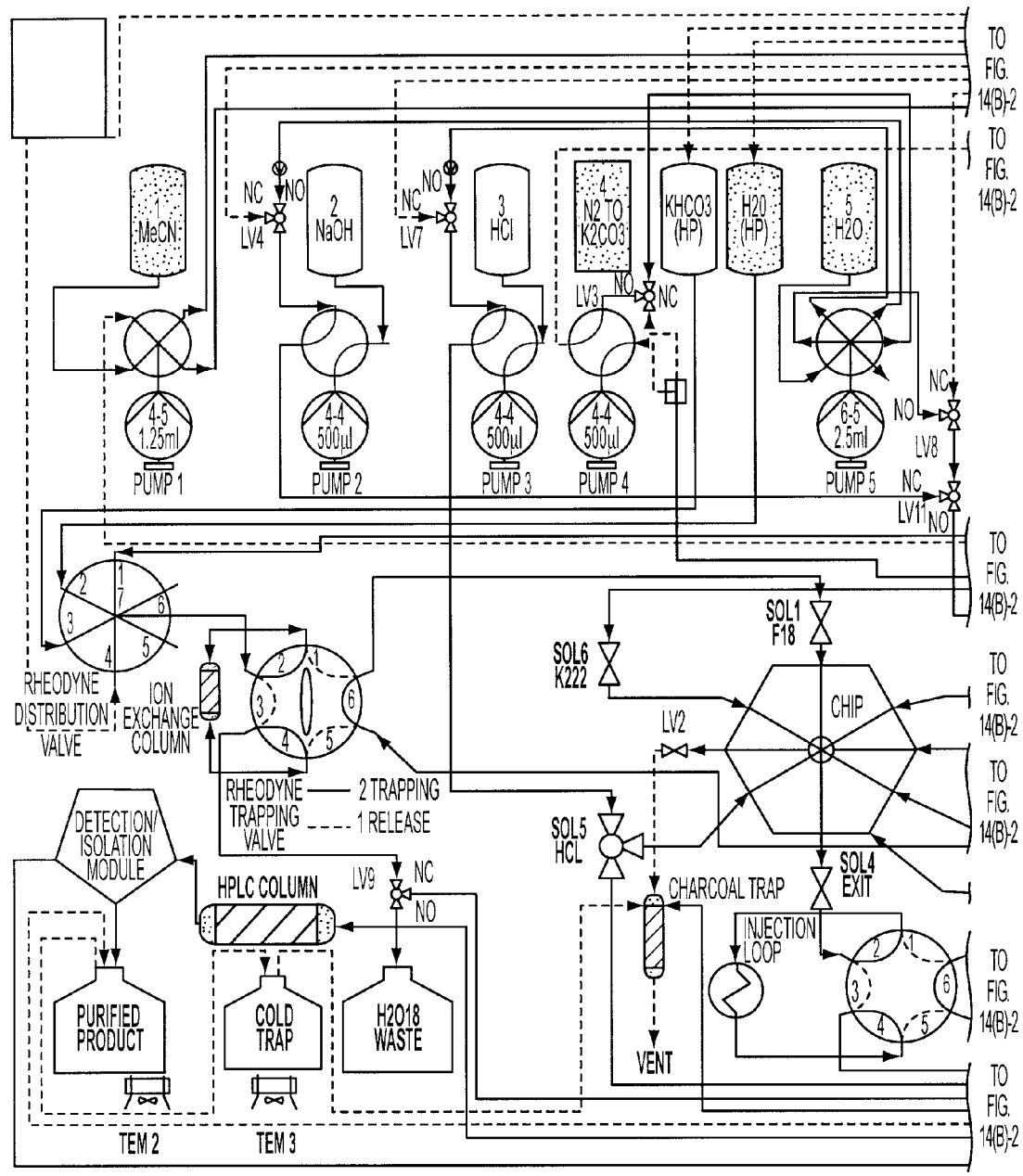
Figures 2, 14B:
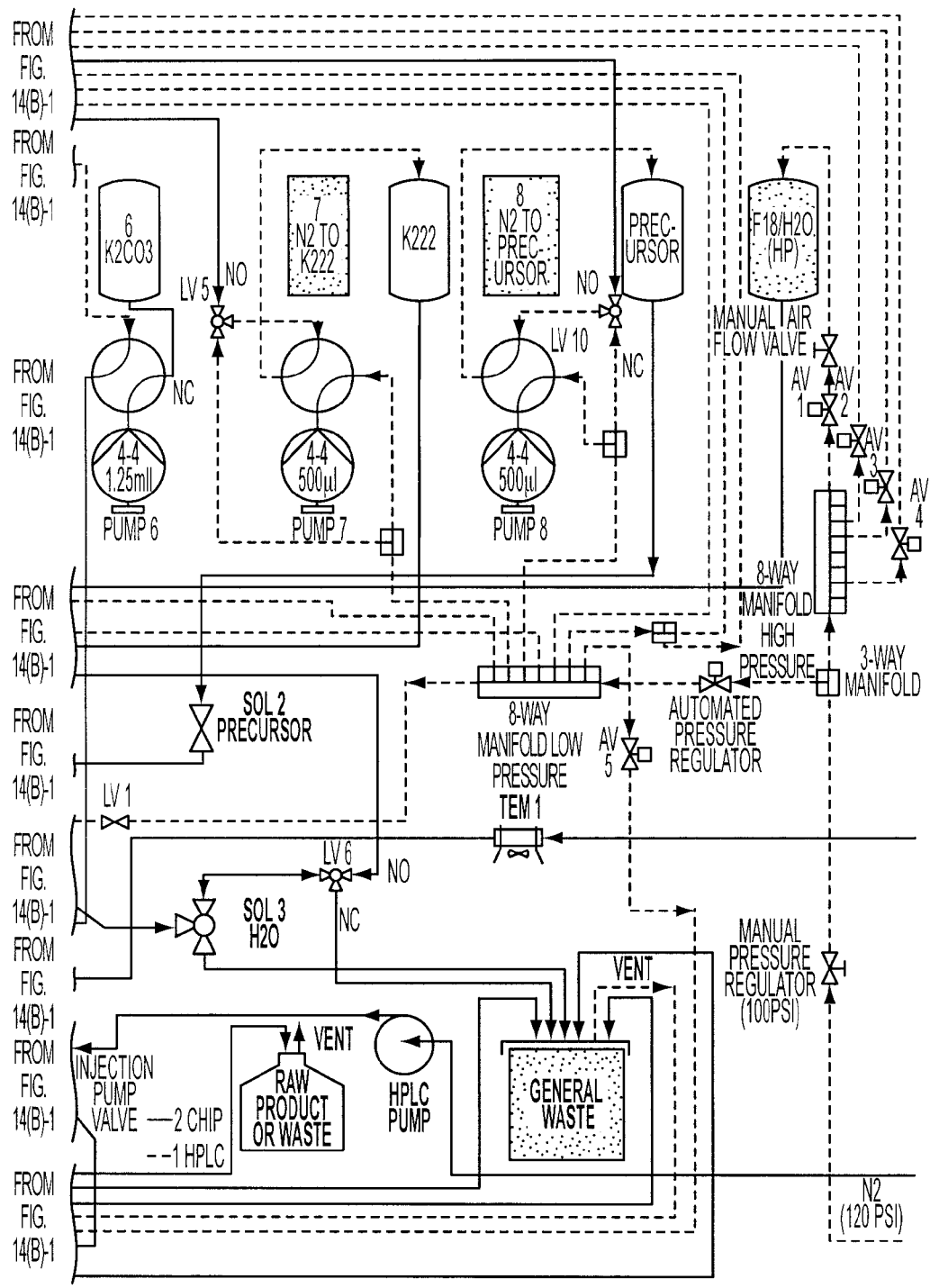

By the way of example, and not limitation, the following description provides a set of steps that may be carried out in accordance with the various embodiments of the present invention for preparation of [18F]FLT. Throughout the following description reference is made to the various components that are shown in FIG. 14(A) and FIG. 14(B). All terms mentioned in quotation marks (such as "LV2") correspond to the components labeled similarly in FIG. 14. The two figures are similar to each other in that they both illustrate a detailed diagram of the various components as well as fluid and gas network in accordance with an embodiment of the present invention. However, FIG. 14(B) includes additional details regarding the purification system as disclosed herein. Although the following description provides specific values and parameters associated with an exemplary use of the system in accordance with FIG. 14(B), these values and parameters may be modified to utilize the present system without departing from the scope of the various embodiments of the present invention. Before the synthesis of [18F]FLT, the instrument goes through a cleaning cycle, then the system has to complete the priming step which brings the reagents used in excess (HCl and $H_2O$) right up to the chip via the dead volume bypass system (automatically).

Approximately 2.0 ml of radioactive target water containing [F-18]fluoride is placed in the appropriate vial (labeled "F18/$H_2O$(HP)") before the trapping procedure is started. "Rheodyne Trapping Valve" is set to a "trapping" position. High pressure nitrogen controlled by air valve "AV1" is used to force the target water through the "Ion Exchange Column" which traps and holds the [F-18]fluoride while passing the stripped water on to a collection vial (labeled "$H_2O18$ Waste"). Then, the "Rheodyne Trapping Valve" is switched to the "release" position. Next, 15 µl of $K_2CO_3$ may be aspirated from the "6 $K_2CO_3$" vial, with "Pump 6", and dispensed toward the "Ion Exchange Column". A precise amount of nitrogen is then aspirated by "Pump 4" from the "8-Way Manifold Low Pressure" and dispensed toward the 15 µl of $K_2CO_3$ after opening chip valve "SOL 1 F18" and vent valve "LV2". This nitrogen is used to push the K2CO3 through the "Ion Exchange Column" in the opposite direction to release the trapped [F-18]fluoride and then deliver it into the reaction chamber within the microfluidic "Chip". At this time, chip valves "SOL 1 F18" is closed and chip valve "SOL 6 K222" is opened. A precise amount of nitrogen is aspirated by "Pump 7" from the "8-Way Manifold Low Pressure" and dispensed toward the "K222" vial which contains a pre-measured amount (e.g., 35 µl) of Kryptofix2.2.2, and is used to move the Kryptofix2.2.2 into the reaction chamber. Chip valve "SOL 6 K222" is closed, and the reaction chamber is prepared for the next step which is the Fluoride Drying/$H_2O$ Evaporation step.

Fluoride Drying/$H_2O$ Evaporation: The "Automated Pressure Regulator" is set to 15 psig, the chip thermoelectric module "TEM 1" temperature is set to 110 degrees C., the chip vent valve "LV 2" stays open from the previous step, the chip nitrogen valve "LV1" is opened, a timer is set, and the fluoride drying and $H_2O$ evaporation step begins. The pressure of 15 psig is started at 1 psig and increased 1 psig every 3 seconds until 15 psig is reached. The pressure is controlled by the "Automated Pressure Regulator". The precise extent of drying is determined using the timer plus the feedback from the machine vision system. In the machine vision system, several boxes within the view area of the reactor are programmed when wet and dry using red, green, blue, hue, saturation, and brightness values for each box. These values plus time are used to determine the level of dryness. The chip nitrogen valve "LV1" is now closed.

The machine vision system (not shown in the FIG. 14) comprises a high resolution camera and specially designed software to allow monitoring of the reaction chamber, providing feedback, and triggering subsequent steps of the process in accordance with the feedback.

After drying, the chip vent valve "LV 2" stays open. Chip valve "SOL 2 Precursor" is opened, and a precise amount of nitrogen is aspirated from "Pump 8" and dispensed toward the "Precursor" vial, and is used to move the Precursor into the reaction chamber. Note that the "Precursor" vial contains a pre-measured amount (40 µl) of the Precursor. Chip valve "SOL 2 Precursor" is closed after the entire volume is delivered to the chip. Chip vent valve "LV2" is closed, and the reaction chamber is prepared for the next step which is the Fluorination step.

Fluorination: Pressure is set in the reaction chamber by opening "LV1" and setting the pressure to 15 psi by the "Automated Pressure Regulator" and then closing "LV1". With all the chip valves closed, the chip thermoelectric module "TEM 1" is set to 140 degrees C., and the timer is set to 180 seconds. At the end of the timer duration, the temperature is reduced to 60 degrees C. by "TEM 1". Then "LV1" is opened and pressure is reduced to 0 psi by the "Automated Pressure regulator" followed by closing "LV1". Next the Acetonitrile Evaporation step begins. Pressurizing the reactor with a small pressure such as 15 psi suppresses the solvent evaporation and boiling which lead to product decomposition or reactant loss into the vent. In another embodiment applying high pressure also improves the reaction kinetics and results in higher yields.

Acetonitrile Evaporation: The "Automated Pressure Regulator" is set to 3 psig, the chip thermoelectric module "TEM 1" is set to 60 degrees C., the chip vent valve ("LV2") is opened, the chip nitrogen valve ("LV1") is opened, a timer is set for 17 sec, and the Acetonitrile Evaporation step begins. The pressure of 3 psig is started at 1 psig and increased 1 psig every 3 seconds until 3 psig is reached. The precise drying amount is determined using the timer plus the feedback from the machine vision system. In the machine vision system, several boxes within the view area of the reactor are programmed when wet and dry using red, green, blue, hue, saturation, and brightness values for each box. These values plus time are used to determine the level of dryness. The chip nitrogen valve ("LV1") is closed while chip vent valve ("LV2") stays open. The acetonitrile evaporation is designed to be only partial—just to clear enough room for the acid. If the evaporation is allowed to proceed to completion, it will be impossible to dissolve the organic residue in aqueous acid without stirring.

HCl Filling: The chip thermoelectric module "TEM 1" stays at 60 degrees C., the "Automated pressure regulator" is set to 0 psig. Then 30 µl of 3N HCl is aspirated from the "HCl" vial with "Pump 3", chip valve "SOL 5HCl" is opened, and the 30 µl of HCl is dispensed into the reactor. Then chip valve "SOL 5HCl" is closed, and chip vent valve ("LV2") is closed.

Hydrolysis: All the chip valves remain closed, "TEM 1" is set to 100 degrees C., and a timer is set to 180 seconds. After 180 seconds, the Hydrolysis step is over and the Elution step begins. In case of FLT the pressure is left at 0 during hydrolysis, but in other processes requiring higher temperatures and pressures during this step, an elevated pressure can be maintained during hydrolysis in a similar way it is done during fluorination, but will need to be reduced to 0 before the elution step. Leaving the pressure at 0 during the hydrolysis step allows mild boiling of the reaction mixture, which helps with the mixing of the components without losing the liquid into the vent channels.

Elution: The "Automated Pressure Regulator" stays at 0 psig, "TEM 1" stays at 60 degrees C., the chip vent valve ("LV2") is closed, the chip nitrogen valve ("LV1") is closed, and 2.0 ml of H2O are aspirated from the "H2O" vial with "Pump 5". Chip valve "SOL 3H2O" is opened, chip valve "SOL 4 EXIT" is opened, and 2.0 ml of H2O are dispensed toward the chip to elute the raw product either into the "Raw Product Vial" or into the "Injection Loop" depending on the position chosen for the "Injection Loop Valve". Chip valve "SOL 3H2O" is closed, then chip valve "SOL 4 EXIT" is closed. If the product is delivered to the "Raw Product Vial" it can now be removed from the system and analyzed.

Purification: If the product is eluted into the "Injection Loop", now the "Injection Loop Valve" has to switch from "Chip" to "HPLC" position. Next the "HPLC Pump" is started forcing the raw product into the "HPLC Column". The column separates various compounds in the raw product stream so that they come off the column at various retention times (HPLC). The system is programmed to detect and isolate known compounds such as FLT automatically while executing pre-programmed gradient, step or isocratic programs. A radiation detector and a UV detector that comprise the "Detection/Isolation Module" are used to monitor the liquid leaving the column and to trigger a valve to direct the purified product into a "Purified Product" vial and the remaining liquid into the "General Waste" vial.

In another embodiment, in order to minimize the product transfer (and loss) the reaction chamber is used instead of the injection loop and the HPLC pump is plumbed directly to one of the chip inlets while an outlet is connected directly to the HPLC column. This arrangement eliminates the need for an injection loop. Table 2 illustrates exemplary performance characteristics associated with the chip in[F-18]FLT radiosynthesis.

TABLE 2

Exemplary Chip Performance in [F-18]FLT Radiosynthesis

| Activity | Performance |
|---|---|
| F-18 trapping and release | 99.8% |
| Fluorination yields | up to 95% |
| Hydrolysis | up to 99% |
| Overall yield of [F-18]FLT | up to 85% |
| Synthesis run time | 17 min |
| Purification | 5 min |
| Product purity | 99.6% |

Finally, there is the Cleaning step which performs the ion exchange column regeneration as well as the microfluidic chip cleaning before the next run.

Column Regeneration: A high pressure nitrogen valve "AV3" is turned on and 1.0 ml of KHCO$_3$ pre-loaded into the "KHCO3 (HP)" vial is forced through the "Ion Exchange Column" with "Rheodyne Trapping Valve" in the "trapping" position. "AV3" valve is turned off when the last bit of liquid passes the interface detector downstream from the "Rheodyne Trapping Valve". Now "AV2" high pressure valve is turned on and 2.0 ml of H2O is forced out of the "H2O(HP)" vial through the column. Nitrogen is then allowed to flow through the column for drying. "AV2" is then turned off.

Chip Cleaning is a sequence of steps that prepares the system for the next run. This can be achieved without the need to open shielding and without manual operations. In one exemplary embodiment, the chip cleaning may be carried out in accordance with the following steps. First the acid lines are flushed with N$_2$ to remove all acid into the waste. Then the acid lines and the reaction chamber are flushed with water followed by N$_2$ to remove traces of acid. Then the K$_2$CO$_3$ lines and reactor are flushed with water followed by N$_2$. Next, Kryptofix2.2.2 lines are flushed with Acetoniotrile followed by N$_2$. Then the precursor lines are flushed with Acetonitrile and N$_2$, but this time, the solvent exits the chip through the crude product line and flushes the HPLC injection loop. Finally N$_2$ is run through both Kryptofix2.2.2 and Precursor vials exiting through the reactor exit line and vent exit while the reactor is heated to make sure it is dry. When all the valves close and pressure is released the system is ready for the next run.

Example Embodiment

Purification and formulation systems

FIGS. 23 to 27 illustrate the various components and steps that are involved in purification and formulation in accordance with example embodiments of the present invention. These systems can be incorporated into the same instrument as the synthesis or following the modular design approach can be packaged into a separate instrument that is complementary to the synthesis instrument. FIG. 23(A) illustrates an exemplary diagram for transferring a sample from chip to the sample loading loop. The sample loading valve of FIG. 23(A) is in loading position. FIG. 23(B) illustrates the injection of the sample from sample loading loop to C18 column (or any other HPLC column). The sample loading valve of FIG. 23(B) is in inject position. Accordingly, the sample components are separated in the C18 column and detected with radiation and UV detection system sequentially. Desired sample fraction may be collected while the rest may be treated as waste. In another embodiment several fractions may be collected separately using an additional distribution valve in the product line past the UV detection module.

Figure 24:
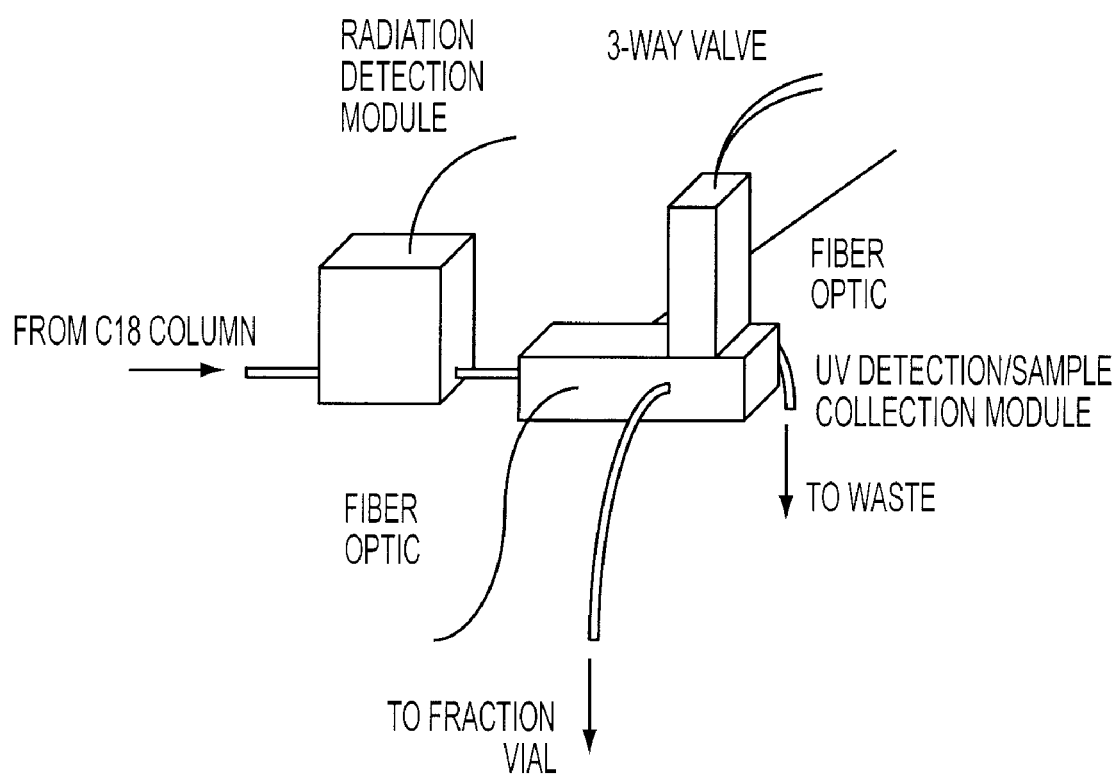
FIG. 24 is a detection and isolation system diagram in accordance with an exemplary embodiment of the present invention.
Figure 25:
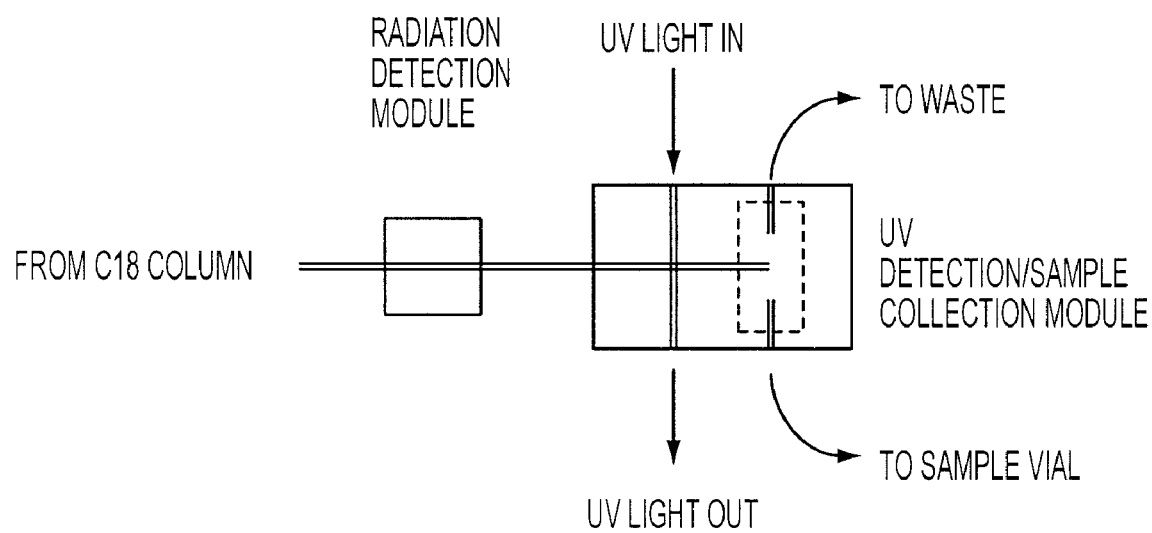
FIG. 25 is a detection and isolation device diagram in accordance with an exemplary embodiment of the present invention.

FIG. 24 illustrates an exemplary radiation detection module that is based on a CsI (TI) scintillating crystal/photodiode combination that is shielded with a lead housing. The UV detection and sample collection module may be built on the same substrate. The UV detection system is composed of a light source, a CCD spectrometer and fiber optics. The fraction collection may be controlled with a 3-way solenoid valve. FIG. 25 is a top view showing the internal structure of the detection/sample collection modules. An example radiation detection module is based on a CsI (TI) scintillating crystal/photodiode combination, which is shielded with a lead housing. The UV detection and sample fraction may be built on the same substrate. The UV detection system is composed of a light source, a CCD spectrometer and fiber optics. The fraction collection may be controlled with a 3-way solenoid valve.

Figure 26:
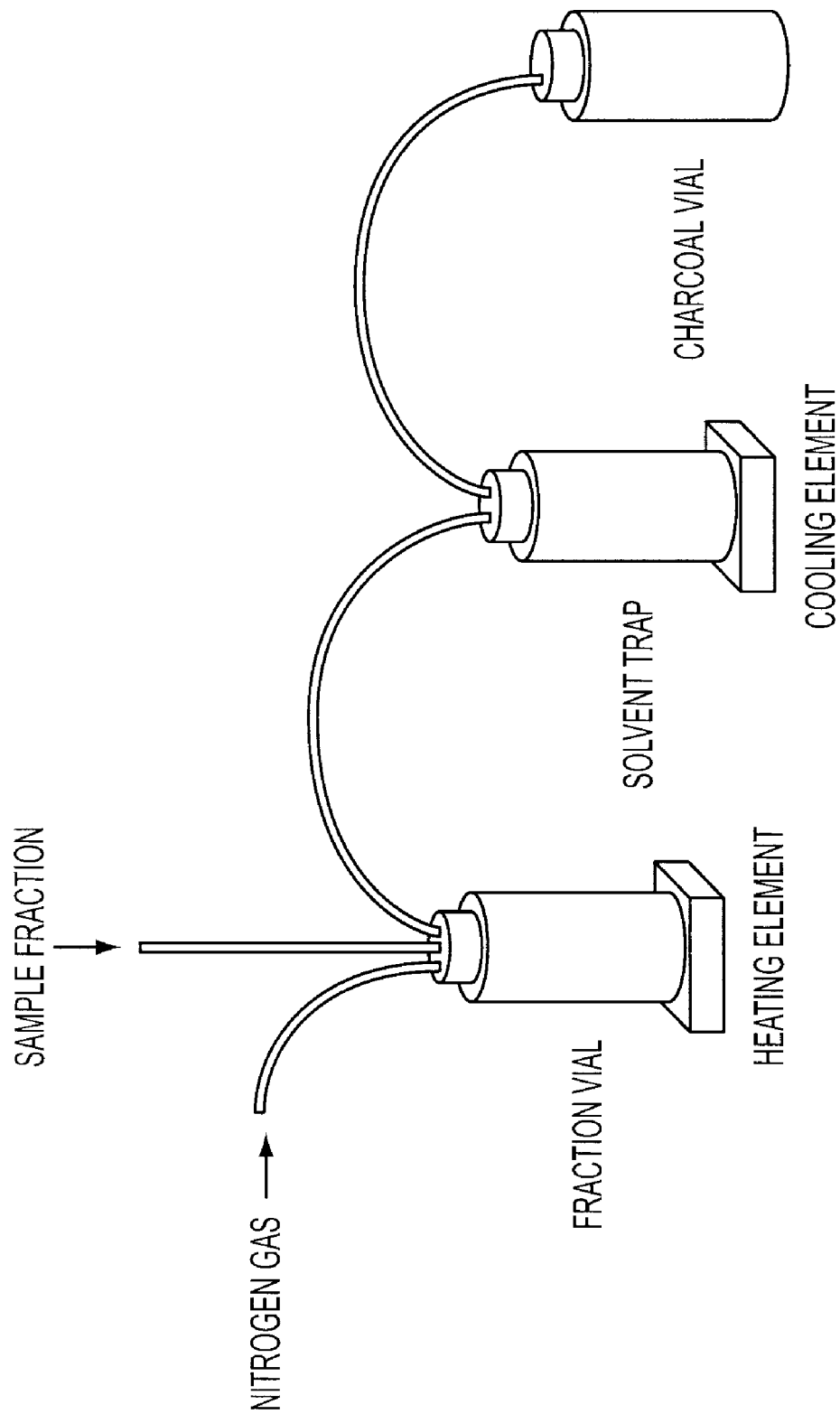
FIG. 26 is a solvent removal diagram in accordance with an exemplary embodiment of the present invention.
Figure 27:
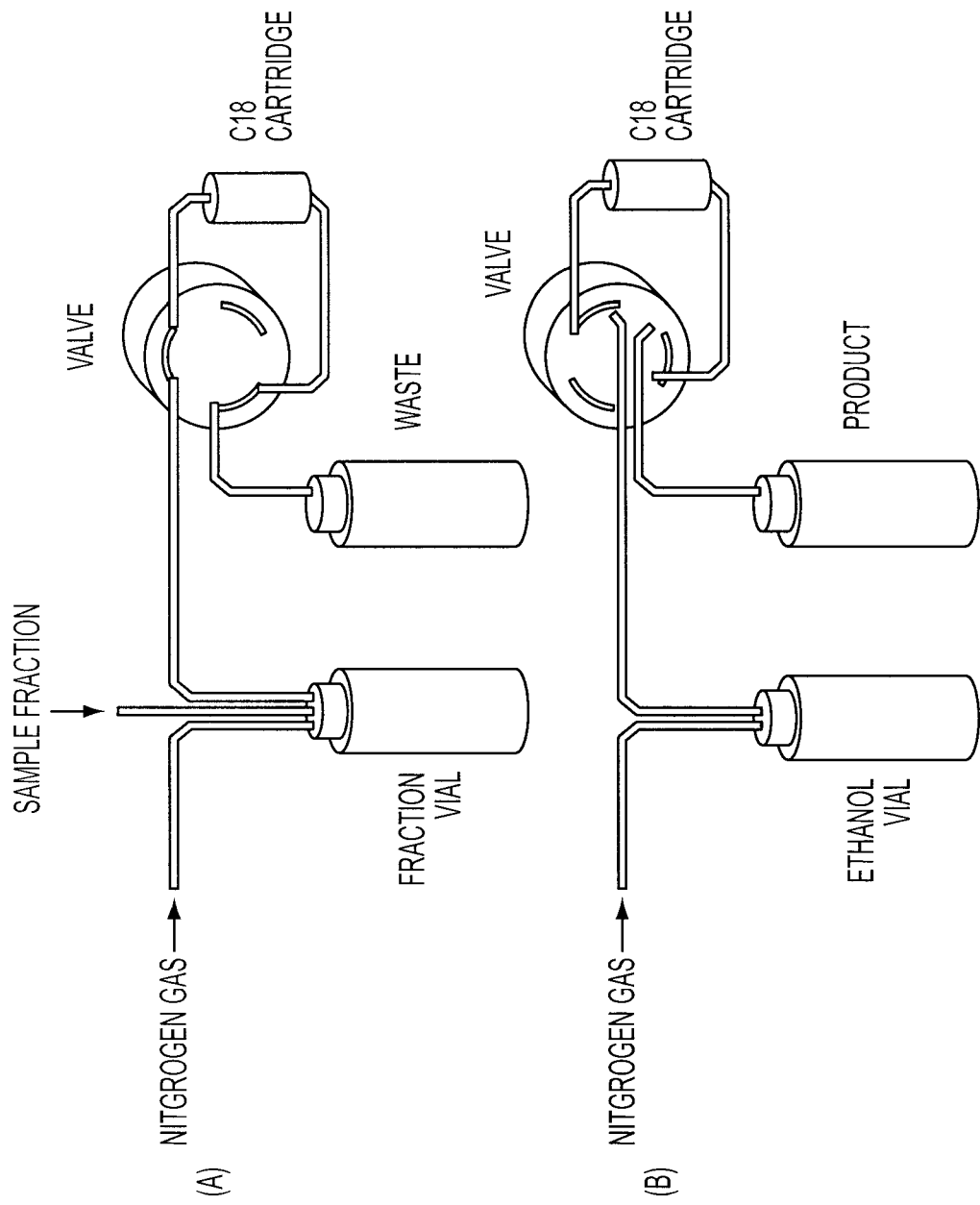
FIG. 27 is solvent removal diagram in accordance with an exemplary embodiment of the present invention.

FIG. 26 illustrates an exemplary solvent removal module. Heating of the fraction vial and flowing nitrogen facilitate solvent removal. As illustrated in FIG. 26, the removed solvent may first be condensed in the cold trap and further trapped in a charcoal vial. FIG. 27 illustrates another example embodiment in which solvent is removed from the product using a C18 cartridge. In FIG. 27(A), the fraction vial is preloaded with excessive water, which dilutes the sample fraction. With nitrogen, the diluted sample fraction passes the C18 cartridge, trapping the desired product. More water may be delivered through sample fraction line, washing the residual solvents from the C18 cartridge. In FIG. 27(B), the valve is switched to allow a small amount of ethanol flow through the cartridge to release the trapped product which is subsequently diluted with water to an injectable EtOH/H$_2$O ratio.

All references cited herein are incorporated by reference as if each had been individually incorporated by reference in its entirety. In describing embodiments of the present invention, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A microfluidic chip for radiosynthesis of a radiolabeled compound, comprising:
   a reaction chamber integral to said microfluidic chip, wherein said reaction chamber has a cylindrical shape;
   one or more flow channels connected to said reaction chamber;
   one or more vents connected to said reaction chamber;
   wherein said cylindrical shape of said reaction chamber is adapted to allow gas to flow through said reaction chamber while inhibiting flow of a solution contained in said reaction chamber through said vents out of said reaction chamber; and
   one or more integrated valves to effect flow control in and out of said reaction chamber.

2. The chip of claim 1, further comprising a lid section, wherein said reaction chamber is located within a reactor section and the lid section and the reactor section are press-fitted together.

3. The chip of claim 2, wherein at least a portion of said lid section is transparent.

4. The chip of claim 2, wherein said lid section includes a glass window within a frame.

5. The chip of claim 2, further comprising an interface configured to effect delivery of products to said reaction chamber.

6. The chip of claim 5, wherein said interface is connected to said reactor section.

7. The chip of claim 1, wherein a floor of said reaction chamber comprises a curved section.

8. The chip of claim 1, wherein said chip has a hexagonal shape.

9. The chip of claim 1, further comprising a heater for heating said reaction chamber.

10. The chip of claim 9, wherein said heater comprises at least one of a heating element, a resistive heater, a radiator heater, a microwave heater, and a laser device for remote delivery of heat to the reaction chamber.

11. The chip of claim 9, wherein said heater is coupled to said chip through an opening in a base of said chip.

12. The chip of claim 11, wherein an air gap separates said heater from sidewalls of said opening.

13. The chip of claim 9, wherein said heater is separated from said reaction chamber by a section of about 250 microns.

14. The chip of claim 13, wherein said section comprises a doped DCPD material.

15. The chip of claim 1, wherein said valves are controlled by pneumatic actuators or solenoids.

16. The chip of claim 1, wherein said valves comprise a dual port plunger with one or more thin sections that are separated by one or more ridges.

17. The chip of claim 1, wherein said valves comprise a plunger with a thin metal portion, a tip, and one or more o-rings adapted to prevent gas escape from said reaction chamber.

18. The chip of claim 1, further comprising an ion exchange column integrated into the chip.

19. The chip of claim 1, further comprising an HPLC integrated into said chip.

20. The chip of claim 1, further comprising an HPLC integrated into an interface section of said chip.

21. The chip of claim 1, wherein said reaction chamber has a volume of about 60 micro liters.

22. The chip of claim 1, wherein said chip is configured as a closed system with no plumbing extensions.

23. The chip of claim 1, wherein said chip is further adapted to communicate with a network of fluid and gas delivery and removal.

24. The chip of claim 23, further comprising one or more syringes that are used for delivery of at least one of a fluid or gas to said chip.

25. The chip of claim 24, wherein said syringes are located below one or more vials with liquid contents to effect efficient delivery of liquids to said chip.

26. The chip of claim 24, wherein said syringes are used for delivery of gas to said chip.

27. The chip of claim 23, wherein said network is adapted to operate with at least one of a pre-filled individual vial and a pre-packaged cartridge.

28. The chip of claim 27, wherein said cartridge contains a pre-measured amount of reagent sufficient for single use with the chip.

29. The chip of claim 23, wherein a controlled delivery of liquids is effected by gradual increase of pressure against a closed vent.

30. The chip of claim 1, wherein solvent evaporation and vapor removal are effected by flowing gas over the solution inside said reaction chamber.

31. The chip of claim 30, wherein said gas is nitrogen.

32. The chip of claim 1, wherein superheating of the contents of said reaction chamber is effected by closing said vents and heating said reactor chamber with a heater.

33. The chip of claim 32, further comprising pressurizing said reaction chamber prior to applying said heater.

34. The chip of claim 1, further comprising an integrated solvent removal module.

35. The microfluidic chip as recited in claim 1, wherein said vents are configured to allow unrestricted solvent evaporation from said reaction chamber independent of a membrane.

36. A method for radiosynthesis of a radiolabeled compound, comprising;
    introducing one or more reagents into a microfluidic chip, the chip comprising:
        a reaction chamber integral to said microfluidic chip, wherein said reaction chamber has a cylindrical shape,
        one or more flow channels connected to said reaction chamber,
        one or more vents connected to said reaction chamber,
        wherein said cylindrical shape of said reaction chamber is adapted to allow gas to flow through said reaction chamber while inhibiting flow of a solution contained in said reaction chamber through said vents out of said reaction chamber, and
        wherein one or more integrated valves effect flow control in and out of said reaction chamber;
    processing said reagent(s) to generate a radiolabeled compound; and
    collecting said radiolabeled compound.

37. The method for radiosynthesis of a radiolabeled compound as recited in claim 36, wherein said vents are configured to allow unrestricted solvent evaporation from said reaction chamber independent of a membrane.

38. A microfluidic chip for radiosynthesis of a radiolabeled compound, comprising:
    a reaction chamber integral to said microfluidic chip, wherein said reaction chamber has a cylindrical shape;
    one or more flow channels connected to said reaction chamber;
    one or more vents connected to said reaction chamber, wherein said vents are configured to allow unobstructed gas flow through said reaction chamber when said vents are open and said vents are configured to seal said reaction chamber when said vents are closed;
    wherein said cylindrical shape of said reaction chamber is adapted to allow said gas to flow through said reaction chamber while inhibiting flow of a solution contained in said reaction chamber through said vents out of said reaction chamber; and
    a first set of integrated valves that deliver reagents to said reaction chamber; and
    a second set of integrated valves that elute product from said reaction chamber.

39. The microfluidic chip as recited in claim 38, wherein said first set of integrated valves seal said reaction chamber independent of a membrane.

40. A microfluidic chip comprising:
    a reaction chamber integral to said microfluidic chip, wherein said reaction chamber has a cylindrical shape;
    one or more flow channels connected to said reaction chamber; and
    a first vent and a second vent connected to said reaction chamber;
    wherein said reaction chamber is configured to hold a liquid while allowing a flow of gas from the first vent to pass through said reaction chamber above said liquid and out the second vent;
    wherein said cylindrical shape of said reaction chamber is adapted to allow said gas to flow through said reaction chamber while inhibiting flow of said liquid contained in said reaction chamber through the second vent.

41. The microfluidic chip as recited in claim 40, wherein the microfluidic chip is used for radiosynthesis of a radiolabeled compound.

* * * * *